United States Patent
Devaraj et al.

(10) Patent No.: US 9,533,957 B2
(45) Date of Patent: Jan. 3, 2017

(54) TETRAZINES AND METHOD OF SYNTHEZISING THE SAME

(71) Applicant: The Regents of the University of California, Oakland, CA (US)

(72) Inventors: Neal K. Devaraj, San Diego, CA (US); Jun Yang, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/507,509

(22) Filed: Oct. 6, 2014

(65) Prior Publication Data

US 2015/0099277 A1    Apr. 9, 2015

Related U.S. Application Data

(63) Continuation of application No. PCT/US2013/035676, filed on Apr. 8, 2013.

(60) Provisional application No. 61/736,844, filed on Dec. 13, 2012, provisional application No. 61/621,254, filed on Apr. 6, 2012.

(51) Int. Cl.
| | |
|---|---|
| *C07D 257/08* | (2006.01) |
| *C07D 237/26* | (2006.01) |
| *C07D 403/14* | (2006.01) |
| *C07H 13/08* | (2006.01) |
| *C07F 5/02* | (2006.01) |
| *C07H 21/00* | (2006.01) |

(52) U.S. Cl.
CPC ........... *C07D 237/26* (2013.01); *C07D 257/08* (2013.01); *C07D 403/14* (2013.01); *C07F 5/022* (2013.01); *C07H 13/08* (2013.01); *C07H 21/00* (2013.01)

(58) Field of Classification Search
CPC .................................................. C07D 257/08
See application file for complete search history.

(56) References Cited

PUBLICATIONS

Yang et al. Metal-Catalyzed One-Pot Synthesis of Tetrazines Directly from Aliphatic Nitriles and Hydrazine. Angewandte Chemie, International Edition (2012), 51(21), 5222-5225.*
Lim et al. Synthesis of symmetric 3,6-disubstituted-1,2,4,5-tetrazines using an activated catalyst prepared by the reaction of copper nitrate with excess zinc in the presence of hydrazine monohydrate. Bulletin of the Korean Chemical Society, 1995, 16, 374-7- (abstract included only).*
Beynon, G.et al. (1979). "Some 3,4-diazanorcaradienes," *Bulletin des Societes Chimiques Belges* 88(11):905-909.
Clavier, G. et al. (Jun. 9, 2010). "s-Tetrazines as building blocks for new functional molecules and molecular materials," *Chem Rev* 110(6):3299-3314.
Devaraj, N.K. et al. (2011, e-published May 31, 2011). "Biomedical Applications of Tetrazine Cycloadditions," *Accounts of Chemical Research* 44(9):816-827.
Hsieh, C-C et al. (2009, e-published Aug. 5, 2009). Effects of Counteranion on the Pyrazole-Nitrile Coupling Reaction Mediated by Nickel (II) Ions, *Organomettalics* 28:4923-4928.
International Search Report mailed on Jul. 25, 2013, for PCT Application No. PCT/US2013/035676, filed on Apr. 8, 2013, 5 pages.
Kukushkin, V.Y. et al. (2002). "Additions to Metal-Activated Organonitriles," *Chem Rev* 102(5):1771-1802.
Mason, R. et al. (1973). "Reactions of Hydrazines with Platinum-Nitrile Complexes; X-Ray Structural Characterization and Electro-chemistry of *trans*-Bis-1-acetyl-3-t-butyl-1,2,4-triaza-butadieneplatimun." *J.C.S. Chem Comm* pp. 297-299.
Rousselet, G. et al. (1993). "Copper(I)-Induced Addition of Amines to Unactivated Nitriles: The First General One-Step Synthesis of Alkyl Amidines," *Tetrahedron Letters* 34(40):6395-6398.
Sauer, J. et al. (2001). "The Cycloaddition-Cycloelimination Pathway to Homotropilidenes-Synthesis and Properties of Homotropilidenes," *Eur J Org Chem* 2001(14):2639-2657.
Zajac, W.W. et al. (1971). "Reaction of Nitriles with Hydrazine Hydrate and Raney Nickel," *J Org Chem* 36(23):3539-3541.

* cited by examiner

*Primary Examiner* — Brian McDowell
(74) *Attorney, Agent, or Firm* — Mintz Levin Cohn Ferris Glovsky and Popeo, P.C.

(57) ABSTRACT

Provided herein, inter alia, are compositions and methods of synthesis and detection of tetrazines, e.g., a tetrazine of formula

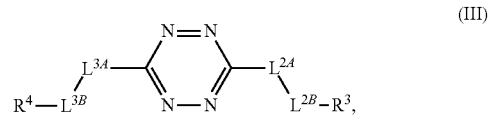

and diazonorcaradienes.

6 Claims, 20 Drawing Sheets

SEQUENCE LISTING

```
<160> NUMBER OF SEQ ID NOS: 5

<210> SEQ ID NO 1
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 1
ttgacgccat cgaaggtagt gttgaat                                          27

<210> SEQ ID NO 2
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 2
attcaacact acctcgatgg cgtcaa                                           26

<210> SEQ ID NO 3
<211> LENGTH: 34
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (14)..(21)
<223> OTHER INFORMATION: Residue  at positions 14-21 is A and up to
      seven of them may be absent

<400> SEQUENCE: 3
```

```
ttgacgccat cgaaaaaaaa aggtagtgtt gaat                                    34

<210> SEQ ID NO 4
<211> LENGTH: 12
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Residue at 5' terminal modified with
      tetrazine-5AmMC6-iFluorT

<400> SEQUENCE: 4
cgatggcgtc aa                                                            12

<210> SEQ ID NO 5
<211> LENGTH: 13
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (13)..(13)
<223> OTHER INFORMATION: Residue at 3' terminal modified with 3AmMO-
      cycloprotene

<400> SEQUENCE: 5
attcaacact acc                                                           13
```

TETRAZINES AND METHOD OF SYNTHEZISING THE SAME

CROSS-REFERENCES TO RELATED APPLICATIONS

This application is a continuation of PCT Application Number PCT/US2013/035676, filed Apr. 8, 2013, which claims priority to Provisional Application No. 61/621,254 filed Apr. 6, 2012, and to Provisional Application No. 61/736,844 filed Dec. 13, 2012.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 88654-921082_ST25.TXT, created on Nov. 7, 2014, 1,837 bytes, machine format IBM-PC, MS-Windows operating system, is hereby incorporated by reference.

STATEMENT AS TO RIGHTS TO INVENTIONS MADE UNDER FEDERALLY SPONSORED RESEARCH AND DEVELOPMENT

This invention was made with government support under grant No. K01EB010078 awarded by the National Institutes of Health. The Government has certain rights in the invention.

BACKGROUND OF THE INVENTION

There is interest in the use of bioorthogonal reactions for live-cell applications. Additional bioorthogonal reactions may expand the toolbox of researchers for live-cell applications. The lack of convenient synthetic methods has been a significant roadblock to broader use and study by the scientific community. Accordingly, there is a need for a convenient synthetic route to synthesize tetrazine derivatives that can aid in live-cell applications. Provided herein are solutions to these and other problems in the art.

BRIEF SUMMARY OF THE INVENTION

In a first aspect a method of synthesizing a 3,6-disubstituted 1,2,4,5-tetrazine is provided. The method includes combining in a reaction vessel a first substituted nitrile having the formula

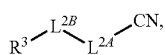

a second nitrile having the formula

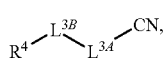

hydrazine and a Lewis Acid catalyst thereby forming a tetrazine of formula

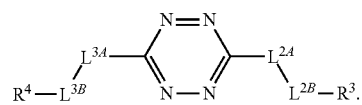

(III)

In another aspect, a method for synthesizing a diazonorcaradiene is provided. The method includes contacting a compound of formula

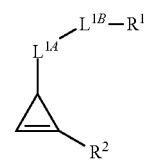

(II)

with a compound of formula

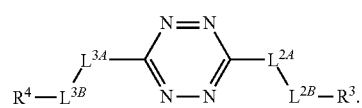

(III)

A diazonorcaradiene of the formula

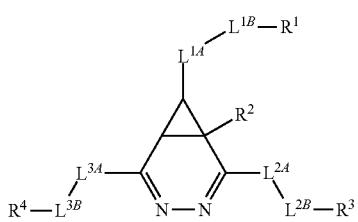

(I)

is thereby formed. $L^{1A}$, $L^{1B}$, $L^{2A}$, $L^{2B}$, $L^{3A}$, and $L^{4A}$ are independently a bond, —C(O)—, —O—, —S—, —NH—, —NR$^5$—, —C(O)NR$^6$—, —S(O)$_n$—, —S(O)NR$^7$—, —OP(O)(OR$^8$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted arylene-alkylene, or substituted or unsubstituted heteroarylene. $R^1$, $R^3$, and $R^4$ are independently hydrogen, halogen, —N$_3$, —CF$_3$, —CCl$_3$, —CBr$_3$, —CI$_3$, —CN, —CHO, —OH, —NH, —NH$_2$, —COOH, —CONH$_2$, —NO$_2$, —S, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a detectable moiety, a water soluble moiety or a biomolecule. $R^2$ is $C_1$-$C_5$ substituted or unsubstituted alkyl. $R^5$, $R^6$, $R^7$, $R^8$ are independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n is 1 or 2

In another aspect, a method is provided for synthesizing a compound having the formula:

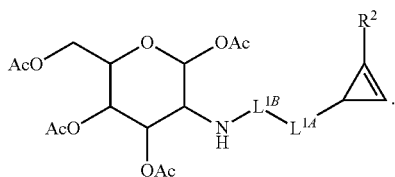
(VIII)

The method includes contacting a peracetylated hexosamine having formula

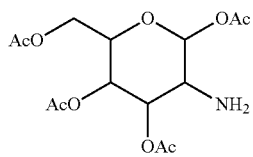 [SMILES: CC(=O)OCC1OC(OC(C)=O)C(N)C(OC(C)=O)C1OC(C)=O]

with a compound having formula

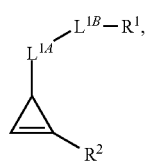
(II)

thereby synthesizing a compound having formula (VIII).

In another aspect, a method is provided for detecting the presence of a compound in a cell. The method includes contacting a cell or organism with a compound of formula

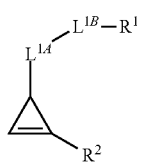
(II)

wherein $R^2$ is a compound moiety. The organism or cell is allowed to process the compound of formula (II). The method further includes contacting the cell with a compound of formula

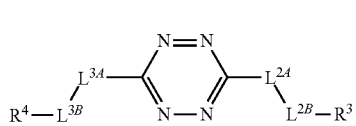
(III)

wherein $R^3$ is a detectable moiety and allowing the compound of formula (III) to react with the compound of formula (II) thereby forming the diazonorcaradiene of formula

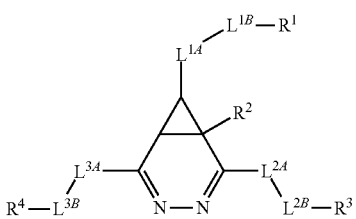
(I)

as described above. The detectable moiety is then detected thereby detecting the presence of the compound moiety in the cell.

In another aspect a method is provided for ligating a first nucleic acid and a second nucleic acid. The method includes combining a template nucleic acid, the compound of formula

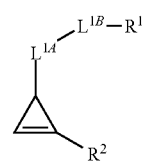
(II)

as described herein and a compound of formula

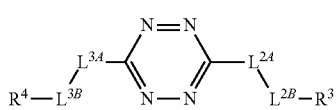
(III)

as described herein in a reaction vessel, wherein $R^1$ is a first nucleic acid moiety and $R^3$ is a second nucleic acid moiety. The template nucleic acid includes a first nucleic acid sequence that is at least partially complementary to the first nucleic acid and a second nucleic acid sequence that is at least partially complement to the second nucleic acid. The first nucleic acid moiety and the second nucleic acid moiety are allowed to hybridize to the template nucleic acid. The compound of formula (II) as described is allowed to react with a compound of formula (III) to from a diazonorcaradiene for formula

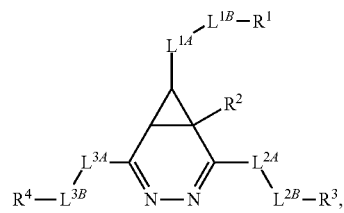
(I)

wherein $R^1$ is the first nucleic acid moiety and $R^3$ is the second nucleic acid moiety, thereby ligating the first nucleic acid moiety and the second nucleic acid moiety.

In another aspect is a compound having formula:

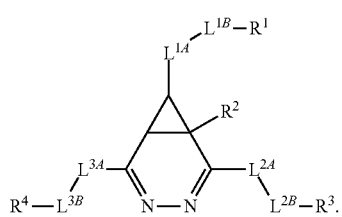

(I)

$L^{1A}$, $L^{1B}$, $L^{2A}$, $L^{2B}$, $L^{3A}$, and $L^{3B}$ are independently a bond, —C(O)—, —O—, —S—, —NH—, —NR$^5$—, —C(O)NR$^6$—, —S(O)$_n$—, —S(O)NR$^7$—, —OP(O)(OR$^8$)O—, substituted or unsubstituted alkylene, substituted or unsubstituted heteroalkylene, substituted or unsubstituted cycloalkylene, substituted or unsubstituted heterocycloalkylene, unsubstituted arylene, substituted or unsubstituted arylene-alkylene, or substituted or unsubstituted heteroarylene. $R^1$, $R^3$, and $R^4$ are independently hydrogen, halogen, —N$_3$, —CF$_3$, —CCl$_3$, —CBr$_3$, —CI$_3$, —CN, —CHO, —OH, —NH, —NH$_2$, —COOH, —CONH$_2$, —NO$_2$, —S, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a detectable moiety, a water soluble moiety or a biomolecule. $R^2$ is $C_1$-$C_5$ substituted or unsubstituted alkyl. $R^5$, $R^6$, $R^7$, $R^8$, are independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n is 1 or 2.

In another aspect is a compound having formula:

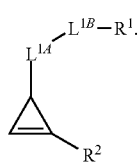

(II)

$L^{1A}$ and $L^{1B}$ are independently a bond, —C(O)—, —O—, —S—, —NH—, —NR$^5$—, —C(O)NR$^6$—, —S(O)$_n$—, —S(O)NR$^7$—, —OP(O)(OR$^8$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is hydrogen, halogen, —N$_3$, —CF$_3$, —CCl$_3$, —CBr$_3$, —CI$_3$, —CN, —CHO, —O, —OH, —NH, —NH$_2$, —COOH, —CONH$_2$, —NO$_2$, —S, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a detectable moiety, a water soluble moiety or a biomolecule. $R^2$ is $C_1$-$C_5$ substituted or unsubstituted alkyl. $R^5$, $R^6$, $R^7$, $R^8$, are independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n is 1 or 2.

In another aspect is a compound having formula:

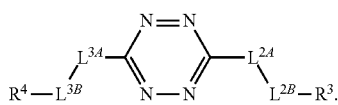

(III)

$L^{2A}$, $L^{2B}$, $L^{3A}$, and $L^{3B}$ a L are independently a bond, —C(O)—, —O—, —S—, —NH—, —NR$^5$—, —C(O)NR$^6$—, —S(O)$_n$—, —S(O)NR$^7$—, —OP(O)(OR$^8$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted arylene-alkylene, or substituted or unsubstituted heteroarylene. $R^3$ and $R^4$ are independently hydrogen, halogen, —N$_3$, —CF$_3$, —CCl$_3$, —CBr$_3$, —CI$_3$, —CN, —CHO, —OH, —NH, —NH$_2$, —COOH, —CONH$_2$, —NO$_2$, —S, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a detectable moiety, a water soluble moiety or a biomolecule. $R^5$, $R^6$, $R^7$, $R^8$, are independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n is 1 or 2.

In another aspect is a compound having formula:

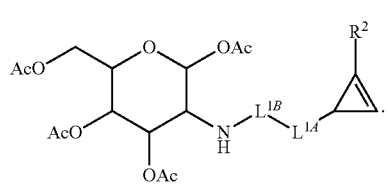

(VIII)

$L^{1A}$ and $L^{1B}$ are independently a bond, —C(O)—, —O—, —S—, —NR$^5$—, —C(O)NR$^6$—, —S(O)$_n$—, —S(O)NR$^7$—, —OP(O)(OR$^8$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is hydrogen, halogen, —N$_3$, —CF$_3$, —CCl$_3$, —CBr$_3$, —Cl$_3$, —CN, —CHO, —OH, —NH, —NH$_2$, —COOH, —CONH$_2$, —NO$_2$, —S, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a detectable moiety, a water soluble moiety or a biomolecule. $R^2$ is $C_1$-$C_5$ substituted or unsubstituted alkyl. $R^5$, $R^6$, $R^7$, $R^8$, are independently hydrogen, halogen, —N$_3$, —NO$_2$, —CF$_3$, —CCl$_3$, —CBr$_3$, —Cl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n is 1 or 2.

DETAILED DESCRIPTION OF THE INVENTION

I. Definitions

Figure 1:
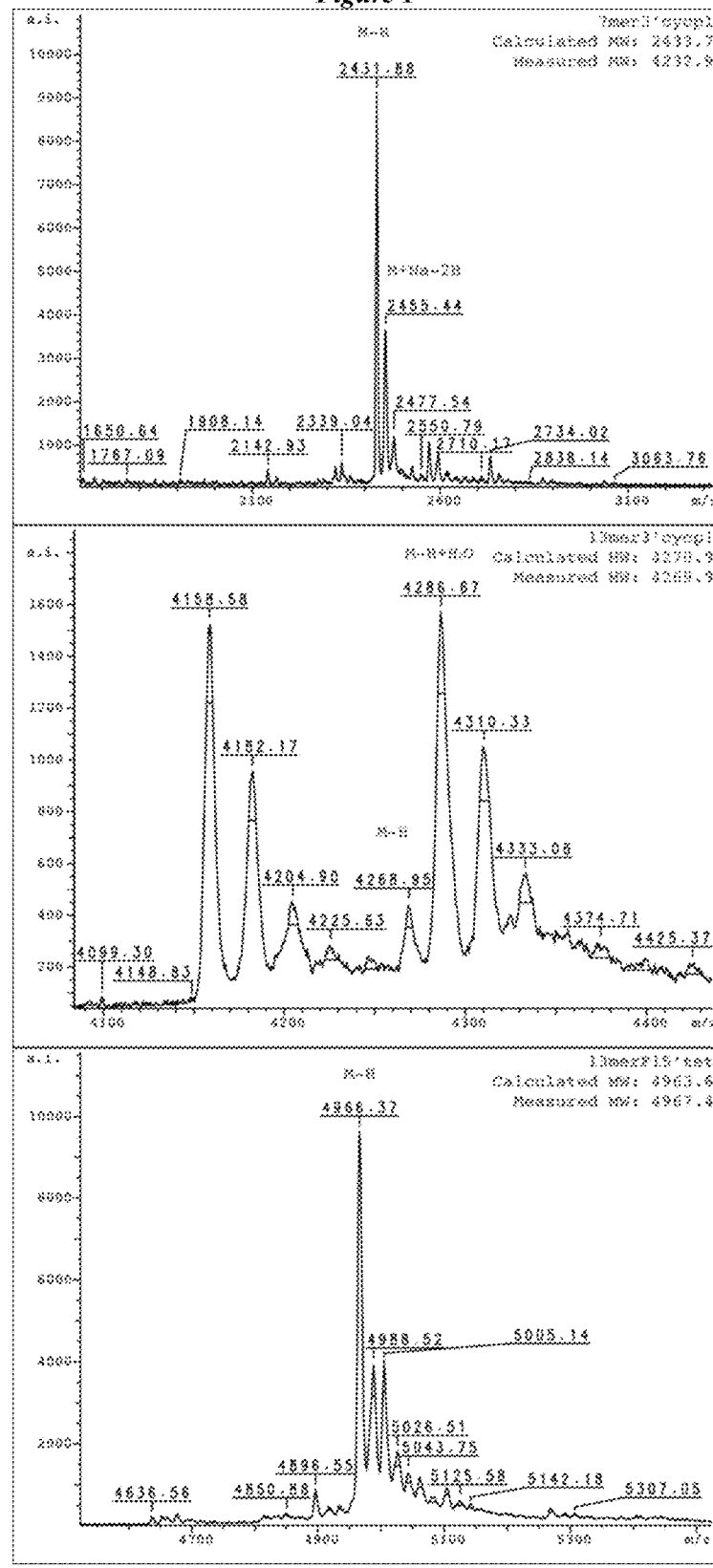
FIG. 1. MALDI MS m/z spectra of modified oligonucleotides.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, S, Se and Si, and wherein the nitrogen, selenium, and sulfur atoms may optionally be oxidized, and the nitrogen heteroatom may optionally be quaternized. The heteroatom(s) O, N, P, S, Se, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SeR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (e.g. 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms (e.g. N, O, or S), wherein sulfur heteroatoms are optionally oxidized, and the nitrogen heteroatoms are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substitutents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

As used herein a "arylene-alkylene is an arylene moiety substituted with an alkylene moiety. In some embodiments an arylene-alkylene may be a -phenylene-methylene such as

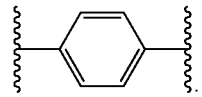

The term "oxo," as used herein, means an oxygen that is double bonded to a carbon atom.

The term "alkylsulfonyl," as used herein, means a moiety having the formula —S(O$_2$)—R', where R' is an alkyl group as defined above. R' may have a specified number of carbons (e.g., "C$_1$-C$_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:
(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, and heteroaryl, substituted with at least one substituent selected from:
(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
(ii) alkyl, heteroalkyl, cycloalkyl, heterocycloalkyl, aryl, and heteroaryl, substituted with at least one substituent selected from:
(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_5$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

The symbol "〜" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The term "tetrazine" refers in the customary sense to a six-membered ring containing four nitrogen atoms. Absent express indication otherwise, the term tetrazine as used herein refers to the isomer of tetrazine with formula 1,2,4,5-tetrazine. The term "symmetric" in the context of substitution of a chemical moiety, e.g., substitution of tetrazine, refers in the customary sense to disubstitution with the same substituent, e.g., 3,6-dimethyl-1,2,4,5-tetrazine. Conversely, the term "asymmetric" in this context refers to disubstitution with different substituents.

A "nitrile" refers to a organic compound having a —CN group.

A "diazonorcaradiene" as used herein refers to a fused ring compound having a formula:

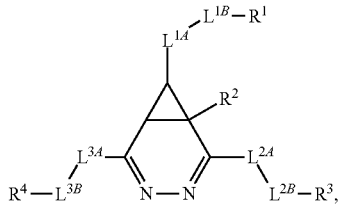

wherein $L^{1A}$, $L^{1B}$, $L^{2A}$, $L^{2B}$, $L^{3A}$, $L^{3B}$, $R^1$, $R^2$, $R^3$ and $R^4$ are as defined herein.

A "hexosamine" as used herein refers to a six-carbon amino sugar in which at least one of the sugar hydroxyls (—OH) has been replaced with an amine (—NH$_2$). Exemplary hexosamines include mannosamine and glucosamine.

As used herein, a molecule is "peracetylated" when all its functional groups (e.g. reactive groups) have been acetylated. Such exemplary peracetylated molecules are peracetylated-hexosamines in which all hydroxyl (—OH) moieties of the amino sugar are acetylated. Peracetylation may provide for greater solubility of non-peracetylated counterparts. Exemplary peraceylated molecules may have the formula:

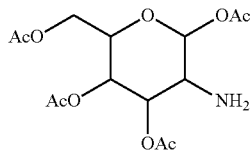 [SMILES: CC(=O)OCC1OC(OC(C)=O)C(N)C(OC(C)=O)C1OC(C)=O]

A "protected secondary amine" refers to the covalent attachment of a monovalent chemical moiety to an amine nitrogen atom that functions to prevent the amine moiety from reacting with reagents used in the chemical synthetic methods described herein (commonly referred to as "protecting" the amine group) and may be removed under conditions that do not substantially degrade the molecule of which the amine moiety forms a part (commonly referred to as "deprotecting" the amine group) thereby yielding a free amine. An amine protecting group can be acid labile, base labile, or labile in the presence of other reagents. Amine protecting groups include but are not limited to: -carbamates (such as -carbobnzyloxy (Cbz), -t-butoxycarbonyl (t-Boc), -fluorenylmethyloxycarbonyl (Fmoc), and -allyl carbmates), -benzyl, -4-methoxyphenyl, or -2,4-dimethoxyphenyl.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers nucleic acids that have the same basic chemical structure as a naturally occurring nucleic acids. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothioates, phosphoramidates, methyl phosphonates, chiral-methyl phosphonates, 2-O-methyl ribonucleotides, and peptide-nucleic acids (PNAs).

"Synthetic mRNA" as used herein refers to any mRNA derived through non-natural means such as standard oligonucleotide synthesis techniques or cloning techniques. Such mRNA may also include non-proteinogenic derivatives of naturally occurring nucleotides. Additionally, "synthetic mRNA" herein also includes mRNA that has been expressed through recombinant techniques or exogenously, using any expression vehicle, including but not limited to prokaryotic cells, eukaryotic cell lines, and viral methods. "Synthetic mRNA" includes such mRNA that has been purified or otherwise obtained from an expression vehicle or system.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The terms "identical" or percent "identity," in the context of two or more nucleic acids, refer to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

A variety of methods of specific DNA and RNA measurements that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., quantitative PCR, dot blot, or array).

The sensitivity of the hybridization assays may be enhanced through use of a nucleic acid amplification system that multiplies the target nucleic acid being detected. Amplification can also be used for direct detection techniques. Examples of such systems include the polymerase chain reaction (PCR) system and the ligase chain reaction (LCR) system. Other methods include the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including Taqman® and molecular beacon probes can be used to monitor amplification reaction products in real time.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The word "protein" denotes an amino acid polymer or a set of two or more interacting or bound amino acid polymers.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization. In some embodiments the cell is a cancer cell line such as SKBR3 or LS174T.

A "biomolecule" or "biomolecule moiety" as used herein refers any molecule produced in a living cell or any synthetically derived molecule that mimics or is an analogue of a molecule produced in a living cell. Biomolecules herein include nucleotides, polynucleotides (e.g. RNA, DNA), amino acids, peptides, polypeptides, proteins, polysaccharides, lipids. glycans, and small molecules (e.g. vitamins, primary and secondary metabolites, hormones, neurotransmitters). Amino acids may include moieties other than those found in the naturally occurring 20 amino acids (e.g. selenocysteine, pyrrolysine, carnitine, ornithine, GABA, and taurine). Amino acids may also include non-proteinogenic functional groups (e.g. $CF_3$, $N_3$, F, $NO_2$). Likewise, polypeptides and proteins may contain such amino acids. "Polysaccharides" include mono-, di-, and oligo-saccharides including O- and N-glycosyl-linkages. Polysaccharides may include functional group moieties not commonly found in a cellular environment (e.g. cyclopropene, halogens, and nitriles). Lipids include amphipathic-, phospho-, and glycollipids and sterols such as cholesterol. An "amphipathic lipid" refers to a lipid having hydrophilic and hydrophobic characteristics. A "phospholipid" refers to a lipid bound to a phosphate group and carries a charge. Exemplary phospholipids include phosphatidic acid, phosphatidylethanolamine, phosphatidylcholine, phosphatidylserine, and phosphatidylinositol. A "glycolipid" refers to a lipid bound to a poly- or oligo-saccharide. Exemplary glycolipids include galactolipids, sulfolipids, glycosphingolipids, and glycosylphosphatidylinositol. Lipids may include substituents not commonly found in the cellular environment (e.g. cyclopropene, halogens, and nitriles). A "small molecule" as used herein refers to any small molecule produced naturally in a biological environment and may contain unnatural moieties or linkages not typically found in a cell but tolerated during processing within a cell (e.g. cyclopropene, halogens, nitriles).

A "detectable moiety" as used herein refers to a moiety that can be covalently or noncovalently attached to a compound or biomolecule that can be detected for instance, using techniques known in the art. In embodiments, the detectable moiety is covalently attached. The detection moiety may provide for imaging of the attached compound or biomolecule. The detection moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, BODIPY, and cyanine dyes. Exemplary radionuclides include Fluorine-18, Gallium-68, and Copper-64. Exemplary magnetic contrast agents include gadolinium, iron oxide and iron platinum, and manganese.

A "water soluble moiety" as used herein refers to any moiety that enhances the water solubility of the compound or molecule to which it is bound. A water soluble moiety may alter the partitioning coefficient of a compound or molecule to which it is bound thereby making the molecule more or less hydrophilic. The more hydrophobic a compound, the higher its partition constant. The more hydrophilic a compound, the lower its partition constant. In some embodiments, the water soluble groups can decrease the partition constant of precursor molecules (which have a higher partition constant before attachment of the water soluble group) at least by about 10%, 20%, 30%, 40%, 50%, 60%, 70%, 80%, or 90%. In some embodiments, the water soluble groups described herein can decrease the partition constant of precursor molecules by 1-fold, 2-fold, 3-fold, 4-fold, or greater. Exemplary water soluble moieties include moieties such as poly(oxyethylated polyols) such as poly (oxyethylated glycerol), poly(oxyethylated sorbitol), and poly(oxyethylated glucose); poly(vinyl alcohol) ("PVA"); dextran; carbohydrate-based polymers and the like (including linear chains or branched chains); polyethylene glycol moieties of formula

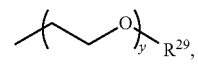

wherein y is an integer from 1 to 50 and $R^{29}$ is —OH or —OMe; polyvinylpyroolidone moieties; or poly 2-ethyl oxazoline moieties.

In some embodiments, the water soluble group can include a moiety containing a heteroatom (e.g., oxygen or nitrogen). In some embodiments to improve the water solubility of compounds herein a water soluble group is covalently attached at one or more positions. Such moieties include substituted alkyl moiety, substituted heteroalkyl moiety, substituted cycloalkyl moiety, substituted heteroalkyl moiety, or substituted aryl moiety. In embodiments, the moiety contains an alcohol moiety (an organic moiety having an —OH bound to a carbon atom), ester linker moiety (the linker moiety —C(O)O— between two carbon atoms), ether linker moiety (the linker moiety —O— between two carbon atoms), amine (—NH$_2$) moiety, nitrile (—CN) moiety, ketone moiety (the linker moiety —C(O)— between two carbon atoms), or aldehyde (—C(O)H) moiety.

II. Compositions

In a first aspect is a compound having the formula:

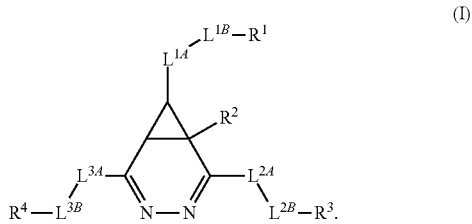

(I)

$L^{1A}$, $L^{1B}$, $L^{2A}$, $L^{2B}$, $L^{3A}$, and $L^{3B}$ are independently a bond, —C(O)—, —O—, —S—, —NH—, —NR$^5$—, —C(O)NR$^6$—, —S(O)$_n$—, —S(O)NR$^7$—, —OP(O)(OR$^8$)O—, substituted or unsubstituted alkylene, substituted or unsubstituted heteroalkylene, substituted or unsubstituted cycloalkylene, substituted or unsubstituted hetercycloalkylene, substituted or unsubstituted arylene-alkylene, substituted or unsubstituted arylene, or substituted or unsubstituted heteroarylene. $R^1$, $R^3$ and $R^4$ are independently hydrogen, halogen, —N$_3$, —CF$_3$, —CCl$_3$, —CBr$_3$, —Cl$_3$, —CN, —CHO, —OH, —NH, —NH$_2$, —COOH, —CONH$_2$, —NO$_2$, —S, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a detectable moiety, a water soluble moiety or a biomolecule. $R^2$ is $C_1$-$C_5$ substituted or unsubstituted alkyl. $R^5$, $R^6$, $R^7$, and $R^8$ are independently hydrogen, halogen, —N$_3$, —NO$_2$, —CF$_3$, —CCl$_3$, —CBr$_3$, —Cl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n is independently 1 or 2. In embodiments, -$L^{3A}L^{3B}$-$R^4$ is the same as -$L^{2A}$-$L^{2B}$-$R^3$. In embodiments, -$L^{3A}L^{3B}$-$R^4$ and -$L^{2A}$-$L^{2B}$-$R^3$ are different.

In embodiments, $L^{1A}$, $L^{1B}$, $L^{2B}$, and $L^{3B}$ are independently a bond, —C(O)—, —O—, —S—, —NH—, —NR$^5$—, —C(O)NR$^6$—, —S(O)$_n$—, —S(O)NR$^7$—, —OP(O)(OR$^8$)—, substituted or unsubstituted alkylene, substituted or unsubstituted heteroalkylene, substituted or unsubstituted cycloalkylene, substituted or unsubstituted hetercycloalkylene, substituted or unsubstituted arylene, or substituted or unsubstituted heteroarylene. $R^1$, $R^3$ and $R^4$ are independently hydrogen, halogen, —N$_3$, —CF$_3$, —CCl$_3$, —CBr$_3$, —Cl$_3$, —CN, —CHO, —OH, —NH, —NH$_2$, —COOH, —CONH$_2$, —NO$_2$, —S, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a detectable moiety, a water soluble moiety or a biomolecule. In related embodiments, $L^{2A}$ and $L^{3A}$ are independently a bond, —C(O)—, —O—, —S—, —NH—, —NR$^5$—, —C(O)NR$^6$—, —S(O)$_n$—, —S(O)NR$^7$—, —OP(O)(OR$^8$)O—, substituted or unsubstituted alkylene, substituted or unsubstituted heteroalkylene, substituted or unsubstituted cycloalkylene, substituted or unsubstituted hetercycloalkylene, substituted or unsubstituted arylene-alkylene, substituted or unsubstituted arylene, or substituted or unsubstituted heteroarylene. $R^1$, $R^3$ and $R^4$ are independently hydrogen, halogen, —N$_3$, —CF$_3$, —CCl$_3$, —CBr$_3$, —Cl$_3$, —CN, CHO, —OH, —NH, —NH$_2$, —COOH, —CONH$_2$, —NO$_2$, —S, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a detectable moiety, a water soluble moiety or a biomolecule moiety.

In certain embodiments of the compounds provided herein, $L^{1A}$ may independently be a bond, —C(O)—, —O—, —S—, —NH—, —NR$^5$—, —C(O)NR$^6$—, —S(O)$_n$—, —S(O)NR$^7$—, —OP(O)(OR$^8$)O—, $R^{1Aa}$-substituted or unsubstituted alkylene, $R^{1Aa}$-substituted or unsubstituted heteroalkylene, $R^{1Aa}$-substituted or unsubstituted cycloalkylene, $R^{1Aa}$-substituted or unsubstituted heterocycloalkylene, $R^{1Aa}$-substituted or unsubstituted arylene, or $R^{1Aa}$-substituted or unsubstituted heteroarylene. In embodiments, $R^5$, $R^6$, $R^7$ and $R^8$ are hydrogen.

$R^{1Aa}$ is independently hydrogen, halogen, —N$_3$, —NO$_2$, —CF$_3$, —CCl$_3$, —CBr$_3$, —Cl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, $R^{1Ab}$-substituted or unsubstituted alkyl, $R^{1Ab}$-substituted or unsubstituted heteroalkyl, $R^{1Ab}$-substituted or unsubstituted cycloalkyl, $R^{1Ab}$-substituted or unsubstituted heterocycloalkyl, $R^{1Ab}$-substituted or unsubstituted aryl, or $R^{1Ab}$-substituted or unsubstituted heteroaryl.

$R^{1Ab}$ is hydrogen, halogen, —N$_3$, —NO$_2$, —CF$_3$, —CCl$_3$, —CBr$_3$, —Cl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, unsubstituted alkyl, unsubstituted heteroalkyl, unsubstituted cycloalkyl, unsubstituted heterocycloalkyl, unsubstituted aryl, or unsubstituted heteroaryl.

In certain embodiments of the compounds provided herein, $L^{1B}$ may independently be a bond, —C(O)—, —O—, —S—, —NH—, —NR$^5$—, —C(O)NR$^6$—, —S(O)$_n$—, —S(O)NR$^7$—, —OP(O)(OR$^8$)O—, $R^{1Ba}$-substituted or unsubstituted alkylene, $R^{1Ba}$-substituted or unsubstituted heteroalkylene, $R^{1Ba}$-substituted or unsubstituted cycloalkylene, $R^{1Ba}$-substituted or unsubstituted heterocycloalkylene, $R^{1Ba}$-substituted or unsubstituted arylene, or $R^{1Ba}$-substituted or unsubstituted heteroarylene. In embodiments, $R^5$, $R^6$, $R^7$ and $R^8$ are hydrogen.

$R^{1Ba}$ is independently hydrogen, halogen, —N$_3$, —NO$_2$, —CF$_3$, —CCl$_3$, —CBr$_3$, —Cl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, $R^{1Bb}$-substituted or unsubstituted alkyl, $R^{1Bb}$-substituted or unsubstituted heteroalkyl, $R^{1Bb}$-substituted or unsubstituted cycloalkyl, $R^{1Bb}$-substituted or unsubstituted heterocycloalkyl, $R^{1Bb}$-substituted or unsubstituted aryl, or $R^{1Bb}$-substituted or unsubstituted heteroaryl.

$R^{1Bb}$ is hydrogen, halogen, —$N_3$, —$NO_2$, —$CF_3$, —$CCl_3$, —$CBr_3$, —$Cl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$OCH_3$, —NHC-NHNH$_2$, unsubstituted alkyl, unsubstituted heteroalkyl, unsubstituted cycloalkyl, unsubstituted heterocycloalkyl, unsubstituted aryl, or unsubstituted heteroaryl.

In certain embodiments of the compounds provided herein, $L^{2A}$ may independently be a bond, —C(O)—, —O—, —S—, —NH—, —$NR^5$—, —$C(O)NR^6$—, —$S(O)_n$—, —$S(O)NR^7$—, —$OP(O)(OR^8)O$—, $R^{2Aa}$-substituted or unsubstituted alkylene, $R^{2Aa}$-substituted or unsubstituted heteroalkylene, $R^{2Aa}$-substituted or unsubstituted cycloalkylene, $R^{2Aa}$-substituted or unsubstituted heterocycloalkylene, $R^{2Aa}$-substituted or unsubstituted arylene, or $R^{2Aa}$-substituted or unsubstituted heteroarylene. In embodiments, $R^5$, $R^6$, $R^7$ and $R^8$ are hydrogen.

$R^{2Aa}$ is independently hydrogen, halogen, —$N_3$, —$NO_2$, —$CF_3$, —$CCl_3$, —$CBr_3$, —$Cl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$OCH_3$, —NHCNHNH$_2$, $R^{2Ab}$-substituted or unsubstituted alkyl, $R^{2Ab}$-substituted or unsubstituted heteroalkyl, $R^{2Ab}$-substituted or unsubstituted cycloalkyl, $R^{2Ab}$-substituted or unsubstituted heterocycloalkyl, $R^{2Ab}$-substituted or unsubstituted aryl, or $R^{2Ab}$-substituted or unsubstituted heteroaryl.

$R^{2Ab}$ is hydrogen, halogen, —$N_3$, —$NO_2$, —$CF_3$, —$CCl_3$, —$CBr_3$, —$Cl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$OCH_3$, —NHC-NHNH$_2$, unsubstituted alkyl, unsubstituted heteroalkyl, unsubstituted cycloalkyl, unsubstituted heterocycloalkyl, unsubstituted aryl, or unsubstituted heteroaryl.

In certain embodiments of the compounds provided herein, $L^{2B}$ may independently be a bond, —C(O)—, —O—, —S—, —NH—, —$NR^5$—, —$C(O)NR^6$—, —$S(O)_n$—, —$S(O)NR^7$—, —$OP(O)(OR^8)O$—, $R^{2Ba}$-substituted or unsubstituted alkylene, $R^{2Ba}$-substituted or unsubstituted heteroalkylene, $R^{2Ba}$-substituted or unsubstituted cycloalkylene, $R^{2Ba}$-substituted or unsubstituted heterocycloalkylene, $R^{2Ba}$-substituted substituted or unsubstituted arylene, or $R^{2Ba}$-substituted or unsubstituted heteroarylene. In embodiments, $R^5$, $R^6$, $R^7$ and $R^8$ are hydrogen.

$R^{2Ba}$ is independently hydrogen, halogen, —$N_3$, —$NO_2$, —$CF_3$, —$CCl_3$, —$CBr_3$, —$Cl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$OCH_3$, —NHCNHNH$_2$, $R^{2Bb}$-substituted or unsubstituted alkyl, $R^{2Bb}$-substituted or unsubstituted heteroalkyl, $R^{2Bb}$-substituted or unsubstituted cycloalkyl, $R^{2Bb}$-substituted or unsubstituted heterocycloalkyl, $R^{2Bb}$-substituted or unsubstituted aryl, or $R^{2Bb}$-substituted or unsubstituted heteroaryl.

$R^{2Bb}$ is hydrogen, halogen, —$N_3$, —$NO_2$, —$CF_3$, —$CCl_3$, —$CBr_3$, —$Cl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$OCH_3$, —NHC-NHNH$_2$ unsubstituted alkyl, unsubstituted heteroalkyl, unsubstituted cycloalkyl, unsubstituted heterocycloalkyl, unsubstituted aryl, or unsubstituted heteroaryl.

$L^{1A}$ and $L^{1B}$ may independently be unsubstituted alkylene, unsubstituted heteroalkylene, —O—, —NH— or —$OP(O)(OR^8)O$—. When $L^{1A}$ is —CHCH—, $L^{1B}$ may be unsubstituted alkylene, heteroalkylene, —O—, —NH—, or —$OP(O)(OR^8)O$—, wherein $R^8$ is unsubstituted $C_1$-$C_5$ alkyl or unsubstituted 2 to 5 membered heteroalkyl. When $L^{1A}$ is —$CH_2NH$—, $L^{1B}$ may be unsubstituted alkylene, heteroalkylene, —O—, —NH—, or —$OP(O)(OR^8)O$—, wherein $R^8$ is unsubstituted $C_1$-$C_5$ alkyl or unsubstituted 2 to 5 membered heteroalkyl. When $L^{1A}$ is —$CH_2O$—, $L^{1B}$ may be unsubstituted alkylene, heteroalkylene, —O—, —NH—, or —$OP(O)(OR^8)O$—, wherein $R^8$ is unsubstituted $C_1$-$C_5$ alkyl or unsubstituted 2 to 5 membered heteroalkyl. When $L^{1A}$ is —C(O)—, $L^{1B}$ may be unsubstituted alkylene, heteroalkylene, —O—, —NH—, or —$OP(O)(OR^8)O$—, wherein $R^8$ is unsubstituted $C_1$-$C_5$ alkyl or unsubstituted 2 to 5 membered heteroalkyl.

$L^{2A}$ and $L^{2B}$ may independently be —O—, —NH—, substituted or unsubstituted alkylene, substituted or unsubstituted heteroalkylene, unsubstituted arylene, or substituted or unsubstituted heteroarylene. $L^{2A}$ may be $C_1$-$C_5$ unsubstituted alkylene, 2 to 5 membered unsubstituted heteroalkylene, or 5 to 6 membered unsubstituted heteroarylene. $L^{2A}$ may be phenylene, 4-substituted phenylene, or unsubstituted phenylene-methylene. $L^{2B}$ may be $C_1$-$C_5$ unsubstituted alkylene, or 2 to 5 membered unsubstituted heteroalkylene.

When $L^{2A}$ is unsubstituted alkylene, $L^{2B}$ may be unsubstituted alkylene, unsubstituted heteroalkylene, —O—, —NH—, or —$OP(O)(OR^8)O$—, wherein $R^8$ is unsubstituted $C_1$-$C_5$ alkyl or unsubstituted 2 to 5 membered heteroalkyl. When $L^{2A}$ is unsubstituted heteroalkylene, $L^{2B}$ may be unsubstituted alkylene, unsubstituted heteroalkylene, —O—, —NH—, or —$OP(O)(OR^8)O$—, wherein $R^8$ is unsubstituted $C_1$-$C_5$ alkyl or unsubstituted 2 to 5 membered heteroalkyl. When $L^{2A}$ is unsubstituted arylene, $L^{2B}$ may be unsubstituted alkylene, unsubstituted heteroalkylene, —O—, —NH—, or —$OP(O)(OR^8)O$—, wherein $R^8$ is unsubstituted $C_1$-$C_5$ alkyl or unsubstituted 2 to 5 membered unsubstituted heteroalkyl. When $L^{2A}$ is unsubstituted heteroarylene, $L^{2B}$ may be unsubstituted alkylene, unsubstituted heteroalkylene, —O—, —NH—, or —$OP(O)(OR^8)$ O—, wherein $R^8$ is unsubstituted $C_1$-$C_5$ alkyl or unsubstituted 2 to 5 membered heteroalkyl. When $L^{2A}$ is —$CH_2(C_6H_6)O$—, $L^{2B}$ may be unsubstituted heteroalkylene, —O—, or —$OP(O)(OR^8)O$—, wherein $R^8$ is unsubstituted $C_1$-$C_5$ alkyl or unsubstituted 2 to 5 membered heteroalkyl.

$L^{2A}$ may be unsubstituted alkylene or unsubstituted heteroalkylene. $L^{2A}$ may be —$(CH_2)_{x1}$—NH—C(O)—$(CH_2)_{x2}$—C(O)—NH—$(CH_2)_{x3}$— where x1, x2, and x3 are independently 2-6. In certain embodiments x1 is 1. In certain embodiments x2 is 3. In certain embodiments x3 is 6. $L^{2B}$ may be unsubstituted alkylene, unsubstituted heteroalkylene, or —$OP(O)(OR^8)O$—, wherein $R^8$ is unsubstituted alkyl or unsubstituted heteroalkyl. $R^8$ may be a $C_1$-$C_6$ unsubstituted alkyl. $R^8$ may be a $C_6$ unsubstituted alkyl.

$L^{1A}$ may be unsubstituted alkylene or unsubstituted heteroalkylene. $L^{1A}$ may be a $C_1$-$C_5$ alkylene or a 2 to 5 membered heteroalkylene. In some embodiments, $L^{1A}$ is the alkylene or heteroalkylene shown in Table 2. $L^{1B}$ may be unsubstituted alkylene, unsubstituted heteroalkylene, or —$OP(O)(OR^8)O$—, wherein $R^8$ is a unsubstituted alkyl or unsubstituted heteroalkyl.

In certain embodiments of the compounds provided herein, $L^{3A}$ may independently be a bond, —C(O)—, —O—, —S—, —NH—, —NR—, —$C(O)NR^6$—, —$S(O)_n$—, —$S(O)NR^7$—, —$OP(O)(OR^8)O$—, $R^{3Aa}$-substituted or unsubstituted alkylene, $R^{3Aa}$-substituted or unsubstituted heteroalkylene, $R^{3Aa}$-substituted or unsubstituted cycloalkylene, $R^{3Aa}$-substituted or unsubstituted heterocycloalkylene, $R^{3Aa}$-substituted or unsubstituted arylene, or $R^{3Aa}$-substituted or unsubstituted heteroarylene. In embodiments, $R^5$, $R^6$, $R^7$ and $R^8$ are hydrogen.

$R^{3Aa}$ is independently hydrogen, halogen, —$N_3$, —$NO_2$, —$CF_3$, —$CCl_3$, —$CBr_3$, —$Cl_3$, —CN, —OH, —$NH_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, R$^{3Ab}$-substituted or unsubstituted alkyl, R$^{3Ab}$-substituted or unsubstituted heteroalkyl, R$^{3Ab}$-substituted or unsubstituted cycloalkyl, R$^{3Ab}$-substituted or unsubstituted heterocycloalkyl, R$^{3Ab}$-substituted or unsubstituted aryl, or R$^{3Ab}$-substituted or unsubstituted heteroaryl.

R$^{3Ab}$ is hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$ unsubstituted alkyl, unsubstituted heteroalkyl, unsubstituted cycloalkyl, unsubstituted heterocycloalkyl, unsubstituted aryl, or unsubstituted heteroaryl.

In certain embodiments of the compounds provided herein, L$^{3B}$ may independently be a bond, —C(O)—, —O—, —S—, —NH—, —NR$^5$—, —C(O)NR$^6$—, —S(O)$_n$—, —S(O)NR$^7$—, —OP(O)(OR$^8$)O—, R$^{3Ba}$-substituted or unsubstituted alkylene, R$^{3Ba}$-substituted or unsubstituted heteroalkylene, R$^{3Ba}$-substituted or unsubstituted cycloalkylene, R$^{3Ba}$-substituted or unsubstituted heterocycloalkylene, R$^{3Ba}$-substituted or unsubstituted arylene, or R$^{3Ba}$-substituted or unsubstituted heteroarylene. In embodiments, R$^5$, R$^6$, R$^7$ and R$^8$ are hydrogen.

R$^{3Ba}$ is independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, R$^{3Bb}$-substituted or unsubstituted alkyl, R$^{3Bb}$-substituted or unsubstituted heteroalkyl, R$^{3Bb}$-substituted or unsubstituted cycloalkyl, R$^{3Bb}$-substituted or unsubstituted heterocycloalkyl, R$^{3Bb}$-substituted or unsubstituted aryl, or R$^{3Bb}$-substituted or unsubstituted heteroaryl.

R$^{3Bb}$ is hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$ unsubstituted alkyl, unsubstituted heteroalkyl, unsubstituted cycloalkyl, unsubstituted heterocycloalkyl, unsubstituted aryl, or unsubstituted heteroaryl.

In certain embodiments of the compounds provided herein, R$^1$ may be hydrogen, halogen, —N$_3$, —CF$_3$, —CCl$_3$, —CBr$_3$, —CI$_3$, —CN, —CHO, —OH, —NH, —NH$_2$, —COOH, —CONH$_2$, —NO$_2$, —S, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, R$^{1a}$-substituted or unsubstituted alkyl, R$^{1a}$-substituted or unsubstituted heteroalkyl, R$^{1a}$-substituted or unsubstituted cycloalkyl, R$^{1a}$-substituted or unsubstituted heterocycloalkyl, R$^{1a}$-substituted or unsubstituted aryl, R$^{1a}$-substituted or unsubstituted heteroaryl, a detectable moiety, a water soluble moiety or a biomolecule moiety.

R$^{1a}$ is hydrogen, halogen, —N$_3$, —CF$_3$, —CCl$_3$, —CBr$_3$, —CI$_3$, —CN, —CHO, —OH, —NH, —NH$_2$, —COOH, —CONH$_2$, —NO$_2$, —S, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, R$^{1b}$-substituted or unsubstituted alkyl, R$^{1b}$-substituted or unsubstituted heteroalkyl, R$^{1b}$-substituted or unsubstituted cycloalkyl, R$^{1b}$-substituted or unsubstituted heterocycloalkyl, R$^{1b}$-substituted or unsubstituted aryl, R$^{1b}$-substituted or unsubstituted heteroaryl, a detectable moiety, a water soluble moiety or a biomolecule moiety.

R$^{1b}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

R$^1$ may be hydrogen, halogen, —OH, —NH$_2$, —COOH, substituted or unsubstituted alkyl, a biomolecule moiety, a detectable moiety, or a water soluble moiety. R$^1$ may be —OH. R$^1$ may be a biomolecule moiety. R$^1$ may be a detectable moiety. R$^2$ may be methyl, ethyl, or propyl. R$^2$ may be methyl.

In certain embodiments of the compounds provided herein, R$^3$ may be hydrogen, halogen, —N$_3$, —CF$_3$, —CCl$_3$, —CBr$_3$, —CI$_3$, —CN, —CHO, —OH, —NH, —NH$_2$, —COOH, —CONH$_2$, —NO$_2$, —S, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, R$^{3a}$-substituted or unsubstituted alkyl, R$^{3a}$-substituted or unsubstituted heteroalkyl, R$^{3a}$-substituted or unsubstituted cycloalkyl, R$^{3a}$-substituted or unsubstituted heterocycloalkyl, R$^{3a}$-substituted or unsubstituted aryl, R$^{3a}$-substituted or unsubstituted heteroaryl, a detectable moiety, a water soluble moiety or a biomolecule moiety.

R$^{3a}$ is hydrogen, halogen, —N$_3$, —CF$_3$, —CCl$_3$, —CBr$_3$, —CI$_3$, —CN, —CHO, —OH, —NH, —NH$_2$, —COOH, —CONH$_2$, —NO$_2$, —S, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, R$^{3b}$-substituted or unsubstituted alkyl, R$^{3b}$-substituted or unsubstituted heteroalkyl, R$^{3b}$-substituted or unsubstituted cycloalkyl, R$^{3b}$-substituted or unsubstituted heterocycloalkyl, R$^{3b}$-substituted or unsubstituted aryl, R$^{3b}$-substituted or unsubstituted heteroaryl, a detectable moiety, a water soluble moiety or a biomolecule moiety.

R$^{3b}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

In certain embodiments of the compounds provided herein, R$^4$ may be hydrogen, halogen, —N$_3$, —CF$_3$, —CCl$_3$, —CBr$_3$, —CI$_3$, —CN, —CHO, —OH, —NH, —NH$_2$, —COOH, —CONH$_2$, —NO$_2$, —S, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, R$^{4a}$-substituted or unsubstituted alkyl, R$^{4a}$-substituted or unsubstituted heteroalkyl, R$^{4a}$-substituted or unsubstituted cycloalkyl, R$^{4a}$-substituted or unsubstituted heterocycloalkyl, R$^{4a}$-substituted or unsubstituted aryl, R$^{4a}$-substituted or unsubstituted heteroaryl, a detectable moiety, a water soluble moiety or a biomolecule moiety.

R$^{4a}$ is hydrogen, halogen, —N$_3$, —CF$_3$, —CCl$_3$, —CBr$_3$, —CI$_3$, —CN, —CHO, —OH, —NH, —NH$_2$, —COOH, —CONH$_2$, —NO$_2$, —S, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, R$^{4b}$-substituted or unsubstituted alkyl, R$^{4b}$-substituted or unsubstituted heteroalkyl, R$^{4b}$-substituted or unsubstituted cycloalkyl, R$^{4b}$-substituted or unsubstituted heterocycloalkyl, R$^{4b}$-substituted or unsubstituted aryl, R$^{4b}$-substituted or unsubstituted heteroaryl, a detectable moiety, a water soluble moiety or a biomolecule moiety.

R$^{4b}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, R$^3$ and R$^4$ are independently hydrogen, halogen, —OH, —NH$_2$, —COOH, substituted or unsubstituted alkyl, substituted or unsubstituted heteroalkyl, substituted or unsubstituted cycloalkyl, substituted or unsubstituted aryl, substituted or unsubstituted heteroaryl, a detectable moiety, a water soluble moiety or a biomolecule moiety, a detectable moiety, a water soluble moiety or a biomolecule. $R^3$ may be hydrogen, halogen, —OH, $C_1$-$C_5$ unsubstituted alkyl, or $C_5$-$C_6$ unsubstituted aryl. $R^3$ may be a biomolecule moiety. $R^3$ may be a detectable moiety. $R^3$ may be a water soluble moiety. $R^4$ may be hydrogen, unsubstituted alkyl, unsubstituted heteroalkyl, unsubstituted aryl, unsubstituted heteroaryl, a detectable moiety, a water soluble moiety or a biomolecule. $R^4$ may be hydrogen or methyl. $R^4$ may be hydrogen. $R^4$ may be methyl. $R^4$ may be a biomolecule moiety. $R^4$ may be a detectable moiety. $R^4$ may be a water soluble moiety.

When one or more of $R^1$, $R^3$, or $R^4$ is a detectable moiety, the detectable moiety may be a fluorophore, antibody, reactive dye, radio-labeled moiety, magnetic contrast agent, or quantum dot. The detectable moiety may be a fluorophore, a radionuclide, or a magnetic contrast agent. The detectable moiety may be fluorescein, BODIPY, or a cyanine dye. The detectable moiety may be Fluorine-18, Gallium-68, or Copper-64. The detectable moiety may be gadolinium, iron oxide, iron platinum, manganese, or a paramagnetic species. The detectable moiety may be attached to a biomolecule. The detectable moiety may be a biomolecule such as GFP or luciferase.

When one or more of $R^1$, $R^3$, or $R^4$ is a biomolecule moiety, the biomolecule (i.e. biomolecule moiety) may be a nucleic acid (e.g. a nucleotide or polynucleotide), an amino acid, a polypeptide, a protein, a lipid, a polysaccharide, or a small molecule such as a vitamin, a metabolite, a sterol, a hormone, or a neurotransmitter. One or more of $R^1$, $R^3$ or $R^4$ may be a biomolecule. When the biomolecule moiety is a nucleic acid (e.g. nucleotide or polynucleotide), the biomolecule may be a RNA moiety, including but not limited to mRNA moiety, tRNA moiety, rRNA moiety, miRNA moiety, siRNA moiety, snRNA moiety, or snoRNA moiety. The biomolecule may be a DNA moiety. The DNA may be linear or helical. The biomolecule moiety may be a synthetically derived RNA moiety or DNA moiety. The biomolecule moiety may be a RNA moiety or DNA moiety isolated from a source prior to attaching to the diazonorcaradiene compound. In certain embodiments the RNA moiety or DNA moiety includes a detectable moiety.

The biomolecule moiety may be an amino acid moiety, a polypeptide moiety or a protein moiety. When the biomolecule moiety is an amino acid, the amino acid may be a naturally occurring amino acid or an amino acid analogue. When the biomolecule moiety is a polypeptide, the polypeptide may be linear or may have secondary, tertiary, or quaternary structure. Likewise, when the biomolecule moiety is a protein, the protein may exhibit secondary, tertiary, or quaternary structure. The protein may be folded or unfolded. The protein may have activity. In certain embodiments, the amino acid, polypeptide, or protein includes a detectable moiety.

The biomolecule moiety may be a lipid moiety. The lipid may be an amphipathic lipid moiety, a phospholipid moiety, a glycolipid moiety, or a sterol moiety. The lipid may be a glycolipid moiety. The lipid moiety may be a phospholipid moiety such as phosphatidylethanolamine moiety, phosphatidylcholine moiety, phosphatidylserine moiety, or phosphatidylinositol moiety. The lipid moiety may be a choline phospholipid moiety. $R^1$ may be a lipid moiety. $R^1$ may be a phospholipid moiety or a glycolipid moiety. The lipid moiety may be a glycolipid moiety such as a glycosphingolipid moiety. In certain embodiments, the lipid includes a detectable moiety.

The biomolecule moiety may be a carbohydrate moiety such as a saccharide moiety. The saccharide moiety may be a mono-, di-, poly-, or oligo-saccharide moiety. The biomolecule moiety may be a glycan moiety. The biomolecule may be an hexosamine moiety such as mannosamine moiety, galactosamine moiety, or glucosamine moiety. Thus, $R^1$ may be a saccharide moiety or an amino-sugar moiety.

The biomolecule moiety may be a small molecule moiety such as a vitamin moiety or hormone moiety that can be labeled with a compound of formula (II) or formula (III). R', $R^3$, and $R^4$ may be a small molecule as described herein.

When one or more of $R^1$, $R^3$, or $R^4$ is a water soluble moiety, the water soluble moiety may be a charged or charge-neutral moiety as defined herein, that enhances the water solubility of the compound. The water soluble moiety may be a compound moiety or biomolecule moiety, as defined herein, that enhances the water solubility of the compound. The water soluble moiety may alter the partitioning coefficient of the compound thereby altering the hydrophilicity or hydrophobicity of the compound. One or more of $R^1$, $R^3$, or $R^4$ may be a water soluble moiety.

In another aspect is a compound having the formula:

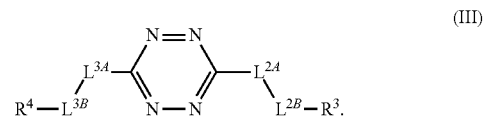

(III)

$L^{2A}$, $L^{2B}$, $L^{3A}$, $L^{3B}$, $R^3$, and $R^4$ are as defined herein, including embodiments thereof.

The compound of formula (III) may have the formula:

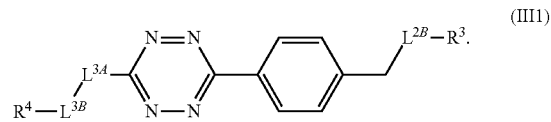

(III1)

$R^4$, $L^{2B}$, $L^{3A}$, $L^{3B}$, and $R^3$ are as defined above. $R^4$ may be hydrogen, methyl, a biomolecule, a detectable moiety, or a water soluble moiety. $R^4$ may be methyl. $R^4$ may be hydrogen. $R^3$ may be hydrogen, a biomolecule, a detectable moiety, or a water soluble moiety. $R^3$ may be a biomolecule. $R^3$ may be a detectable moiety.

The compound of formula (III) may include one or more of the compounds set forth in Table 1.

In another aspect is a compound having the formula:

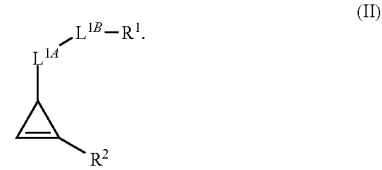

(II)

$L^{1A}$, $L^{1B}$, $R^1$, and $R^2$ are as defined herein, including embodiments thereof.

The compound of formula (II) may have the formula:

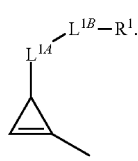
(III)

$L^{1A}$, $L^{1B}$ and $R^1$ are as described herein, including embodiments thereof.

The compound of formula (II) may have the formula:

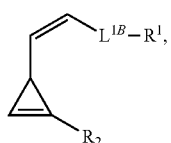
(IV)

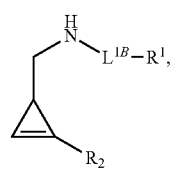
(V)

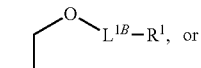
(VI)

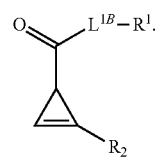
(VII)

$L^{1B}$ and $R^1$ are as described herein, including embodiments thereof.

The compound of formula (II) may have the formula:

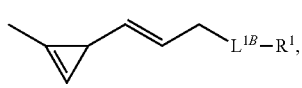
(IV1)

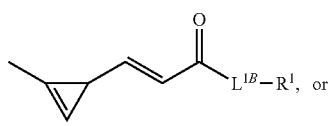
(IV2)

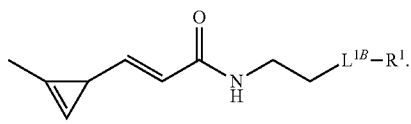
(IV3)

$L^{1B}$ and $R^1$ are as described herein, including embodiments thereof. $R^1$ may be hydrogen, a biomolecule, a detectable moiety, or a water soluble moiety.

The compound of formula (II) may have formula:

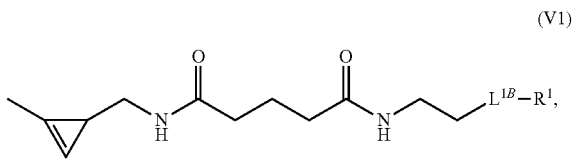
(V1)

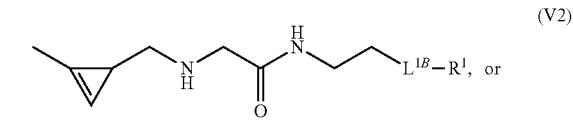
(V2)

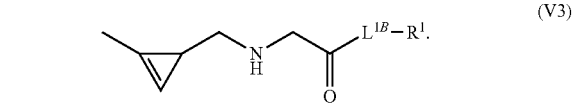
(V3)

$L^{1B}$ and $R^1$ are as described herein, including embodiments thereof. $R^1$ may be hydrogen, a biomolecule, a detectable moiety, or a water soluble moiety.

The compound of formula (II) may have the formula:

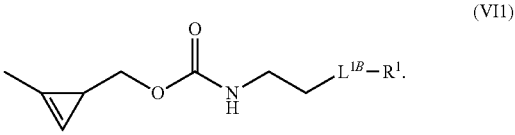
(VI1)

$L^{1B}$ and $R^1$ are as described herein, including embodiments thereof. $R^1$ may be hydrogen, a biomolecule, a detectable moiety, or a water soluble moiety.

The compound of formula (II) may have the formula:

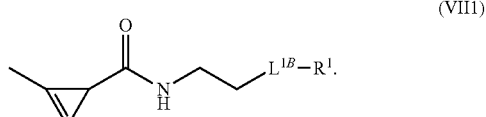
(VII1)

$L^{1B}$ and $R^1$ are as described herein, including embodiments thereof. $R^1$ may be hydrogen, a biomolecule, a detectable moiety, or a water soluble moiety.

The compound of formula (II) may have formula set forth in Table 2.

TABLE 2

| Formula (II) exemplary compounds. | |
|---|---|
| entry | cyclopropene |
| I1 | 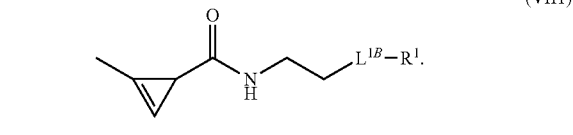 |
| IV2 | |

TABLE 2-continued

Formula (II) exemplary compounds.

| entry | cyclopropene |
|---|---|
| IV3 | 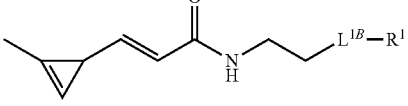 |
| V1 | 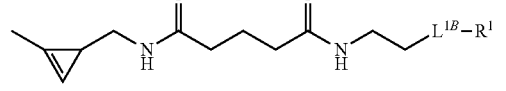 |
| V2 | 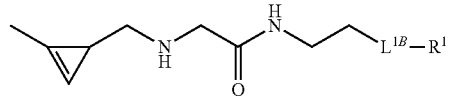 |
| V3 | 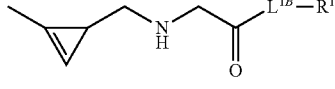 |
| VI1 | 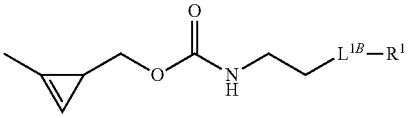 |
| VII1 | 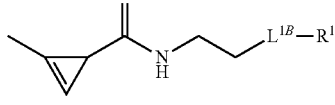 |

In Table 2, $L^{1B}$ and $R^1$ are as defined herein, including embodiments thereof. $L^{1B}$ may be a bond, unsubstituted alkylene, heteroalkylene, —O—, —NH— or —OP(O)(OR$^8$)O—. $R^1$ may be hydrogen, a biomolecule, a detectable moiety, or a water soluble moiety. In embodiments, $L^{1B}$ is a bond.

In another aspect is a compound having the formula:

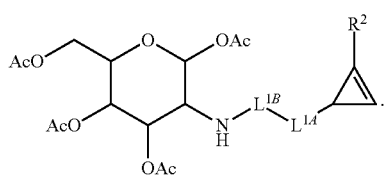

(VIII)

$L^{1A}$, $L^{1B}$ and $R^2$ are as described herein, including embodiments thereof. $L^{1A}$ and $L^{1B}$ may independently a bond, —C(O)—, —O—, —S—, —NR$^5$—, —C(O)NR$^6$—, —S(O)$_n$—, —S(O)NR$^7$—, —OP(O)(OR$^8$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^5$, $R^6$, $R^7$, and $R^8$ may independently be hydrogen. $R^8$ may be $C_1$-$C_5$ unsubstituted alkyl, 2 to 5 membered heteroalkyl, or 5 to 6 membered aryl. In embodiments, $L^{1B}$ is a bond. $R^2$ may be $C_1$-$C_5$ substituted or unsubstituted alkyl.

$R^2$ may be methyl, ethyl, or propyl. $R^2$ may be methyl.

The compound of formula (VIII) may have the formula:

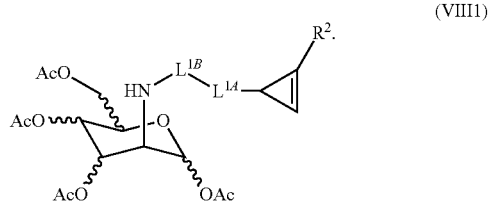

(VIII1)

In formula VIII1, $L^{1A}$, $L^{1B}$ and $R^2$ are as described herein, including embodiments thereof.

The compound of formula (VIII) may have formula:

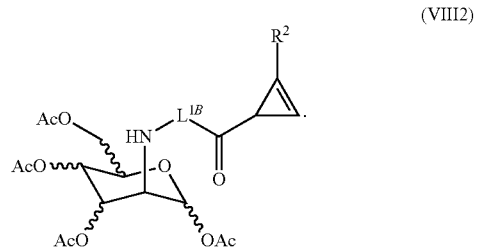

(VIII2)

$L^{1B}$ and $R^2$ are as described herein, including embodiments thereof.

The compound of formula (VIII) may have the formula:

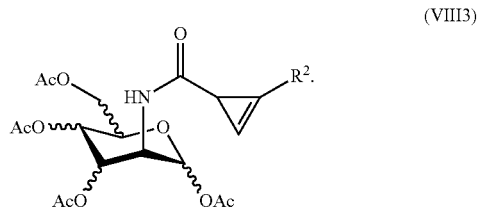

(VIII3)

$R^2$ is as described herein, including embodiments thereof.

The compound of formula (VIII) may have the formula:

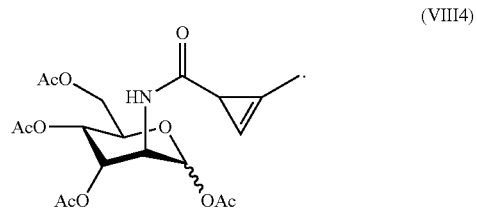

(VIII4)

III. Methods of Synthesizing Tetrazine

In another aspect a method of synthesizing a 3,6-disubstituted 1,2,4,5-tetrazine is provided. The method includes combining in a reaction vessel (i.e. a contained volume that allows for reactants to sufficiently contact to react and form one or more chemical products) a first substituted nitrile having the formula

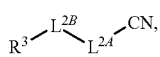

a second nitrile having the formula

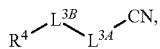

hydrazine and a Lewis Acid catalyst thereby forming a tetrazine of formula

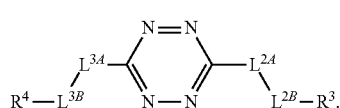

(III)

In embodiments, -$L^{3A}L^{3B}$-$R^4$ is the same as -$L^{2A}$-$L^{2B}$-$R^3$. In embodiments, -$L^{3A}$-$L^{3B}$-$R^4$ and -$L^{2A}$-$L^{2B}$-$R^3$ are different.

The first substituted nitrile and/or the second substituted nitrile may be an unactivated substituted nitrile such as acetonitrile. The method may include synthesizing an unsymmetric tetrazine (i.e. where -$L^{3A}$-$L^{3B}$-$R^4$ and -$L^{2A}$-$L^{2B}$-$R^3$ are different). The method may include synthesizing a symmetric tetrazine (i.e. where -$L^{3A}$-$L^{3B}$-$R^4$ and -$L^{2A}$-$L^{2B}$-$R^3$ are the same).

The Lewis acid catalyst may be a metal such as Zn, Mg, Cu, Mn, Co, Yb, Sc, or Ni. Such metals may exist as metal salts. The metal salt may be a metal triflate such as $Zn(OTf)_2$, $Cu(OTf)_2$, or $Ni(OTf)_2$. The metal salt may include anions such as Cl, Br, or I (e.g. $ZnCl_2$, $ZnBr_2$, $ZnI_2$, $NiCl_2$, $NiBr_2$, or $NiI_2$). The Lewis acid catalyst may be Zn or Ni. The catalyst may be a Zn or Ni salt. The synthesized 3,6-disubstituted 1,2,4,5-tetrazine may be one or more of the compounds set forth in Table 1.

TABLE 1

Synthesis of exemplary 1,2,4,5-tetrazine compounds:

| Entry | R1 | R2 | Catalyst | Product | Yield (%) |
|---|---|---|---|---|---|
| 1 | benzyl | benzyl | Ni | 3,6-dibenzyl-1,2,4,5-tetrazine | 95 |
| 2 | n-hexyl | n-hexyl | Zn | 3,6-di(n-C$_5$H$_{11}$)-1,2,4,5-tetrazine | 59 |
| 3 | neopentyl | neopentyl | Zn | 3,6-di-tert-butylmethyl-1,2,4,5-tetrazine | 24 |
| 4 | BocHN-CH$_2$- | BocHN-CH$_2$- | Zn | 3,6-bis(BocHN-CH$_2$-)-1,2,4,5-tetrazine | 32 |
| 5[b] | N-Boc-pyrrol-2-ylmethyl | H$_3$C- | Ni | 3-(pyrrol-2-yl)-6-methyl-1,2,4,5-tetrazine | 58 |
| 6 | 4-(BocHNCH$_2$)phenyl | H$_3$C- | Ni | 3-(4-(BocHNCH$_2$)phenyl)-6-methyl-1,2,4,5-tetrazine | 68 |
| 7 | 4-(HOCH$_2$)phenyl | H$_3$C- | Ni | 3-(4-(HOCH$_2$)phenyl)-6-methyl-1,2,4,5-tetrazine | 66 |
| 8 | 4-iodophenyl | H$_3$C- | Ni | 3-(4-iodophenyl)-6-methyl-1,2,4,5-tetrazine | 41 |

TABLE 1-continued

Synthesis of exemplary 1,2,4,5-tetrazine compounds:

| Entry | R1 | R2 | Catalyst | Product | Yield (%) |
|---|---|---|---|---|---|
| 9 | HO-C6H4- | H3C- | Zn | 3-(4-hydroxyphenyl)-6-methyl-1,2,4,5-tetrazine | 43 |
| 10 | HOOC-CH2-C6H4- | H3C- | Ni | 4-(6-methyl-1,2,4,5-tetrazin-3-yl)phenylacetic acid | 70 |
| 11 | PhCH2- | H3C- | Zn | 3-benzyl-6-methyl-1,2,4,5-tetrazine | 40 |
| 12[c] | HO-CH2CH2- | H3C- | Zn | 3-(2-hydroxyethyl)-6-methyl-1,2,4,5-tetrazine | 36 |
| 13 | BocHN-CH2- | H3C- | Ni | 3-(BocNHCH2)-6-methyl-1,2,4,5-tetrazine | 36 |
| 14 | n-C5H11- | H3C- | Zn | 3-n-pentyl-6-methyl-1,2,4,5-tetrazine | 40 |
| 15 | n-C5H11- | PhCH2- | Zn | 3-benzyl-6-n-pentyl-1,2,4,5-tetrazine | 12 |
| 16 | HO-CH2-C6H4- | (CH3)3Si- | Zn | 3-(4-hydroxymethylphenyl)-1,2,4,5-tetrazine | 30 |

IV. Methods for Synthesizing Diazonorcaradiene

In another aspect, a method for synthesizing a diazonorcaradiene is provided. The method includes contacting a compound of formula

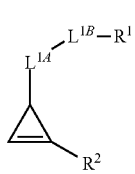

(II)

with a compound of formula

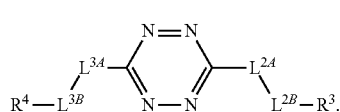

(III)

A diazonorcaradiene of the formula

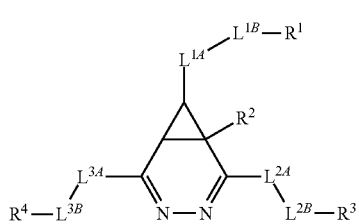

(I)

is thereby formed.

$R^1$, $R^2$, $R^3$, $R^4$, $L^{1A}$, $L^{1B}$, $L^{2A}$, $L^{2B}$, $L^{3A}$, and $L^{3B}$ are as defined herein, including embodiments thereof.

The compound of formula (II) may have formula:

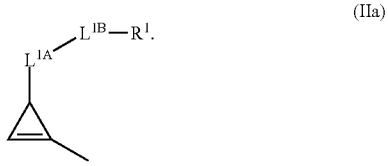
(IIa)

$L^{1A}$, $L^{1B}$, and $R^1$ are as described herein, including embodiments thereof.

The compound of formula (II) may have formula:

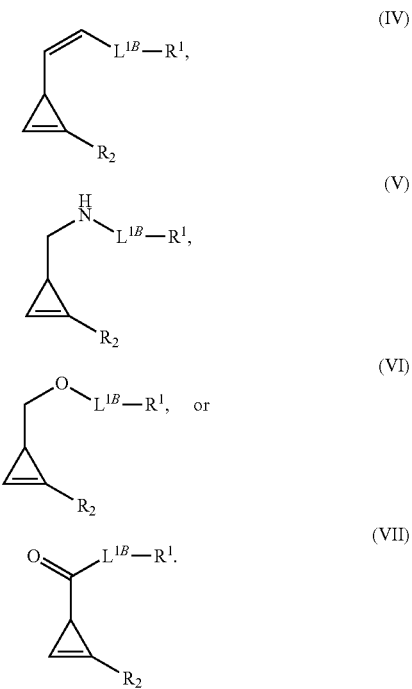

$L^{1B}$, $R^1$ and $R^2$ are as described herein, including embodiments thereof.

$R^2$ may be methyl, ethyl, or propyl. $R^2$ may be methyl. $L^{1A}$ and $L^{1B}$ may independently be substituted or unsubstituted alkylene or substituted or unsubstituted heteroalkylene.

$R^1$ may be hydrogen, halogen, —OH, —NH$_2$, —COOH, substituted or unsubstituted alkyl, a biomolecule, a detectable moiety, or a water soluble moiety. $R^1$ may be —OH. $R^1$ may be a biomolecule. $R^1$ may be a detectable moiety.

$R^3$ and $R^4$ may independently be hydrogen, halogen, —OH, —NH$_2$, —COOH, substituted or unsubstituted alkyl, substituted or unsubstituted heteroalkyl, substituted or unsubstituted cycloalkyl, substituted or unsubstituted aryl, substituted or unsubstituted heteroaryl, a detectable moiety, a water soluble moiety or a biomolecule, a detectable moiety, a water soluble moiety or a biomolecule. $R^3$ may be hydrogen, halogen, —OH, $C_1$-$C_5$ unsubstituted alkyl, or $C_5$-$C_6$ unsubstituted aryl. $R^3$ may be a biomolecule. $R^3$ may be a detectable moiety. $R^3$ may be a water soluble moiety. $R^4$ may be hydrogen, unsubstituted alkyl, unsubstituted heteroalkyl, unsubstituted aryl, unsubstituted heteroaryl, a detectable moiety, a water soluble moiety or a biomolecule. $R^4$ may be hydrogen or methyl. $R^4$ may be hydrogen. $R^4$ may be methyl. $R^4$ may be a biomolecule. $R^4$ may be a detectable moiety. $R^4$ may be a water soluble moiety.

The compound of formula (III) may have formula (III1). $R^4$ may be hydrogen. $R^4$ may be methyl. When $R^3$ is a biomolecule or a detectable moiety, $R^4$ may be methyl. $R^4$ may be a biomolecule. $R^4$ may be a detectable moiety. The compound of formula (III) may have formula as set forth in Table 1.

The contacting of a compound of formula (II) with a compound of formula (III) may be performed in a cell. The contacting may be performed when $R^1$, $R^3$, or $R^4$ is a detectable moiety, a biomolecule, or a water soluble moiety. One or more of $R^1$, $R^3$, or $R^4$ may be a detectable moiety, a biomolecule, or a water soluble moiety.

V. Methods for Detecting a Diazonorcaradiene

Where the diazonorcaradiene compounds of formula I include a detectable moiety, any appropriate method may be used to detect the detectable moiety and thereby detect the diazonorcaradiene. The detectable moiety may be a fluorophore, a radionuclide, or a magnetic contrast agent. The detectable moiety may be fluorescein, BODIPY, or a cyanine dye. The detectable moiety may be Fluorine-18, Gallium-68, or Copper-64. The detectable moiety may be gadolinium, iron oxide, iron platinum, manganese, or a paramagnetic species. The detectable moiety may be attached to a biomolecule. The detectable moiety may be a biomolecule such as GFP or luciferase. In certain embodiments, the detection of diazonorcaradiene is performed in combination with other techniques, such as biotinylation or Huisgen reactions, wherein such techniques use at least one compound covalently attached to a detectable moiety.

In certain embodiments, where the diazonorcaradiene compound of formula I may include a first detectable moiety and a second detectable moiety, wherein the first detectable moiety interacts with the second datectable moiety to modify the detectable signal. For example, the first detectable moiety may quench the detectable signal (e.g., fluorescense) of the second detectable moiety. For example the first detectable moiety may be a FRET donor and the second detectable moiety may be FRET acceptor or vice cersa. Thus, the formation of the diazonorcaradiene may be detected by detecting the quenching of a first detectable moiety (e.g. present within a compound of formula (II)) by a second detectable moiety (e.g. present within a compound of formula (III)) upon formation of the diazonorcaradiene compounds. For example, a compound of formula (II) having a FRET acceptor may be contacted with a compound of formula (III) having a FRET donor thereby forming the diazonorcaradiene compound of formula (I). The quenching of the FRET pair is detected thereby detecting the formation of the diazonorcaradiene compound of formula (I). The decrease in the signal may be about 1×, 2×, 3×, 4×, 5×, 6×, 7×, 8×, 9×, 10×, 15×, 20×, 25×, or 30× the intensity before forming the diazonorcaradiene.

In embodiments, the tetrazine moiety of formula (III) is capable of quenching a detectable signal from a detectable moiety with $R^1$, $R^3$ or $R^4$. Thus, in some embodiments the $R^1$, $R^3$ or $R^4$ include (or are) a FRET donor and the tetrazine moiety of formula (III) is a FRET acceptor. Thus, the formation of the diazonorcaradiene compound of formula (I) may be detected by the loss of signal quenching between the tetrazine moiety of formula (III) and a FRET donor within $R^1$, $R^3$ or $R^4$. The increase in the signal may be about 1×, 2×, 3×, 4×, 5×, 6×, 7×, 8×, 9×, 10×, 15×, 20×, 25×, or 30× the intensity before forming the diazonorcaradiene. Thus, one or more of $R^1$, $R^3$, or $R^4$ may be or include a detectable moiety.

VI. Methods for Detecting Ligated Oligonucleotides

In certain embodiments a method is provided for ligating a first nucleic acid and a second nucleic acid. The method includes combining a template nucleic acid, the compound of formula (II) as described herein and a compound of formula (III) as described herein in a reaction vessel, wherein $R^1$ is a first nucleic acid moiety and $R^3$ is a second nucleic acid moiety. The template nucleic acid includes a first nucleic acid sequence that is at least partially complementary to the first nucleic acid moiety (e.g. hybridizable under stringent conditions) and a second nucleic acid sequence that is at least partially complement to the second nucleic acid moiety (e.g. hybridizable under stringent conditions). The first nucleic acid moiety and the second nucleic acid moiety are allowed to hybridize to the template nucleic acid. The compound of formula (II) as described is allowed to react with a compound of formula (III) to from a diazonorcaradiene for formula I as described above, wherein $R^1$ is the first nucleic acid moiety and $R^3$ is the second nucleic acid moiety, thereby ligating the first nucleic acid moiety and the second nucleic acid moiety. The reaction vessel may be any appropriate vessel, including a cell.

The first nucleic acid or the second nucleic acid (or both) may include a detectable moiety. In certain embodiments, the first and second nucleic acids are ligated in the absence of a detection moiety. The compounds of formulae (II) and (III) may be attached to the 3' end or the 5' end of the nucleic acid moieties. In embodiments, where the compound of formula (II) is attached to the 3' end, the compound of formula (III) is attached to the 5'end. In embodiments, where the compound of formula (II) is attached to the 5' end, the compound of formula (III) is attached to the 3'end. $R^4$ may be a $C_1$-$C_5$ alkyl, a biomolecule or a detectable moiety. $R^4$ may be methyl. $R^4$ may be a detectable moiety. The detectable moiety may be within 1 to 10 base pairs of the compound of formula (III) or formula (II). When the detectable moiety is attached to a base pair, the compound of formula (III) may quench the emission of the detectable moiety (e.g. tetrazine may act as a FRET acceptor as described above). The emission of the detectable moiety may be unquenched upon formation of a diazonorcaradiene. The detecting of the oligonucleotide-templated ligation may be observed by an increase in fluorescence.

The compound of formula (II) may contain a detectable moiety. The compound of formula (II) may be attached to the 5' end of the first oligonucleotide.

In certain embodiments, the diazonorcaradiene-linked first and second nucleic acid (also referred to herein as the diazonorcaradiene) different melting temperature to their complementary sequence than the melting temperature in the absence of the diazonorcaradiene moiety (i.e. free nucleic acid not linked to the diasonorcaradiene). Changes in the melting temperature of the diazonorcaradiene-oligonucleotide may be useful in detecting nucleotide mismatches, wherein a lowered melting temperature may indicate a nucleotide mismatch. The lowered melting temperature may be a result of destabilization of the oligonucleotide binding. The method may detect oligonucleotide sequences having a single nucleotide mismatch. The formation of the diazonorcaradiene may occur within 1-10,000 seconds. The formation may occur within 1-1000 seconds. The formation may occur within 20-240 seconds. The concentration of the cyclopropene-oligonucleotide probe and the tetrazine-oligonucleotide probe may be about equal. The concentration of the cyclopropene-oligonucleotide probe and the tetrazine-oligonucleotide probe may be about 0.1 uM to about 2 uM. The concentration of the cyclopropene-oligonucleotide probe and the tetrazine-oligonucleotide probe may be about 1 uM. The oligonucleotide may be an RNA or DNA. The oligonucleotide may be a DNA sequence.

VII. Methods of Detecting a Compound Moiety in a Cell

In certain embodiments a method is provided for detecting the presence of a compound in a cell. The method includes contacting a cell or organism with a compound of formula (II) wherein $R^2$ is a compound moiety (e.g. a biomolecule moiety). The organism or cell is allowed to process (e.g. metabolize, catabolize or otherwise process) the compound of formula (II). The method further includes contacting the cell with a compound of formula (III) wherein $R^3$ is a detectable moiety and allowing the compound of formula (III) to react with the compound of formula (II) thereby forming the diazonorcaradiene of formula (I) as described above. The detectable moiety is then detected thereby detecting the presence of the compound moiety in the cell. The method may further include a wash step, wherein the cells contacted with a compound of formula (II) are washed (e.g. buffer or media exchange) before the contacting with a compound of formula (III). The molecule moiety may be a glycan moiety. The glycan moiety may be a hexosamine moiety. The compound of formula (II) may be a compound having formula (VIII), (VIII1), (VIII2), (VIII3), or (VIII4).

VIII. Method of Synthesis of a Cyclopropene-Amino Hexanose

In another aspect a method is provided for synthesizing a cyclopropene-amino hexanose having formula:

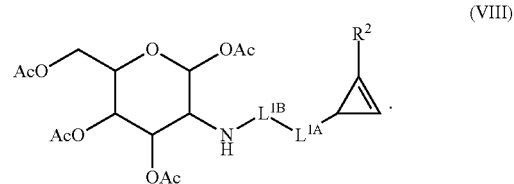

(VIII)

The method includes contacting a peracetylated hexosamine having formula

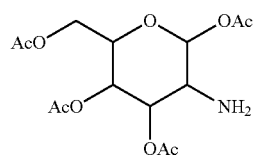 [SMILES: CC(=O)OCC1OC(OC(C)=O)C(N)C(OC(C)=O)C1OC(C)=O]

with a compound having formula $$\text{(II)}$$

thereby synthesizing a compound of formula (VIII). The method may include forming a hexosamine protected secondary amine from a hexosamine, acetylating the alcohols of the hexosamine protected secondary amine to form a peracetylated hexosamine protected secondary amine and deprotecting the peracetylated hexosamine protected secondary amine to form a peracetylated hexosamine. The compound of formula (VIII) may have formula (VIII1), (VIII2), (VIII3) or (VIII4). $L^{1A}$, $L^{1B}$, and $R^2$ are as described herein, including embodiments thereof.

IX. EXAMPLES

Example 1

Starting Materials

All chemicals were received from commercial sources and used without further purification. End-modified DNA oligonucleotides were purchased from Integrated DNA Techologies, Inc and used after HPLC purification, lyophilization and resuspension in ddi $H_2O$. DNA and RNA templates of 27-37 nucleotide length were purchased from IDT and used upon resuspension in ddi $H_2O$ without further purification.

```
DNA template:
5'-TTG ACG CCA TCG AAG G[T]A GTG TTG AAT -3'
(linker region underlined, single mismatch
position in brackets)(SEQ ID NO:1);

13merF15'tet:
5'-tetrazine-/5AmMC6//iFluorT/CG ATG GCG TCA A-3'
(modified nucleotides indicated following the
manufacturer's nomenclature)(SEQ ID NO:4);

13mer3'cyclopropene:
5'-ATT CAA CAC TAC C/3AmMO/-cyclopropene-3'
(SEQ ID NO:5);

7mer3'cyclopropene:
5'-CAC TAC C/3AmMO/-cyclopropene-3';

5mer 3'cyclopropene:
5'-CTA CC/3AmMO/-cyclopropene-3'.
```

Synthesis of a Exemplary Tetrazine Tag

70%

To a stirred solution of tert-butyl 4-(6-methyl-1,2,4,5-tetrazin-3-yl)benzylcarbamate (10.0 mg, 0.033 mmol) in $CH_2Cl_2$ (1.0 mL), $CF_3COOH$ (0.25 mL) was added at room temperature. The resulting solution was stirred for 2 hours and then evaporated to afford (4-(6-methyl-1,2,4,5-tetrazin-3-yl)phenyl)methanamine TFA salt. This resulting salt was dissolved in $CH_2Cl_2$ and $Et_3N$ (10.0 mg, 0.10 mmol) was added, followed by glutaric anhydride (4.0 mg, 0.033 mmol). The resulting solution was stirred for 1 hr at room temperature and then N,N'-disuccinimidyl carbonate (13.0 mg, 0.05 mmol) was added. The reaction solution was stirred at room temperature for 1 hour and then evaporated. The residue was purified by preparative TLC (Hexanes:EtOAc at 3:1) to afford 9.5 mg product as pink solid. The resulting yield was 70%.

$^1$H NMR (500 MHz, CDCl$_3$) δ 2.15 (2H, m), 2.38 (2H, t, J=10 Hz), 2.67 (2H, t, J=10 Hz), 2.82 (4H, bs), 3.09 (3H, s), 4.55 (2H, t, J=5 Hz), 6.46 (1H, bs), 7.49 (2H, dd, J=10 Hz, 5 Hz), 8.52 (2H, dd, J=10 Hz, 5 Hz); $^{13}$C (100 MHz, CDCl$_3$) δ 21.15, 21.39, 25.80, 30.10, 34.52, 43.51, 128.43, 128.74, 143.42, 155.77, 164.11, 167.49, 168.55, 169.53, 171.86. HRMS [M+Na]$^+$ m/z calcd. for [C$_{19}$ H$_{20}$ N$_6$ O$_5$ Na]$^+$ 435.1387. found 435.1386.

Synthesis of a Exemplary Cyclopropene Carbamate Tag

85%

To a stirred solution of (2-methylcycloprop-2-en-1-yl)methyl(2-hydroxyethyl)carbamate (10.0 mg, 0.058 mmol) in $CH_3CN$ (1.0 mL) at room temperature was added $Et_3N$ (12.0 mg, 0.12 mmol) followed by N,N'-disuccinimidyl carbonate (30.0 mg, 0.12 mmol). The reaction solution was left stirring at room temperature overnight. Next day the reaction solution was evaporated and the residue was purified by preparative TLC (Hexanes:EtOAc at 5:1) to afford 15.0 mg product as colorless liquid. The resulting yield was 85%.

$^1$H NMR (500 MHz, CDCl$_3$) δ 1.65 (1H, m), 2.13 (3H, s), 2.84 (4H, s), 3.53 (2H, m), 3.93 (2H, m), 4.39 (2H, t, J=10

Hz), 5.05 (1H, bs), 6.55 (1H, s); $^{13}$C (100 MHz, CDCl$_3$) δ 11.88, 17.32, 25.67, 39.84, 70.60, 72.98, 102.28, 120.87, 151.62, 156.97, 168.77. HRMS [M+Na]$^+$ m/z calcd. for [C$_{13}$H$_{16}$N$_2$O$_7$Na]$^+$ 335.0850. found 335.0848.

Synthesis of a Exemplary Cyclopropene Amide Tag

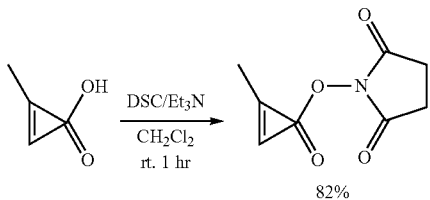

To a stirred solution of 2-methylcycloprop-2-enecarboxylic acid (50.0 mg, 0.51 mmol) in CH$_2$Cl$_2$ (2.0 mL) at room temperature was added Et$_3$N (60.0 mg, 0.60 mmol) followed by N,N'-disuccinimidyl carbonate (153.0 mg, 0.60 mmol). The reaction solution was stirred at room temperature for 1 hour. The reaction solution was evaporated and the residue was purified by preparative TLC (Hexanes:EtOAc at 5:1) to afford 82.0 mg product as colorless liquid. The resulting yield was 82%.

$^1$H NMR (500 MHz, CDCl$_3$) δ 2.17 (3H, s), 2.28 (1H, d, J=5 Hz), 2.75 (4H, s), 6.36 (1H, s); $^{13}$C (125 MHz, CDCl$_3$) δ 10.3, 17.5, 25.6, 93.3, 110.5, 169.7, 171.1. HRMS [M+Na]$^+$ m/z calcd. for [C$_9$H$_9$NO$_4$Na]$^+$ 218.0424. found 218.0425.

Modified Oligonucleotide Synthesis and Characterization

Amine-modified oligonucleotide sequences at selected terminus were modified by reacting with excess cyclopropene or tetrazine carboxylic acid NHS ester in 50 mM sodium bicarbonate buffer containing 100-1000 mM NaCl. Main product formed without significant side reactions. Cyclopropene or tetrazine carboxylic acid NHS esters were dissolved in DMF at 100 mM concentration, and added at 5× excess to the aqueous reaction solution containing 0.1-1.5 mM oligonucleotide. Upon partial reaction or NHS ester hydrolysis, another 5× excess was added 30-60 min later, and the process was repeated until no more reactant oligonucleotide was detected by HPLC.

Oligonucleotide detection by HPLC was done using Agilent 1260 Infinity LC/MS system with Phenomenox Oligo-MS 150-4.6 mm column. About 20 pmol samples were injected and eluted with a gradient of 6-18% acetonitrile in 5 mM ammonium acetate at pH 7.25.

Final prepared oligonucleotide molecular weights were confirmed by MALDI-TOF MS using a Biflex IV system (Bruker Daltronics). Each construct molecular weights were located at the main m/z peaks. Representative spectra are shown in Figure S1. Ligation reaction product weights were determined by TOF upon separation by LC using the same gradient elution described above using a 6230 TOF MS (Agilent Technologies). Detected ligation product molecular weights are show in Figure S2. An example HPLC reaction (Figure S3) shows the typical ligation reaction upon completion, with overlaid reactant elution peaks using Agilent Technologies 1260 Infinity LC/MS (equipped with a 6120 quadrupole MS ionization-spray detector) with the gradient elution described above.

Melting temperature of probes and ligation products in hybridization buffer (50 mM MOPS pH 7.5, 250 mM NaCl) were measured using a Beckman-Coulter DU 640 spectrophotometer equipped with a high performance temperature controller and micro auto six-cell holder. Samples at 1 µM concentration of each oligonucleotide were heated to 90° C. and slowly cooled to RT over 1-1.5 h before the measurements. Melting temperature values were obtained by cooling samples from 90° C. to 20° C. at the rate of 1° C./min and measuring at 1° C. increments with each read averaged over 1 s.

Ligations of Modified Oligonucleotides

Tetrazine and cyclopropene-modified oligonucleotide probes were ligated in the presence of a DNA or RNA template at a 1:1:1 ratio. Reactions were done in varying solution and temperature conditions, as indicated. Main hybridization buffer was 50 mM MOPS at pH 7.5, 250 mM NaCl. Ligation reactions with a mismatched DNA template were performed in 5 mM MgCl$_2$ in standard 1× Tris-borate buffer (purchased as 10× UltraPure TBE from Invitrogen: 1.0 M Tris pH 8.4, 0.9 M Boric acid, 10 mM EDTA).

Tetrazine stability was tested by taking Nanodrop UV-Vis absorbance measurements over time. Characteristic tetrazine absorbance peak intensity at 520 nm was measured by first subtracting the background level intensity at each point, estimated as the trendline between the intensity levels immediately preceding and following the tetrazine peak. Tetrazine and cyclopropene modification analogs used for this reaction are indicated next to the corresponding data trends in Figure S3. Reactions were done in the standard hybridization buffer at room temperature of approximately 22° C. at 1 mM tetrazine and 10 mM cyclopropene concentrations. Data for the tetrazine-cyclopropene reaction was fit to a one-phase decay of the tetrazine absorption peak using GraphPad Prism 6.0a for Mac, GraphPad Software, La Jolla Calif. USA, www.graphpad.com.

Ligation reactions were done in standard 96 fluorescence well plates using SpectraMax GeminiXS (Molecular Devices). Temperature was set by the instrument. Where indicated by standard deviations, experiments were performed multiple times. In order to avoid any secondary structure artifacts, DNA or RNA template with added tetrazine probe was first heated to 90° C. and crash-cooled on ice for 2 min right before the experiment. Each well was filled with a total of 100 µL reaction solution, and reactions were timed from the addition of the cyclopropene probe as the last step before starting the measurements. Wells were scanned every 20-60 s depending on the speed of the reactions by using 485 nm excitation and 538 nm emission with the cutoff set at 495 nm. Control reactions without template were done in parallel each time. Buffer-only well intensities were subtracted from the measured raw data before analysis. Data was analyzed using GraphPad Prism 6.0 by applying a nonlinear fit of a one-phase association to each curve where fluorescein signal during reaction was measured.

Oligonucleotide Probe Applicability for Cellular Detection

Oligonucleotide probes were tested for stability in media over the typical timescales of probe incubation for cellular delivery. The 13mer5'tet probe and template DNA were incubated in D-MEM media (Dulbecco's Modified Eagle Medium, Gibco) in 10% BenchMark fetal bovine serum (Gemini Bio-Products) for 3 h at room temperature and allowed to react for 1 h with 13mer3'cycp1. All DNA concentrations were kept at 1 µM. Measurements were taken right before addition of the cycp1 probe in order to establish the baseline, which was subtracted from the final tetrazine peak intensity after full reaction. Fluorescence measurements were done using a Perkin Elmer LD-45 spectrophotometer equipped with a single cuvette reader, with the excitation and emission wavelengths set to 485/5 nm and 520/5 nm, respectively (spectral slitwidths indicated). Multiple reads were taken for each sample.

Figure 2:
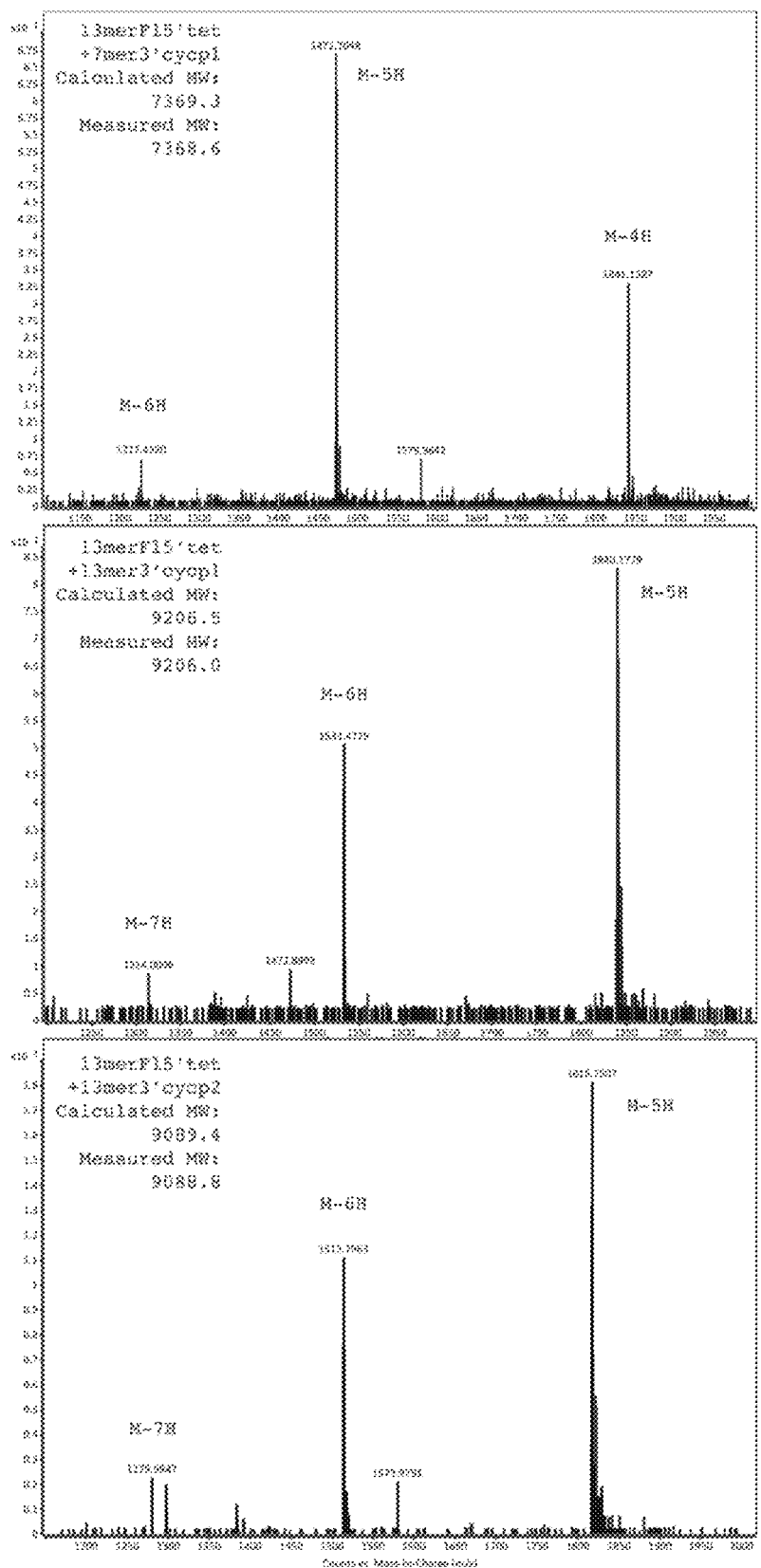
FIG. 2. TOF MS of modified oligonucleotide ligation products.
Figure 3:
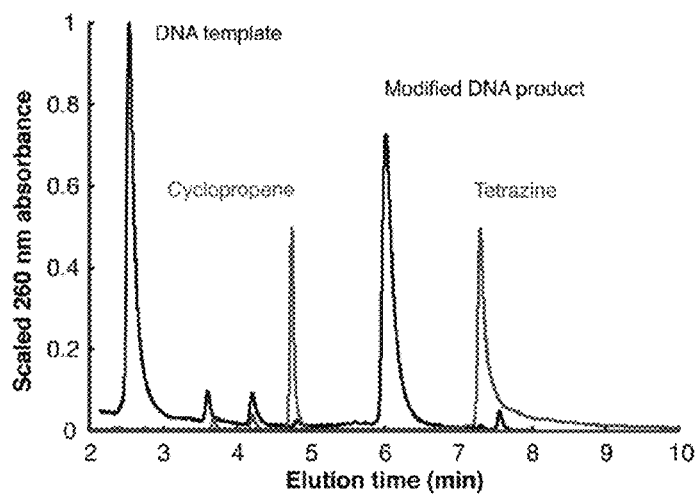
FIG. 3. LC/MS traces of representative hybridization reactions showing 260 nm absorption peaks for detected oligonucleotide species overlaid with the reaction mixture after completion (cyclopropene1 elution at 4.8 min, tetrazine at 7.5, 27mer DNA template eluting at 2.5 min, the modified DNA product at 6 min).
Figure 4:
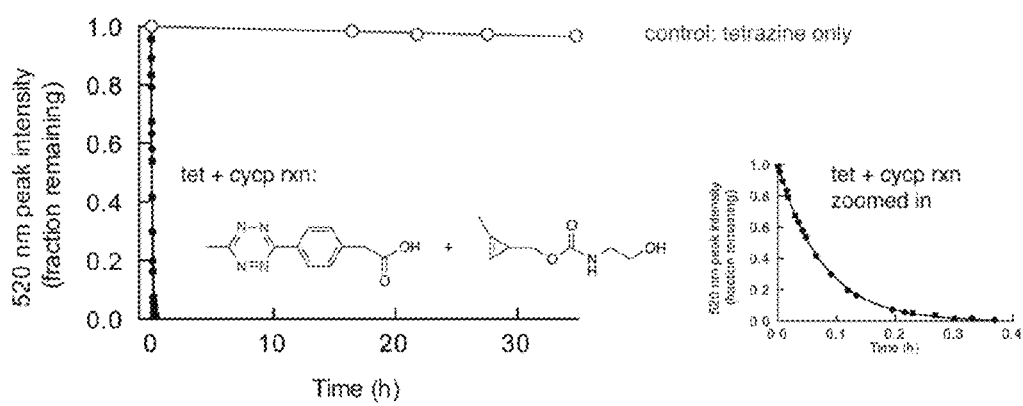
FIG. 4. Measure of tetrazine solution stability over time and tetrazine-cyclopropene small molecule precursor reaction using a Thermo Fisher Nanodrop 2000c spectrometer, in 250 mM NaCl, 50 mM MOPS pH 7.5 with a tetrazine carboxylic acid at 1 mM concentration and a 10 mM excess cyclopropene alcohol (structures indicated)
Figure 5:
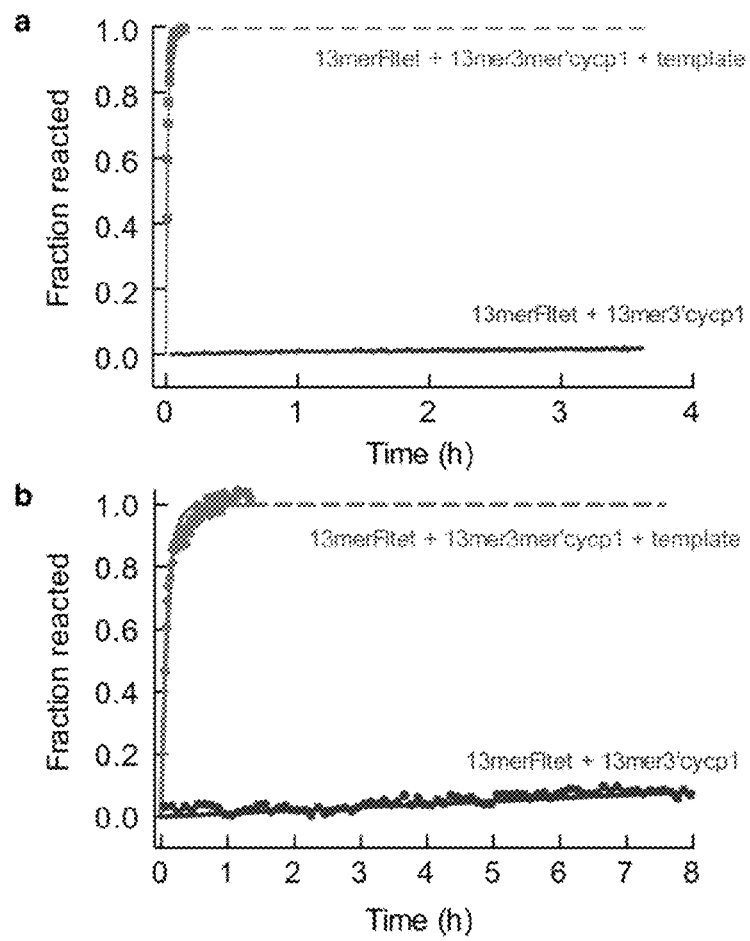
FIG. 5. Fluorogenic tetrazine probe does not turn on in the absence of template (dashed lines indicate completed reaction extrapolation); a) shows reaction in the presence and absence of DNA template of 1 µM reactants in hybridization buffer (250 mM NaCl, 50 mM MOPS pH 7.5) at 25° C.; b) shows reaction in the presence and absence of DNA template of 1 µM reactants in C-DMEM media in serum at 37° C.
Figure 6:
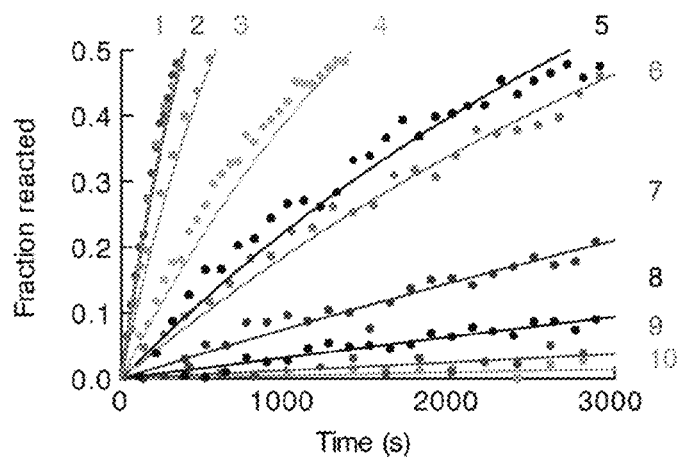
FIG. 6. Effect of gap length in tetrazine-cyclopropene modified DNA reaction efficiency: DNA templates of increasing center sequence insert length were used to react 13merFltet and 13mer3'cycp1 in 150 mM MOPS buffer pH 7.5 at 25° C. (The number of nucleotides in the non-hybridizing gap region are indicated next to the data points and fitted lines).
Figure 7:
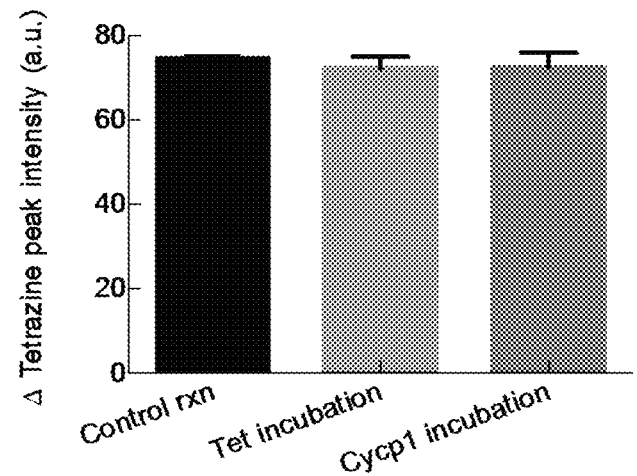
FIG. 7. Oligonucleotide probe stability in cell media: Each probe (13mer5'tet and 13mer 3'cycp1) (concentrations kept at 1 µM) was incubated for 3 h at room temperature in C-DMEM media in serum and allowed to react with the corresponding probe in the presence of template for an additional 1 h whereupon the final 4 h tetrazine fluorescence timepoints were taken and averaged, and the baseline tetrazine intensities were subtracted and compared to control reaction denoting a fully reacted 13mer5'tet+13mer3'cycp1+ 27nt template with no incubation.
Figure 8:
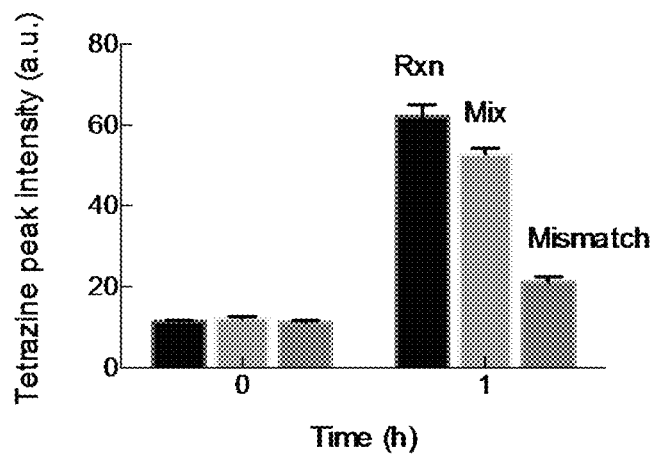
FIG. 8. Oligonucleotide probe fidelity in the presence of mismatched template: tetrazine and cyclopropene probes (13mer5'tet and 7mer3'cycp1) at 1 µM were reacted with a fully matched 1 µM template (labelled "Rxn") or 1 µM single nucleotide mismatch ("Mismatch"), or a mix of 1 µM fully matched and 1 µM singly mismatched template ("Mix").
Figure 9:
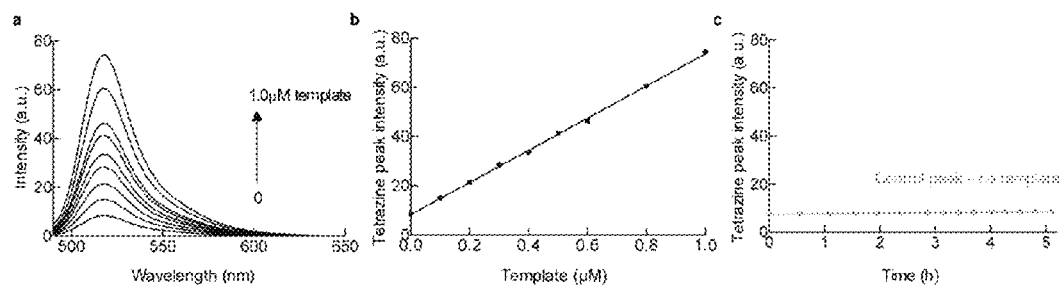
FIG. 9. Template titration into the probe solution: a) shows a 27nt template added at 0.1 µM increments from 0 to the final 1 µM concentration into a solution containing 1 µM 13mer5'tet and 1 µM 13mer3'cycp1 in the hybridization buffer at room temperature (50 mM MOPS pH 8.5, 250 mM NaCl) and the reaction was allowed to proceed for 15-20 min prior to the tetrazine peak intensity scan at each titration point; b) shows linear tetrazine peak intensity increase during 27nt template titration; c) shows the control probe solution performed in parallel, and allowed to incubate with no addition of template.
Figure 10:
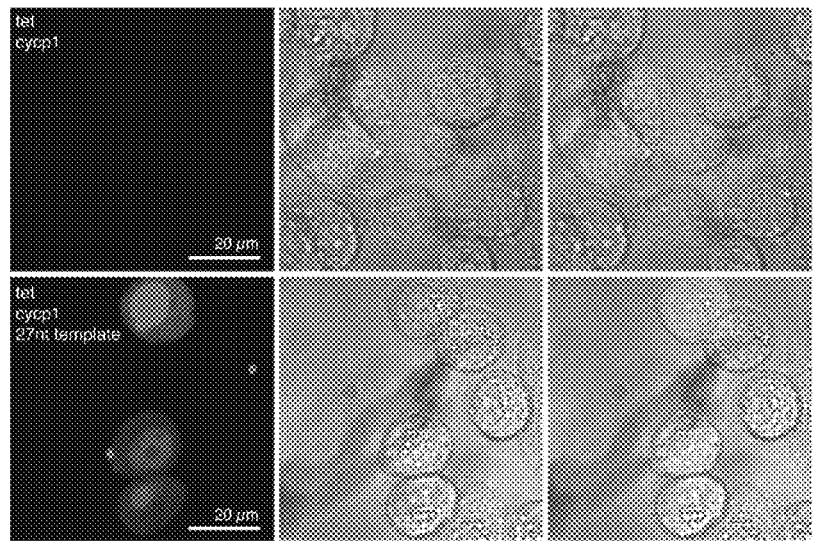
FIG. 10. Oligonucleotide probe reaction inside live cells: SKBR3 human breast cancer cells were incubated with oligofectamine/DNA for 4 h and imaged using an Olympus FV1000 confocal microscope ando reaction was observed in cells that were not exposed to a fully matched 27 nt template (first row with tet and cycp1 only).
Figure 11:
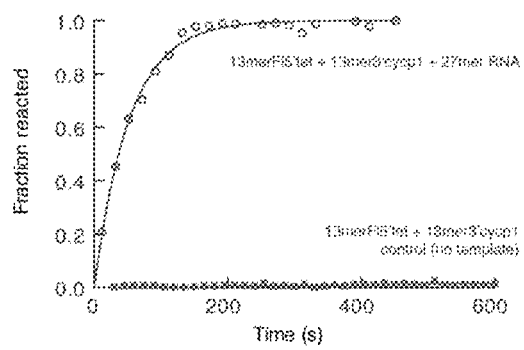
FIG. 11. Short oligonucleotide probes are equally effective in ligating with an RNA template: the corresponding 27mer RNA template was used in ligating 13merF15'tet and 13mer3'cycp1.
Figure 12:
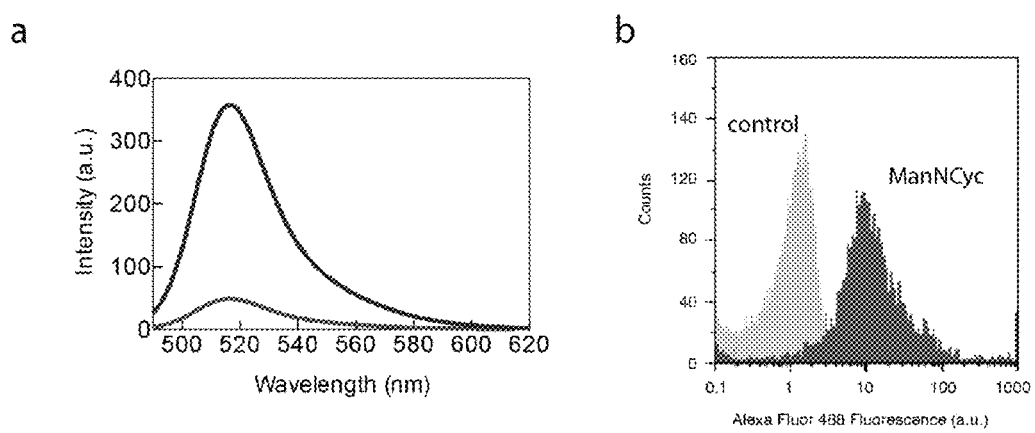
FIG. 12. a) shows emission spectra demonstrating the fluorogenic response of tetrazine-Alexa Fluor 488 before and after incubation with Ac$_4$ManNCyc 3; b) shows flow cytometry indicating fluorescent staining of SKBR3 cells incubated with Ac$_4$ManNCyc followed by tetrazine-Alexa Fluor 488 wherein the control cells not exposed to the cyclopropene registered significantly less fluorescence intensity.
Figure 13:
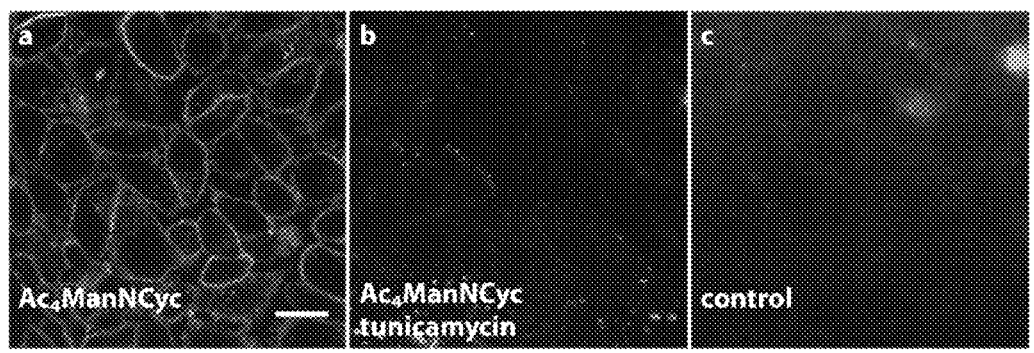
FIG. 13. Imaging SKBR3 cells: Separate populations of SKBR3 cells were incubated for 48 hours with (a) Ac$_4$ManNCyc, (b) Ac$_4$ManNCyc and 1.2 µM tunicamycin, and (c) a control solution lacking a mannosamine derivative, then reacted with 10 µM tetrazine-Alexa Fluor 488 and imaged by confocal microscopy with cells receiving only Ac$_4$ManNCyc showing bright surface staining
Figure 14:
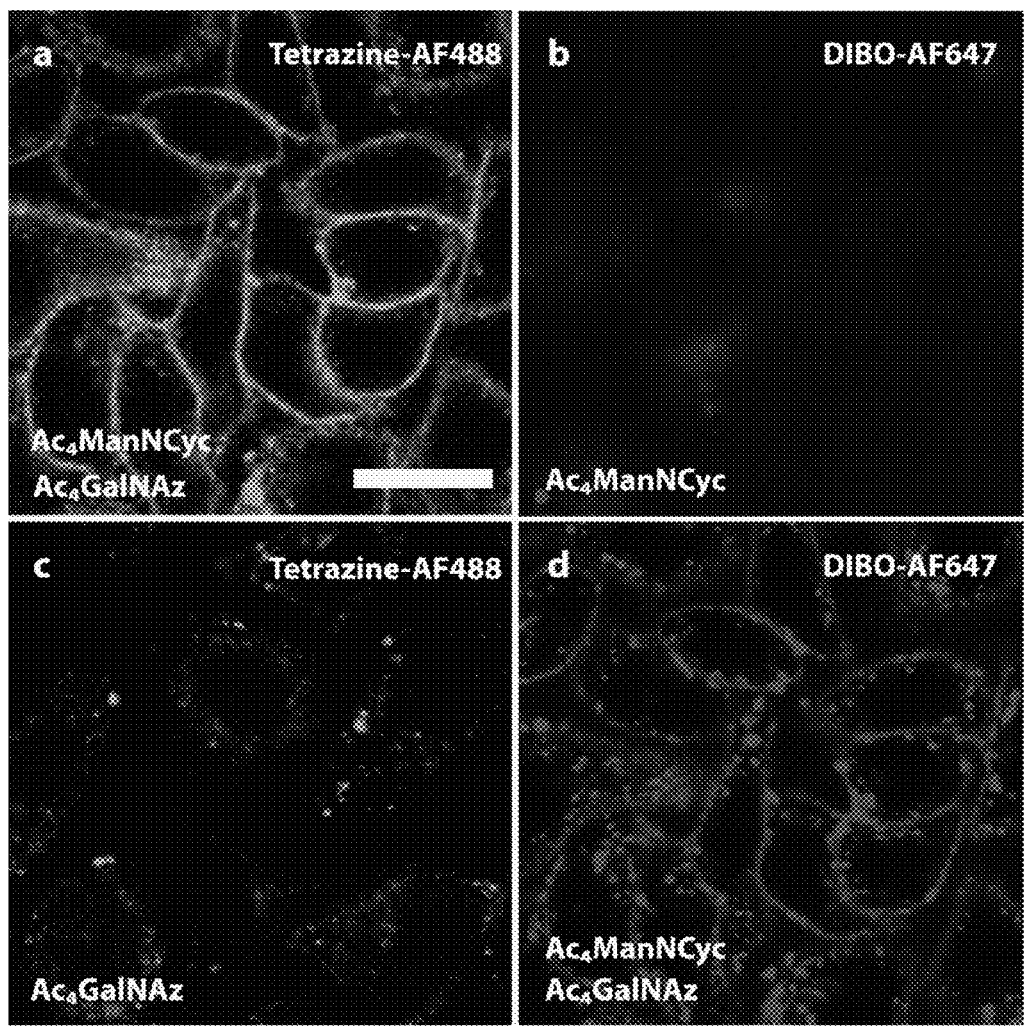
FIG. 14: Cross reactivity studies: SKBR3 cell surfaces were incubated for 48 hours with Ac$_4$ManNCyc and Ac$_4$GalNAz reacted with both tetrazine-Alexa Fluor 488 and DIBO Alexa Fluor 647 and imaged by confocal microscopy in (a) the 488 channel and (d) the 647 channel; (b) shows cells that were incubated for 48 hours with Ac$_4$ManNCyc and reacted with DIBO Alexa Fluor 647; (c) shows incubated with Ac$_4$ManNAz and reacted with tetrazine-Alexa Fluor 488.
Figure 15:
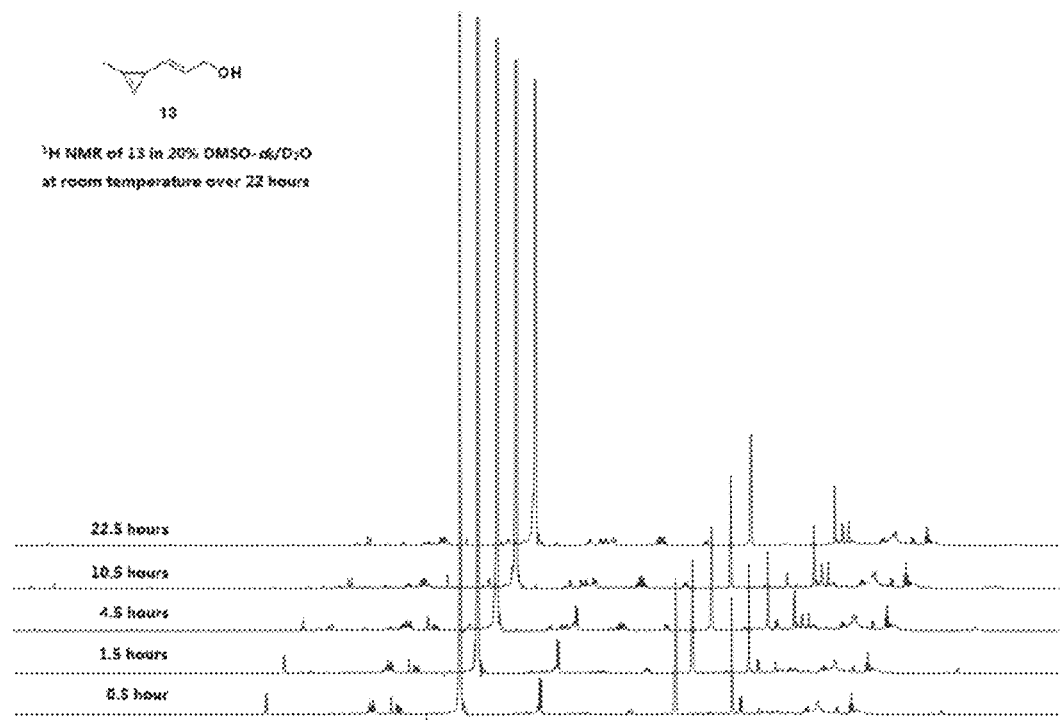
FIG. 15: Stability determination of cyclopropene derivative 13 using 1H NMR.
Figure 16:
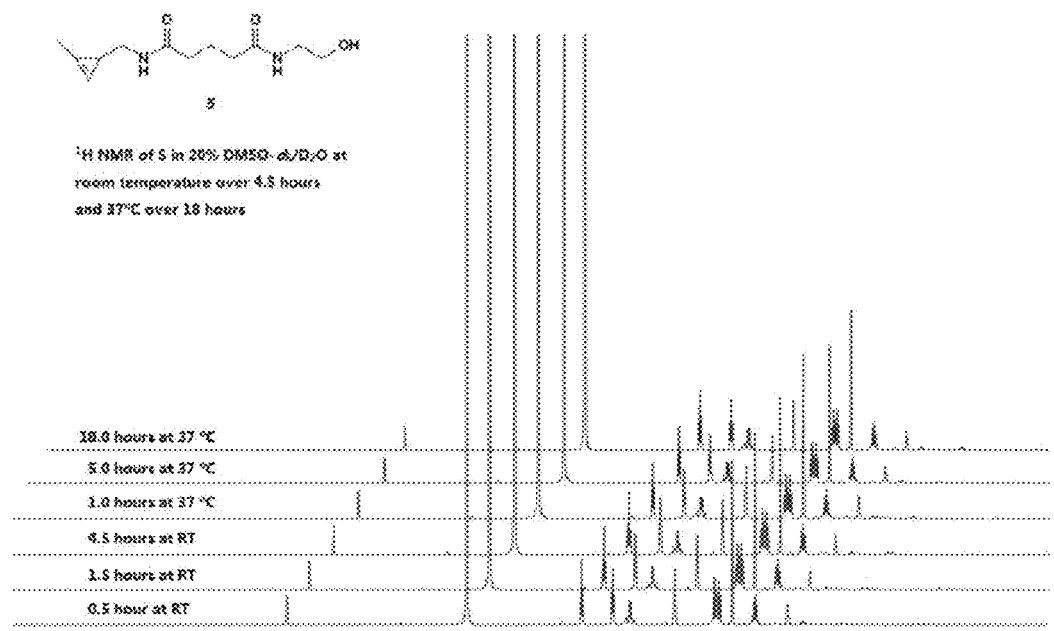
FIG. 16: Stability determination of cyclopropene derivative 5 using 1H NMR.
Figure 17:
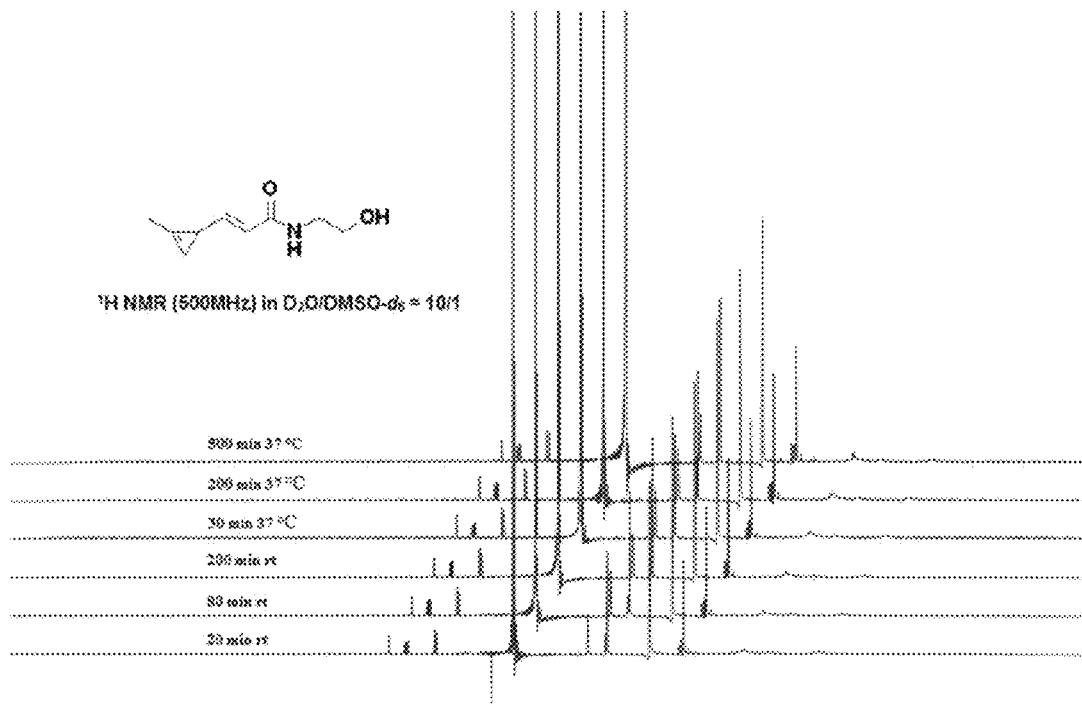
FIG. 17: Stability determination of cyclopropene derivative using 1H NMR.
Figure 18:
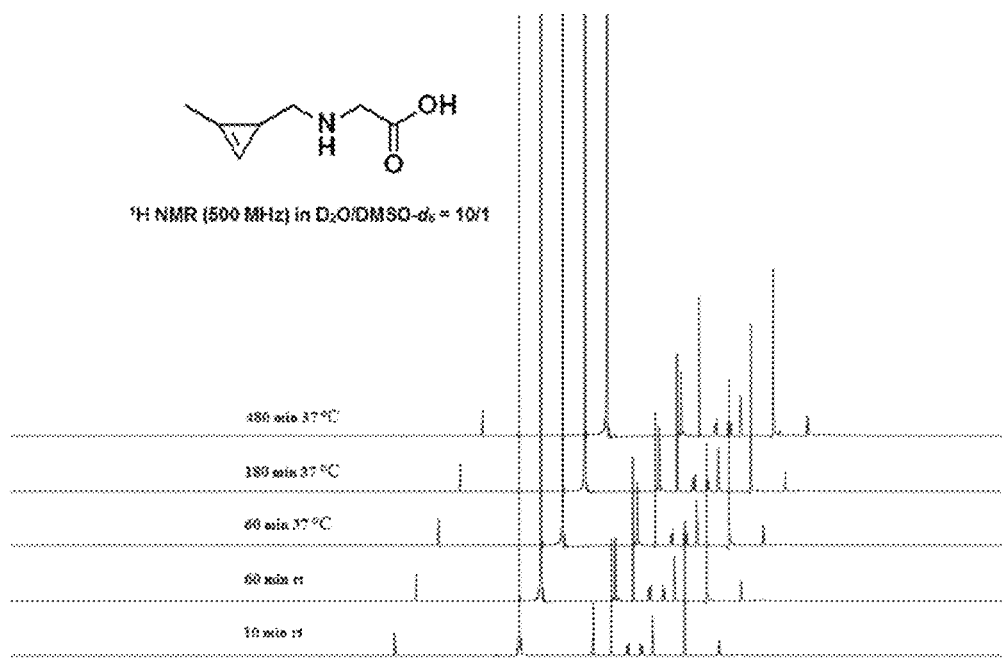
FIG. 18: Stability determination of cyclopropene derivative using 1H NMR.
Figure 19:
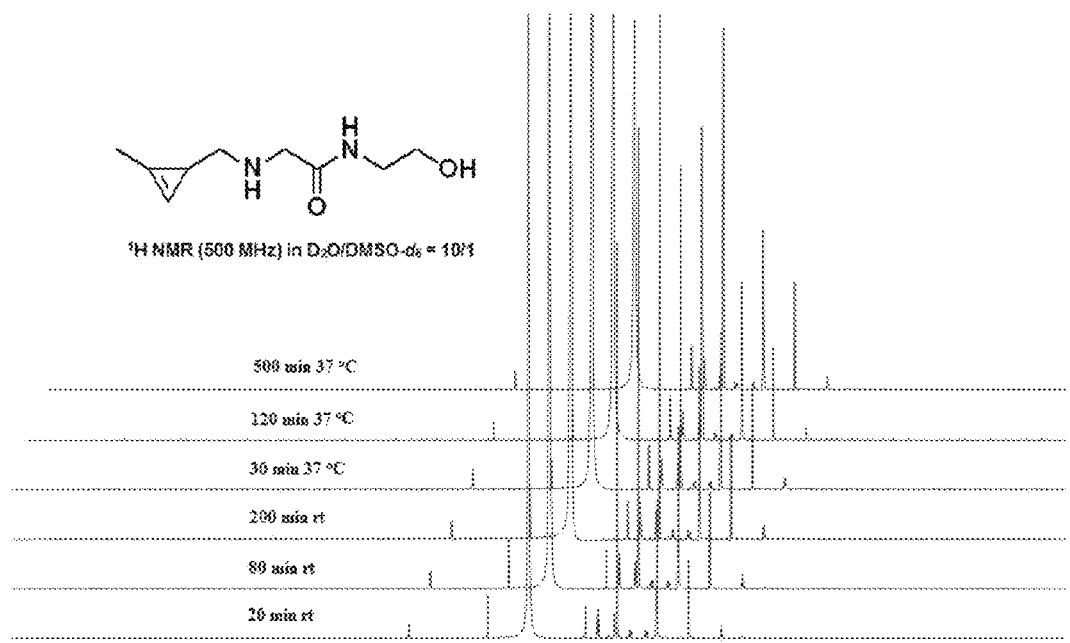
FIG. 19: Stability determination of cyclopropene derivative using 1H NMR.

A single nucleotide mismatch effect was determined on reaction completion in discriminating conditions from FIG. 2C and is depicted in Figure S8. TBE 1× buffer (pH 8.4, Invitrogen) with 5 mM MgCl$_2$ solution at 37° C. was used for incubation of 13mer5'tet with 13mer3'cycp1 in the presence of a fully matched template, or a sample containing a fully matched template and a single mismatched template, and a sample with only a singly-mismatched template. All DNA concentrations were kept at 1 µM. Fluorescence measurements were taken using a Perkin Elmer LD-45 spectrophotometer, as described above, with the samples in the quartz cuvettes warmed with attached circulating water bath. Initial timepoints were taken of prewarmed samples prior to template addition, and subtracted from the final intensity values (Figure S8).

Fully-matched 27mer template was titrated into a sample of equimolar 13mer5'tet and 13mer3'cycp1 (1 µM) at 22° C. room temperature in hybridization buffer (50 mM MOPS pH 8.5, 250 mM NaCl). Fluorescence scans were done upon 15-20 min equilibration of each 0.1 µM template addition up to the final 1 µM concentration. Perkin Elmer LD-45 spectrophotometer was used with 485/5 nm excitation scanning at 492-650/5 nm (slitwidths indicated). Control reaction with no template was measured in parallel in order to track any background untemplated reactant ligation.

Preliminary cellular experiments were performed with adherent human breast cancer SKBR3 cells. Transfection reagent oligofectamine (Invitrogen) was used for intracellular oligonucleotide probe delivery according to manufacturer's instructions. Briefly, oligofectamine was preincubated in OptiMEM media (Invitrogen) for 10 min before adding the probes and template in separate eppendorf tubes for oligofectamine/DNA complex formation over 30 min. These initial DNA/oligofectamine-containing solutions were added to a final of 150 µL OptiMEM media over SKBR3 cells in Glass-Tec slides, with the resulting DNA concentration of 0.5 µM each. SKBR3 cells were incubated at 37° C. for 4 h and imaged using an Olympus FV1000 confocal microscope. Images were processed using ImageJ 1.47 g software package.

TABLE

Melting temperatures of DNA template with the reacted oligonucleotide target.

| Template | Hybridization target | Solution conditions | Melting T (° C.) |
|---|---|---|---|
| 27mer | 27mer | 250 mM NaCl in buffer | 75.5 |
| 27mer | 13merFl5'tet | 250 mM NaCl in buffer | 57.4 |
| 27mer | 13mer3'cycp1 | 250 mM NaCl in buffer | 50.4 |
| 27mer | 5mer3'cycp1 | 250 mM NaCl in buffer | 41.4 |
| 27mer | 13merFl5'tet + 13mer3'cycp1 | 250 mM NaCl in buffer | 65.8 |
| 27mer | 13merFl5'tet + 13mer3'cycp2 | 250 mM NaCl in buffer | 65.8 |
| 27mer | 13merFl5'tet + 7mer3'cycp1 | 250 mM NaCl in buffer | 59.9 |
| 27mer | 13merFl5'tet + 5mer3'cycp1 | 250 mM NaCl in buffer | 56.9 |

Table: Oligonucleotide Probe Binding Site Separation Effect on the Ligation Reaction Kinetics.

Apparent reaction rate constants and half times of template-catalyzed 13mer5'Fltet+13mer3'cycp1 cycloadditions, with increasing template central gap length from 1 to 10. Reactions were done in parallel at 25° C. in 150 mM MOPS buffer pH 7.5 with no additional salt in order to optimize reaction rates for the extended comparison.

| Template gap length | Rate constant (s$^{-1}$) | $t_{1/2}$ (s) |
|---|---|---|
| 1 | 0.0018 | 382.8 |
| 2 | 0.0018 | 385.8 |
| 3 | 0.0012 | 578.8 |
| 4 | 0.00050 | 1399 |
| 5 | 0.00025 | 2727 |
| 6 | 0.00021 | 3343 |
| 7 | 0.000079 | 8803 |
| 8 | 0.000033 | 21081 |
| 9 | 0.000013 | 54453 |
| 10 | 0.0000049 | 142580 |

For ligation partners, a tetrazine-dienophile pair was required that would not appreciably react at micromolar concentrations over a period of days, but when brought into close proximity by an oligonucleotide template, would react rapidly and produce a fluorescence signal. Based on preliminary experiments, the reaction between methyl-terminated tetrazines and methyl-cyclopropene dienophiles was explored. For the fluorogenic tetrazine probe, an asymmetric methyl-tetrazine was synthesized from an alkyl nitrile and hydrazine using a recently disclosed metal catalyzed reaction.[24] Previous work has demonstrated that methyl modification lowers the reactivity of tetrazines while simultaneously greatly increasing their stability in physiological media. The tetrazine was appended to the 5' position of a 13mer oligonucleotide using an amide coupling reaction. Adjacent to the tetrazine, an internal fluorescein was included off a terminal thymine base. Despite the flexible linker distance between the resultant tetrazine and fluorescein, significant quenching was observed. For the dienophile probe, methyl-cyclopropene derivatives were appended at the 3' end of oligonucleotides due to their moderate reactivity, high stability, and small size. We have previously shown that methyl-cyclopropene derivatives are stable reaction partners with fluorogenic tetrazines.[22] We compared a reactive methyl-cyclopropene carbamate (cycp1) and a less reactive methyl-cyclopropene carboxyamide (cycp2) to study the influence of intermolecular reactivity on oligonucleotide-templated intramolecular reaction rate. Reaction of the tetrazine probe with the cyclopropene probe in the presence of a DNA template led to a 9.3-fold increase in the peak emission intensity. The quenched tetrazine probes are extremely stable in buffer and cell media at room temperature and 37° C., in line with previous reports on related methyl-terminated tetrazines.

The DNA template was optimized with respect to the template nucleotide gap length between the ligating tetrazine and cyclopropene probe binding sites. A gap of a single nucleotide resulted in the fastest ligation kinetics, and was used for all further experiments. We incorporated flexible linkers in order to minimize possible steric constraints during ligation. The observed distance dependency of the fluorogenic reaction kinetics provides information on the proximity of bound probes, functioning as a molecular ruler.

Probe ligation kinetics were highly dependent on the presence and amount of a matching sequence template. Hybridization buffer containing 1 µM 13mer-fluorescein-tetrazine (13merF15'tet) and 13mer-cyclopropene1 (13mer3'cycp1) showed no appreciable change in fluorescence over time. This is expected, as the reaction rate between the corresponding tetrazine and cyclopropene precursors was measured to be 0.37±0.05 M$^{-1}$s$^{-1}$. At 1 µM concentration of each oligonucleotide probe the reaction half-life was experimentally estimated to be 5 days without template. However, addition of 1 µM of a 27mer template strand resulted in a rapid increase in fluorescence due to template-driven ligation and unquenching of the fluorescein probe. The reaction half-life for the fastest reaction with 13mer3'cycp1 along the DNA template was 36±2 s, with the measured fluorescence signal plateauing after about 200 s, indicating that the reaction was driven to completion. HPLC and high-resolution mass spectrometry confirmed that the reaction led to the ligation products. Based on the disappearance of 13merF15'tet and the appearance of product by LC/MS we estimate the reaction yield to be approximately 92%. Reactant 13merF15'tet and 13mer3'cycp1 probe melting temperatures were significantly lower (57.4 and 50.4° C., respectively) than that of the ligation product (65.8° C.). However, the tetrazine/cyclopropene product melting temperature is 9.7° C. lower than the melting temperature of a 27mer matching DNA sequence (75.5° C.), indicating that the internal reaction product loop has a slight destabilization effect.

Fitting the increase in fluorescence over time to an exponential growth curve, an observed first order rate constant of 0.019±0.001 $s^{-1}$ was determined for the DNA-templated reaction of two 13mer probes. Assuming that the reaction is limited by ligation (given the high concentration of DNA), we can estimate the effective molarity of the intramolecular reaction to be 53 mM. This is in line with previous estimates of DNA template driven covalent reactions.[9] Reaction kinetics did not differ between DNA or RNA templates, adding to the versatility of this reaction. In comparison to the 13mer3'cycp1, carboxamide construct 13mer3'cycp2 reacts slower with the 13merF15'tet in the presence of template. This is expected based on previous studies and the lower second-order rate constant of cycp2 and tet in the absence of DNA (0.003 $M^{-1}s^{-1}$) compared to cycp1. In the presence of DNA template, the first order reaction rate was determined to be $(3.7\pm0.3)\times10^{-4}s^{-1}$, with a half-life of 1882±132 s (31 min) and an estimated effective molarity of 123 mM.

We also determined the effect of shortening the oligonucleotide length of cycp1 probes. The 7mer3'cycp1 bound less avidly to the template (ligation product melting temperature was 59.9° C.), but, at 1 µM, still reacted rapidly with 13merF15'tet with a half-life of 129±38 s. The rate constant increased by increasing the concentration of the reaction components, indicating that the reaction did not behave like a true first order intramolecular reaction, and that the binding of the 7mer with the template likely influenced the reaction rate. Further reduction of the cyclopropene probe length to a 5mer resulted in very weak template binding.

Importantly, these probes worked robustly in cell media containing serum. Preincubation of the probes for several hours in serum containing media did not diminish the intensity of the signal upon template hybridization, demonstrating the utility of stable bioorthogonal handles. This suggests possible diagnostic and imaging applications in live cells or tissue samples. As a proof of concept, we have performed preliminary imaging studies using the synthetic probes and live mammalian cell hosts. Templates were able to trigger turn-on in live cells and significantly increase fluorescence compared to cells where matching sequences were absent. Probe stability is required for tracking cellular processes over time and for limiting background turn-on when detecting less abundant targets. The general practicality of such probes in complex environments could enable exciting opportunities in therapeutic and diagnostic settings.

One of the benefits of in situ probe ligation is the ability to discriminate sequences containing a single nucleotide mismatch in the template oligonucleotide. This is due to the relatively greater impact of a base mismatch on the binding of shorter versus longer probes. We tested whether tetrazine ligation is sensitive enough to discriminate between a single mismatch on the template using previously tested conditions, optimized to 5 mM $MgCl_2$ in Tris-borate buffer at 37° C. The mismatch (T to G) was introduced in the template portion that hybridizes with a cyclopropene probe. We observed a reaction rate reduction by an order of magnitude in the case of a 7mer3'cycp1, but, similar to previous work, only a moderate difference in the 13mer3'cycp1. Additionally, there is 4.5-fold decrease in the reaction rate at 25° C. in cell media/serum conditions using 7mer3'cycp1, indicating the single-mismatch discrimination is possible in physiological media. With respect to signal intensity, this corresponded to an approximate 10-fold drop in signal intensity after 13 min of reaction with mismatched template, at which time the matched template elicited full reaction in buffer. Probes could also be used to detect matched sequences in the presence of competing mismatched sequences. Such selectivity highlights one potential advantage of in situ ligation of oligonucleotides, the ability to discriminate between single mismatches, which may be useful for applications such as SNP discrimination.

The application of bioorthogonal chemistry allows the use of rapidly reacting chemoselective coupling partners without an obligatory increase of background reactions in aqueous buffers or physiological media. Other popular ligation strategies that rely on nucleophilic displacement or redox reactions are limited in their ability to increase ligation rates due to a concomitant increase in background side reactions since biological media contains high concentrations of nucleophiles such as amines and thiols, as well as redox active agents. Indeed, the minimal autohydrolytic turn-on of the 13merF15'tet over a 35-hour period points to this benefit.

Rapid reaction kinetics are important not only in the presence of off-pathway side reactions or cellular degradation, but also because the reaction rate determines the limit of temporal resolution of target oligonucleotide detection. For instance, there is significant interest in monitoring the transcriptional dynamics of RNA synthesis and degradation. Optimal ligation kinetics will match the timescales of such processes, which can be on the order of minutes in live cells. Since these ligations are tunable, optimization of linker length and coupling partners may further improve kinetics.

By confining tetrazine and cyclopropene probes in close proximity without steric hindrance, the oligonucleotide template enforces an effective molarity in the 50-120 mM range, depending on the linker constructs used. This large effective concentration allows reactions to proceed rapidly only in the presence of sequence-specific targets, with minimal background reaction in the absence of templates. Bioorthogonal reaction-dependent fluorescence benefits detection as tetrazines are not prone to autohydrolysis. Reactivity of the system can be tuned by varying the tetrazine, dienophile, oligonucleotide probe length, linker length, and template gap width spanning the reaction space. Future work will further optimize probe properties such as fluorogenic turn-on ratio and reaction rate. Such probes may have a myriad of applications not only in the detection and imaging of DNA and RNA in live cells or biological samples, but also in therapeutic applications such as the delivery and in situ assembly of antisense probes and therapeutic ribozymes

Example 2

Tissue Culture/Cell Growth Conditions

SKBR3 and LS 174T cells were grown in cDMEM media supplemented with 10% fetal bovine serum, 1% L-glutamine, 1% penicillin/streptomycin. Cells were incubated in 5.0% carbon dioxide, 95% humidity at 37° C. Generally, cells were grown in T-75 tissue culture flasks, seeded at densities between 500,000 and 750,000 cells per flask (cells were quantified with the Life Technologies Countess automated cell counter). The cells were trypsinized with TrypLE Express and resuspended in cDMEM. Cells were allowed to incubate for two days before supplementing with $Ac_4$ManNCyc (N-cyclopropeneacetylmannosamine) or $Ac_4$GlcNAz (N-azidoacetylglucosamine). The cells were then analyzed via confocal microscopy and flow cytometry as described below.

Live-Cell Microscopy

The SKBR3 and LS174T cells were incubated for two days in the presence of 100 µM of $Ac_4$ManNCyc and/or 50 µM $Ac_4$GlcNAz on a Lab-Tek chamber slide maintained in cDMEM medium. Treatment of cells with tunicamycin was done by preparing a 0.2 mg/mL stock in DMSO, which was diluted to a final working concentration of 1.2 µM tunicamycin in cDMEM (0.5% DMSO). Cells were washed 3× with phosphate-buffered saline (PBS) and incubated for 1 hour at 37° C. in 10 µM tetrazine-BODIPY TMR-X, 10 µM tetrazine-Alexa flour 488 and/or 15 µM dibenzocyclooctyne (DIBO)-Alexa Fluor 647 in cDMEM. The media was aspirated, and cells were washed twice with PBS before imaging. All photos were collected with an Olympus FV1000 confocal microscope using ImageJ 1.45j software package.

Analysis of Cell Surface Cyclopropenes by Flow Cytometry

After the incubating the adherent SKBR3 cells in 100 µM of $Ac_4$ManNCyc (1.2 µM tunicamycin and/or 1 mM aBn-GalNAc was used in experiments requiring glycosylation inhibitors) they were washed twice in PBS and then incubated in 10 µM of tetrazine-Alexa flour 488 for 1 hour at 37° C. Control cells were not exposed to $Ac_4$ManNCyc and incubated in 10 µM of tetrazine-Alexa flour 488 for 1 hour at 37° C. Cells were then resuspended in 1-2 ml of cDMEM ($5.0 \times 10^5$ to $1.0 \times 10^6$ per ml) using a rubber policeman. The cells were passed through a 25 gauge syringe to ameliorate excessive clumping, and subjected to analysis by flow cytometry using a 200 mW 488 nm blue solid state laser on the Partec Space Flow Cytometer (Partec).

Fluorescence Turn-on Spectroscopy

Mannosamine-cyclopropene ($Ac_4$ManNCyc) and tetrazine-Alexa-Fluor 488 stocks were prepared at 1 and 0.1 mM, respectively, in phosphate-buffered saline (PBS) pH 7.4. Fluorescence turn-on was measured using a Perkin Elmer LD-45 spectrometer, with the excitation wavelength set to 480/5 nm, and emission scanned over 490-620 nm (5-nm slit width) at a rate of 50 nm/min. Reaction conditions were 50 µM tetrazine-Alexa-Fluor 488 and 100 µM $Ac_4$ManNCyc in PBS pH 7.4 buffer at room temperature.

Synthesis of 1,3,4,6-Tetra-O-acety-N-Boc-D-mannosamine 2

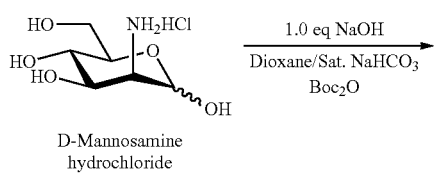

D-Mannosamine hydrochloride

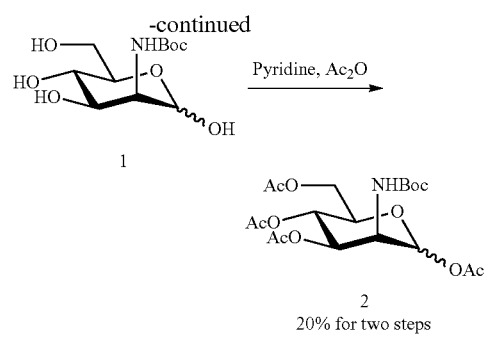

2
20% for two steps

To a stirred solution of D-mannosamine hydrochloride (290 mg, 1.35 mmol) in dioxane/$H_2O$ (4.0 mL/1.0 mL) at room temperature was added NaOH (54 mg, 1.35 mmol) and 1.0 mL sat. $NaHCO_3$. $Boc_2O$ (1.35 mL, 1.0 M in THF, 1.35 mmol) was added to the resulting solution and stirred overnight. By monitoring this reaction with LC-MS, we found the MS of one, two and three Boc products. The reaction solution was evaporated, and the residue dissolved with $CH_2Cl_2$ and filtered, the filtrate was concentrated, and the residue was dissolved in 2.0 mL pyridine. $Ac_2O$ (688 mg, 6.75 mmol) was added to the solution and stirred overnight. The reaction solution was evaporated and the residue was dissolved with EtOAc, then washed by 1.0 M HCl and water. The organic layer was dried over $Na_2SO_4$ and concentrated to afford the crude product. The crude product was purified by flash silica column chromatography (Hexane:EtOAc=2:1, monitored by TLC, stained by $KMnO_4$) to afford 120 mg compound 2 as white foam, in 20% yield over two steps.

$^1$H NMR (400 MHz, $CDCl_3$) δ 1.42 (9H, s), 1.43 (9H, s), 1.97-2.13 (24H, m), 3.72-4.28 (8H, m), 4.88-5.27 (6H, m), 5.80 (1H, s); $^{13}$C (100 MHz, $CDCl_3$) δ 20.88, 20.94, 21.03, 21.08, 28.40, 50.60, 50.85, 62.17, 62.30, 65.60, 65.70, 69.41, 70.29, 71.62, 73.49, 80.27, 80.59, 91.04, 92.23; HRMS $[M+Na]^+$ m/z calculated for $[C_{19}H_{29}NO_{11}Na]^+$ 470.1633. found 470.1636.

Synthesis of 1,3,4,6-Tetra-O-acety-N-cyclopropene tag-D-mannosamine 3

Method 1

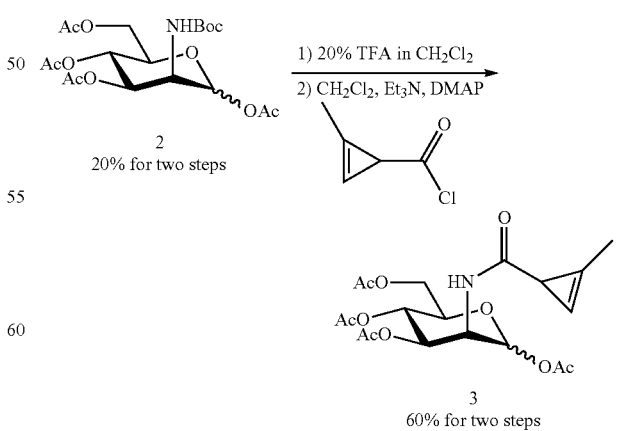

To a stirred solution of 1,3,4,6-tetra-O-acety-N-Boc-D-mannosamine (70.0 mg, 0.16 mmol) in $CH_2Cl_2$ (2.0 mL) at room temperature was added CF₃COOH (0.5 mL). The reaction solution was stirred for 2.0 hours at room temperature and then evaporated to afford 1,3,4,6-tetra-O-acety-D-mannosamine TFA salt. This product could be stained by ninhydrin and formed a red colored spot on the TLC plate which indicated that the product possessed a free —NH₂ group. 1,3,4,6-tetra-O-acety-D-mannosamine TFA salt was dissolved in CH₂Cl₂, after adding Et₃N (32 mg, 0.32 mmol), and DMAP (3.9 mg, 0.032). Methyl cyclopropene acid chloride[1] (4.0 mg, 0.312 mmol) was added and the resulting solution was stirred for 30 minutes at room temperature. LC-MS showed the reaction was finished, and the reaction solution was evaporated to afford the crude product. The crude product was purified by preparative TLC (Hexanes:EtOAc=1:1) to afford 40 mg compound as a white foam, in 60% yield.

Alternative Procedure

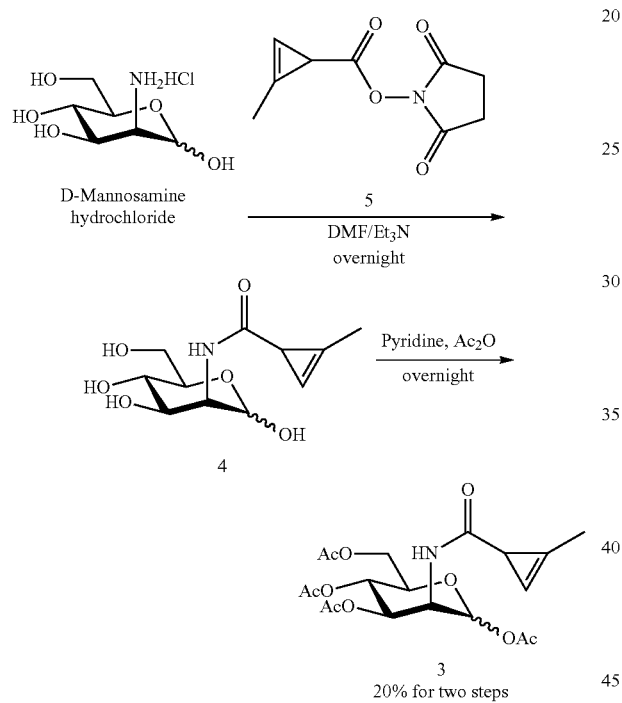

A mixture of D-mannosamine hydrochloride (5.0 mg, 0.023 mmol), N-succinimidyl methyl cyclopropenoate 5 (5.0 mg, 0.026 mmol), and triethylamine (5.0 mg, 0.046 mmol) in DMF (0.3 ml) was stirred at room temperature overnight. The reaction mixture was concentrated in vacuo, and the residue was dissolved in pyridine (0.3 mL) and Ac2O (25 mg) was added. The reaction was stirred at room temperature overnight and then was concentrated in vacuo, the residue was purified by prepared TLC (Hexane/EtOAc=1/1) to afford 2.0 mg of compound 3, in 20% yield.

¹H NMR (400 MHz, CDCl₃) δ 1.97 (32H, m), 3.99-4.07 (4H, m), 4.19-4.22 (2H, m), 4.63-4.68 (2H, m), 5.10-5.16 (2H, m), 5.25-5.31 (2H, m), 5.64-5.72 (2H, m), 5.97-5.98 (2H, m), 6.43 (1H, s), 6.45 (1H, s); ¹³C (100 MHz, CDCl₃) δ 10.70, 10.85, 20.86, 20.90, 20.92, 20.96, 20.98, 21.08, 22.53, 22.56, 49.19, 49.24, 62.14, 62.30, 65.40, 65.66, 69.12, 69.30, 70.25, 92.06, 95.50, 95.99, 113.63, 114.64, 168.44, 169.87, 169.94, 170.26, 170.69, 176.22; HRMS [M+Na]⁺ m/z calculated for [C₁₉H₂₅NO₁₀Na]⁺ 450.1371. found 450.1373.

Synthesis of Tetrazine-Alexa Flour 488

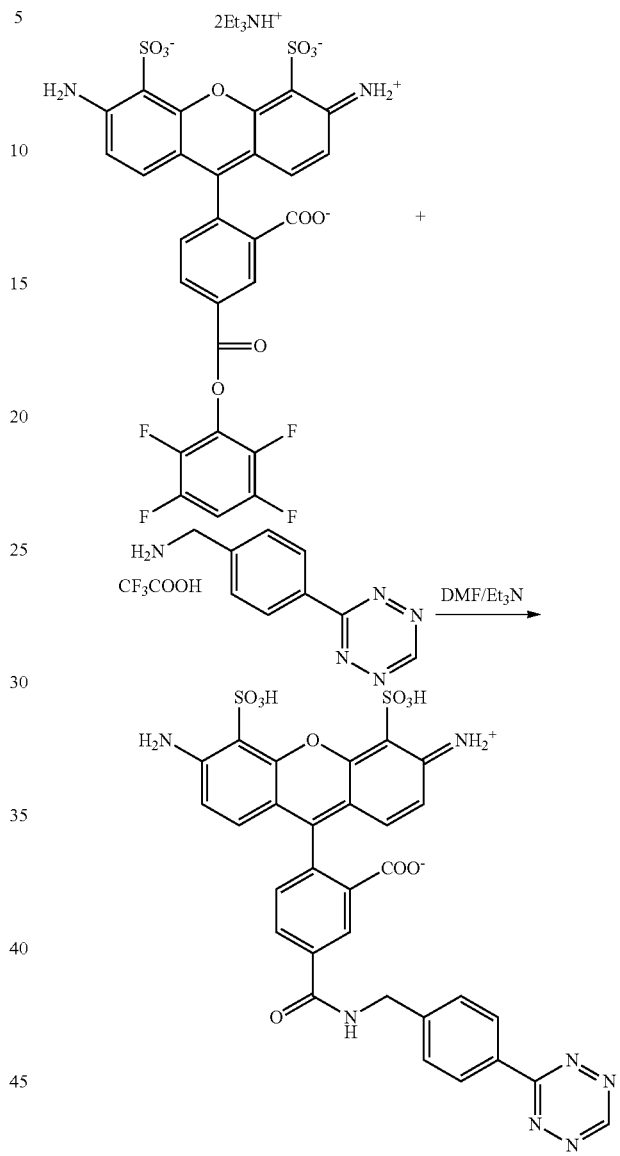

To a stirred solution of Alexa Fluor 488 5-TFP (0.5 mg) in DMF (0.5) at room temperature was added (4-(1,2,4,5-tetrazin-3-yl)phenyl)methanamine[1] (0.5 mg) and Et₃N (0.5 mg). The reaction solution was stirred at room temperature for 30 minutes. The product was purified by reverse phase TLC (MeOH:H₂O=1:3) directly without work-up to afford 0.4 mg product as an orange solid in quantitative yield. HRMS [M−H]⁻ m/z calculated for [C₃₀H₂₀N₇O₁₀S₂]⁺ 702.0719. found 702.0718.

We synthesized unnatural peracetylated mannosamine analog 3 bearing an N-acyl cyclopropene (Ac4ManNCyc) by coupling peracetylated mannosamine to a highly reactive methyl-cyclopropene acid chloride that we previously described. We first protected the amine functional group of mannosamine followed by acetylation of the remaining alcohols, using acetic anhydride, and chromatographic separation. Deprotection of the amine using trifluoroacetic acid yielded peracetylated mannosamine which readily reacted with a highly reactive methyl-cyclopropene acid chloride to yield the desired peracetyled cyclopropene sugar 3. Alternatively, we could also react the primary amine with a methyl-cyclopropene NHS derivative followed by peracetylation (see Supporting information). We chose to utilize the peracetylated derivates given the well known ability of such lipophilic precursors to enter cells and accumulate in glycans, dramatically lowering the requisite concentration of probe the cells are required to be exposed to.

Methyl-cyclopropene amides are known to react slower with tetrazine handles compared to faster methyl-cyclopropene carbamates. However, the reported reaction rates for the methyl-cyclopropene amides are comparable to alternative bioorthogonal reactions used for live-cell imaging. Additionally, the molecular weight of the methyl-cyclopropene amide handle is similar to the azide handles that have been previously used for imaging glycans, making it an attractive derivative. We and others have demonstrated that one of the benefits of tetrazine cycloadditions is the ability to utilize fluorogenic probes that increase in emission intensity after cycloaddition.[36] Indeed, reaction of $Ac_4ManNCyc$ 3 elicits fluorogenic responses from quenched tetrazine probes such as tetrazine-Alexa Fluor 488. Such fluorogenic reactions are valuable for live-cell imaging and can improve the signal to background by diminishing signal from non-specifically bound or trapped fluorescent probes.

In order to determine if $Ac_4ManNCyc$ was incorporated effectively by cells, we incubated adherent human breast cancer (SKBR3) and colon cancer (LS174T) cell lines with 100 µM $Ac_4ManNCyc$ for 48 hours in cell media and serum. After incubation, cells were thoroughly washed and then reacted for 1 hour with 10 µM of fluorogenic Alexa Fluor 488 tetrazine. After a second wash, cells were imaged by confocal microscopy (Olympus FV1000). Cells that were exposed to $Ac_4ManNCyc$ showed bright surface staining while control cells that were not treated with unnatural sugar had a complete absence of staining. In order to ensure that the staining was due to glycan uptake of the probe, we also performed controls by exposing cells to 100 µM $Ac_4ManNCyc$ and inhibiting uptake by using glycosylation inhibitors (ie. tunicamycin and αBnGalNAc) or 20 mM of ManNAc as a competitive substrate.[14] Inhibitors severely diminished staining to levels that were similar to controls. The use of ManNAc as competitor also lowered fluorescent signal, with faint surface staining visible. These experiments provide evidence that the staining patterns are reporting on glycosylation and uptake of the unnatural cyclopropene mannosamine. We also performed additional studies using flow cytometry to quantitate the relative uptake of sugars that corroborated the imaging data. Cells exposed to $Ac_4ManNCyc$ followed by tetrazine imaging probe showed increased fluorescence intensity compared to controls which only received the tetrazine imaging probe.

Finally, we tested whether or not we could simultaneously image two different metabolically incorporated unnatural sugar derivatives, $Ac_4ManNCyc$ and tetraacetylated N-azidoacetylgalactosamine ($Ac_4GalNAz$). The latter unnatural galactosamine azide has been shown to incorporate into O-linked mucins and can be tagged using commercially available fluorescent cyclooctynes (Life Technologies). Recent experimental work has shown that alkenes and azides can be mutually orthogonal to each other, even when using highly strained trans-cyclooctenes. Additionally, the Houk group has calculated that methyl-cyclopropene handles, such as those we have previously developed, should be mutually orthogonal to azide cyclooctyne reactions. We incubated LS174T human colon cancer cells with 100 µM $Ac_4ManNCyc$ and $Ac_4GalNAz$ for 2 days. After incubation, we sequentially stained the cells with 10 µM tetrazine-Alexa Fluor 488 and 15 µM dibenzocyclooctyne (DIBO) 647. Fluorescent microscopy demonstrated cell surface staining in both the fluorescent channels. Similar results were obtained with the SKBR3 cell line. Cells that were incubated with only $Ac_4ManNCyc$ and DIBO 647 or $Ac_4GalNAz$ and tetrazine-Alexa Fluor 488 showed minimal surface staining. The ability to simultaneously label two different metabolically incorporated molecules using live-cell compatible inverse-Diels-Alder and Huisgen reactions expands the capabilities of bioorthogonal metabolic imaging.

The ability of methyl-cyclopropenes to substitute for azides should significantly expand the use of bioorthogonal reactions for metabolic imaging applications. This technology also enables multicolor imaging of two different metabolically incorporated mini-tags. These results highlight the potential utility of cyclopropenes as reactive mini-tags for a myriad of applications in the profiling and imaging of small molecules.

Example 3

General Methods

All chemicals were received from commercial sources and used without further purification. Thin layer chromatography (TLC) was performed on silica gel. Chromatographic purifications were conducted using 40-63 µm silica gel. All mixtures of solvents are given in v/v ratio. $^1H$ and $^{13}C$ NMR spectroscopy was performed on a Varian NMR at 500 ($^1H$) or 125 ($^{13}C$) MHz and a Jeol NMR at 500 ($^1H$) or 125 ($^{13}C$) MHz. All $^{13}C$ NMR spectra were proton decoupled.

Synthetic Methods

1. Synthesis of Cyclopropene Amine 3

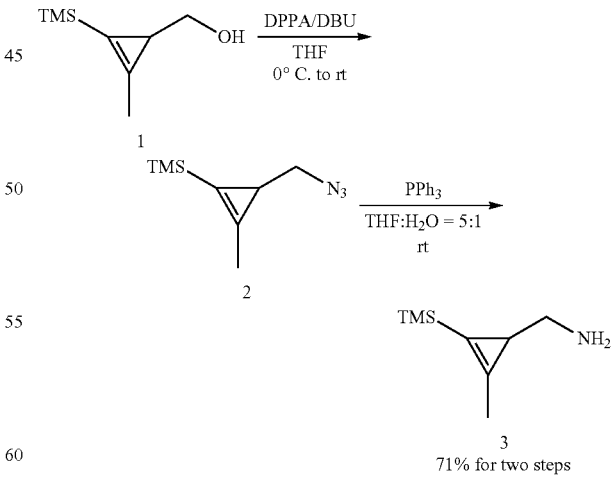

Under the protection of $N_2$, to a stirred solution of cyclopropene alcohol 1 (0.50 g, 3.2 mmol) in dry THF (10.0 mL) at 0° C. was added DBU (0.63 g, 4.2 mmol) followed by DPPA (Diphenylphosphoryl azide, 1.14 g, 4.2 mmol). The reaction solution was slowly warmed to room temperature and stirred overnight. After TLC indicated that the reaction had completed, most of the THF was evaporated by flushing compressed air and the material was passed through a short silica column using hexanes. The product was collected and the hexanes were evaporated by rotary evaporation at 100 torr, room temperature, affording crude cyclopropene azide 2. The crude Cyclopropene azide 2 was dissolved in 5.0 mL THF and 1.0 mL H$_2$O, PPh$_3$ (1.10 g, 4.2 mmol) was added to the solution and stirred at room temperature overnight. After TLC indicated that the reaction was finished, 5.0 mL of 1N HCl was added to the reaction solution. The THF was evaporated and the aqueous solution was extracted with Et$_2$O (5 mL×3). The pH of the water layer was adjusted to pH 9 with sat. NaHCO$_3$ and extracted with CH$_2$Cl$_2$ (10 mL×3). The organic fractions were combined and dried over Na$_2$SO$_4$, evaporated at 100 torr, room temperature to afford 355 mg product as yellow oil in 71% yield over two steps.

Cyclopropene Azide 2

$^1$H NMR (500 MHz, CDCl$_3$) δ 0.17 (s, 9H), 1.57 (m, 1H), 2.22 (s, 3H), 3.01 (dd, J=15, 5 Hz, 1H), 3.14 (dd, J=15, 5 Hz, 1H); $^{13}$C (125 MHz, CDCl$_3$) δ −1.3, 13.8, 18.7, 59.9, 112.5, 134.9.

Cyclpropene Amine 3

$^1$H NMR (500 MHz, CDCl3) δ 0.14 (s, 9H), 1.43 (bs, 1H), 2.18 (s, 3H), 2.57 (bs, 2H); $^{13}$C (125 MHz, CDCl$_3$) δ −0.79, 13.7, 23.5, 48.9, 112.7, 136.9; HRMS [M+H]$^+$ m/z calcd. for [C$_8$H$_{18}$NSi]$^+$ 156.1203. found 156.1204.

Synthesis of Compound 4

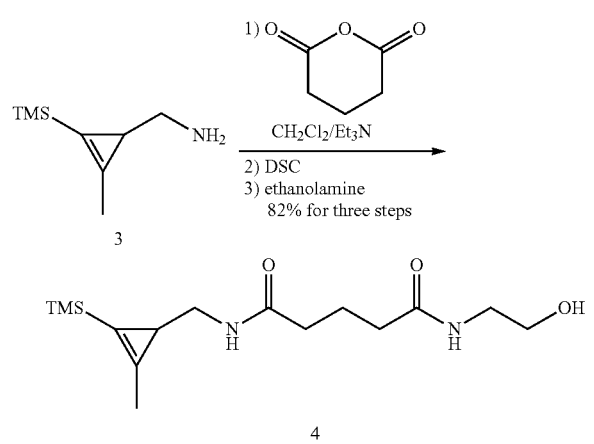

Cyclopropene amine 3 (10.0 mg, 0.065 mmol) was dissolved in CH$_2$Cl$_2$ followed by addition of Et$_3$N (13.0 mg, 0.13 mmol) and glutaric anhydride (11.0 mg, 0.1 mmol). This solution was stirred for 1 hr at room temperature after which N,N'-disuccinimidyl carbonate (26.0 mg, 0.1 mmol) was added. The reaction solution was stirred at room temperature for 1 hour after which ethanolamine (6.0 mg, 0.1 mmol) was added. The resulting solution was stirred for an additional hour at room temperature. After evaporating the organic solvent, the residue was purified by preparative TLC (CH$_2$Cl$_2$/MeOH=10/1) to afford 16.0 mg of compound 4 as a colorless oil, in 82% yield.

$^1$H NMR (500 MHz, CDCl$_3$) δ 0.15 (s, 9H), 1.43 (bs, 1H), 1.97 (bs, 2H), 2.17 (s, 3H), 2.27 (m, 4H), 3.04 (bs, 1H), 3.18 (bs, 1H), 3.41 (bs, 2H), 3.71 (bs, 2H), 5.84 (bs, 1H), 6.73 (bs, 1H); $^{13}$C (125 MHz, CDCl$_3$) δ −0.86, 13.4, 19.3, 22.3, 29.9, 35.5, 42.8, 46.7, 62.4, 111.9, 135.9, 174.4, 176.7; HRMS [M+Na]$^+$ m/z calcd. for [C$_{15}$H$_{28}$N$_2$O$_3$SiNa]$^+$ 335.1761. found 335.1762.

Synthesis of Compound 5

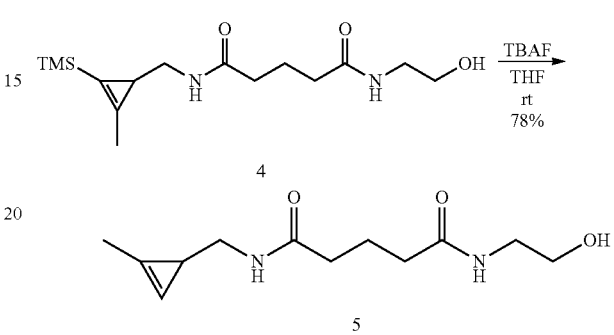

0.05 mL 1.0 M TBAF in THF (0.05 mmol) was added to a stirred solution of compound 4 (15.0 mg, 0.048 mmol) in dry THF (3.0 mL) at room temperature. The reaction solution was stirred at room temperature overnight until the TLC indicated that the starting material was consumed. The organic solvent was evaporated and the residue purified by preparative TLC (CH$_2$Cl$_2$/MeOH=10/1) to afford 9.0 mg compound 5 as colorless oil, in 78% yield.

$^1$H NMR (500 MHz, CDCl$_3$) δ 1.54 (m, 1H), 1.94 (m, 2H), 2.11 (s, 3H), 2.24 (m, 4H), 3.11 (m, 1H), 3.22 (m, 1H), 3.40 (m, 2H), 3.71 (m, 2H), 5.86 (bs, 1H), 6.58 (s, 1H), 6.64 (bs, 1H); $^{13}$C (125 MHz, CDCl$_3$) δ 11.8, 18.0, 22.3, 29.9, 35.6, 42.7, 45.6, 62.4, 103.0, 121.7, 173.0, 174.0; HRMS [M+Na]$^+$ m/z calcd. for [C$_{12}$H$_{20}$N$_2$O$_3$Na]$^+$ 263.1366. found 263.1367.

Synthesis of Compound 6

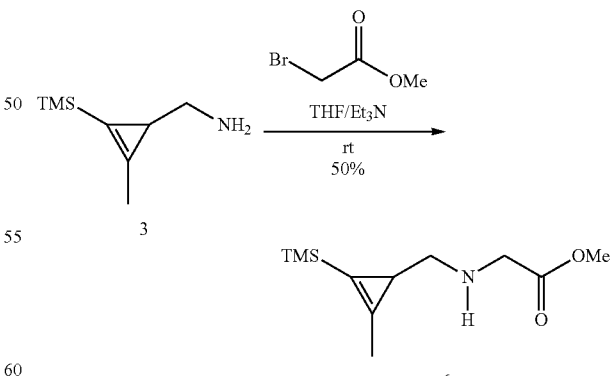

Et3N (101 mg, 1.0 mmol) was added to a stirred solution of compound 3 (130 mg, 0.84 mmol) in dry THF (3.0 mL) at room temperature. After the reaction solution was stirred at room temperature for 1 hour, LC-MS indicated that there was unreacted starting material 3, product 6 and a dialkylation product, with 6 as the majority product. Without workup, the residue was directly purified using preparative TLC (EtOAc) to afford 85 mg compound 6, in 50% yield.

$^1$H NMR (500 MHz, CDCl$_3$) δ 0.16 (s, 9H), 1.44 (t, J=5 Hz, 1H), 2.20 (s, 3H), 2.38 (dd, J=10, 5 Hz, 1H), 2.63 (dd, J=10, 5 Hz, 1H), 3.41 (d, J=24 Hz, 1H), 3.47 (d, J=24 Hz, 1H), 3.72 (s, 3H); $^{13}$C (125 MHz, CDCl$_3$) δ −0.83, 13.6, 20.0, 50.5, 52.0, 57.4, 112.4, 136.6, 173.0; HRMS [M+H]$^+$ m/z calcd. for [C$_{11}$H$_{22}$NO$_2$]$^+$ 228.1414. found 228.1415.

Synthesis of Compound 7

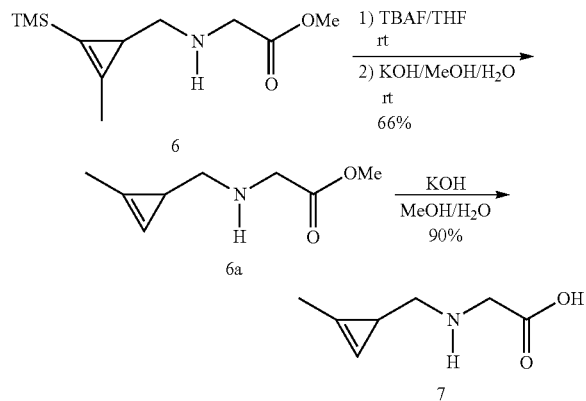

TBAF (0.26 mL, 1.0 M in THF) was added to a stirred solution of compound 6 (60.0 mg, 0.26 mmol) in dry THF (0.25 mL) at room temperature. The reaction solution was stirred at room temperature for 8 hours until the TLC indicated that the starting material was consumed. The solvent was evaporated and the residue was purified by preparative TLC (Hexane/EtOAc=2/1) to afford 27.0 mg compound 6a as colorless oil, in 66% yield. KOH (15 mg, 0.26 mmol) was added to a stirred solution of 6a (20 mg, 0.13 mmol) in 0.5 mL MeOH/H$_2$O (4/1) and the resulting solution was stirred overnight. The pH was adjusted to neutral by adding 0.26 mL 1M HCl and the solution was evaporated to afford the crude product which was purified by preparative TLC (CH$_2$Cl$_2$/MeOH/H$_2$O=10/2/0.2) to afford 16 mg of compound 7 as a white solid, in 90% yield.

Compound 6a $^1$H NMR (500 MHz, CDCl$_3$) δ 1.54 (m, 1H), 2.13 (s, 3H), 2.50 (dd, J=10, 5 Hz, 1H), 2.59 (dd, J=10, 5 Hz, 1H), 3.42 (s, 2H), 3.71 (s, 3H), 6.64 (s, 1H); $^{13}$C (125 MHz, CDCl$_3$) δ 12.1, 18.5, 50.7, 52.0, 56.4, 103.9, 122.3, 173.3.

Compound 7

$^1$H NMR (500 MHz, D$_2$O/DMSO-d$_6$=5/1) δ 1.48 (m, 1H), 2.02 (s, 3H), 2.72 (dd, J=10, 5 Hz, 1H), 2.94 (dd, J=10, 5 Hz, 1H), 3.47 (d, J=15 Hz, 1H), 3.51 (d, J=15 Hz, 1H), 6.65 (s, 1H); $^{13}$C (125 MHz, CDCl$_3$) δ 12.1, 15.0, 49.7, 50.3, 56.1, 102.6, 121.4, 172.2.

Synthesis of Compound 8

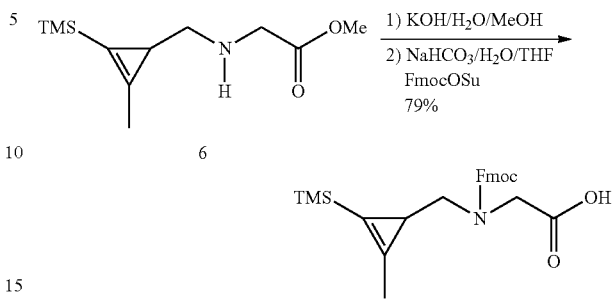

KOH (0.1 mL, 2.0 M KOH/H$_2$O) was added to a stirred solution of compound 6 (20 mg, 0.088 mmol) in MeOH (3.0 mL) at room temperature. The reaction solution was stirred at room temperature for 6 hours after which TLC indicated that the reaction had completed. The organic solvent was evaporated and the residue was dissolved in 2.0 mL THF. HCl (0.2 mL, 1.0 M HCl/H$_2$O) was added followed by NaHCO$_3$ (15 mg in 0.1 mL H$_2$O, 0.18 mmol). FmocOSu (33 mg, 0.1 mmol) was added and the resulting solution was stirred for 3 hours after which TLC indicated that the reaction had finished. The pH was adjusted to 5 by addition of HCl (0.5 mL, 1.0 M HCl/H$_2$O) and the solution was extracted with EtOAc (10 mL×2). The organic layers were combined, dried over Na$_2$SO$_4$, and evaporated to afford the crude product. The product was purified by preparative TLC (EtOAc) to afford 30 mg of compound 8, in 79% yield.

$^1$H NMR (500 MHz, CDCl$_3$) δ 0.13 (s, 9H), 1.39 (bs, 1H), 2.14 (s, 3H), 2.80-2.89 (m, 1H), 3.61-3.68 (m, 1H), 3.88-4.21 (m, 3H), 4.42 (m, 2H), 7.27-7.73 (m, 8H); $^{13}$C (125 MHz, CDCl$_3$) δ −0.85, 13.5, 18.5, 29.9, 47.4, 55.7, 67.7, 111.8, 120.1, 125.1, 127.3, 136.2, 136.3, 141.5, 144.2, 156.0; HRMS [M+Na]$^+$ m/z calcd. for [C$_{25}$H$_{29}$NO$_4$SiNa]$^+$ 458.1758. found 458.1759.

Synthesis of Compound 9

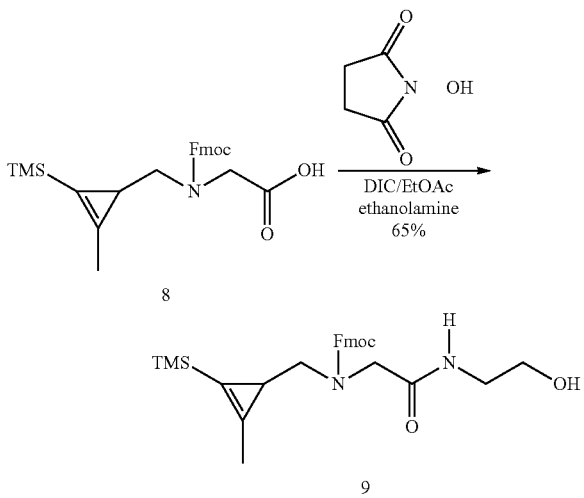

DIC (N,N-diisoprocarbodiimide, 10.0 mg, 0.08 mmol) and N-Hydroxysuccinimide (9.0 mg, 0.08 mmol) was added to a stirred solution of compound 8 (27.0 mg, 0.06 mmol) in EtOAc (2.0 mL) at room temperature. The reaction solution was stirred at room temperature for 30 minutes after which ethanolamine (5.0 mg, 0.08 mmol) was added. After stirring at room temperature for an additional 30 minutes, the reaction solution was washed with water and the organic layer was dried over $Na_2SO_4$ and evaporated. The residue was purified by preparative TLC (EtOAc) to afford 20 mg of compound 9 in 65% yield.

$^1$H NMR (500 MHz, $CDCl_3$) δ 0.14 (s, 9H), 1.34 (bs, 1H), 2.14 (s, 3H), 2.60-2.64 (m, 1H), 3.32-3.39 (m, 2H), 3.63-3.88 (m, 5H), 4.22 (bs, 1H), 4.46-4.52 (m, 2H) 7.30-7.77 (m, 8H); $^{13}$C (125 MHz, CDCl3) δ −1.00, 13.3, 18.5, 29.8, 42.5, 47.4, 56.1, 62.2, 67.8, 111.6, 120.1, 124.9, 127.1, 127.9, 136.0, 141.4, 143.9, 157.1, 170.6; HRMS $[M+Na]^+$ m/z calcd. for $[C_{27}H_{34}N_2O_4SiNa]^+$ 501.2180. found 501.2181.

Synthesis of Compound 9

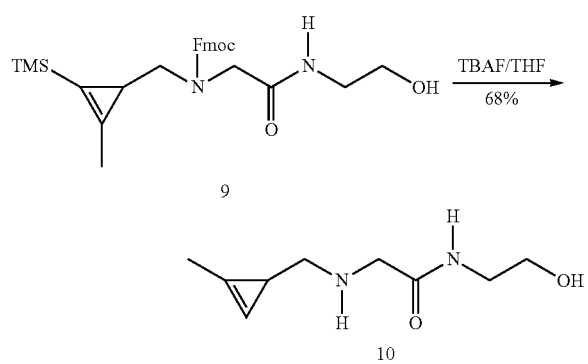

0.12 mL 1.0 M TBAF in THF (0.12 mmol) was added to a stirred solution of compound 9 (19.0 mg, 0.04 mmol) in dry THF (1.0 mL) at room temperature. The reaction solution was stirred at room temperature for 16 hours until the TLC indicated an absence of the starting material and intermediate. The organic solvent was evaporated and the residue was purified by preparative TLC ($CH_2Cl_2$/MeOH/$CF_3COOH$=70/10/0.5) to afford 5.0 mg of compound 10 as a white solid, in 68% yield.

$^1$H NMR (500 MHz, acetone-$d_6$) δ 1.66 (t, J=5 Hz, 1H), 2.13 (s, 3H), 2.94 (dd, J=15, 5 Hz, 1H), 3.09 (dd, J=15, 5 Hz, 1H), 3.38 (bs, 2H), 3.60 (bs, 2H), 4.00 (bs, 2H), 6.78 (bs, 1H), 8.52 (bs, 1H); $^{13}$C (125 MHz, $CDCl_3$) δ 10.4, 13.8, 42.1, 47.6, 54.1, 55.1, 102.0, 120.1; HRMS $[M+Na]^+$ m/z calcd. for $[C_9H_{16}N_2O_2Na]^+$ 207.1104. found 207.1105.

Synthesis of Cyclopropene Aldehyde 10 and Compound 11

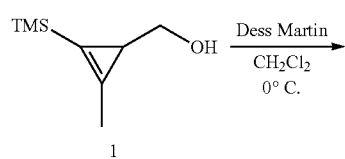

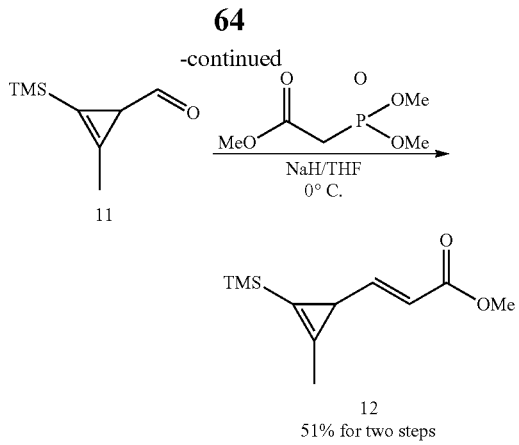

51% for two steps

Dess-Martin reagent (750 mg, 1.75 mmol) was added to a stirred solution of compound cyclopropene 1 (250 mg, 1.6 mmol) in $CH_2Cl_2$ (10.0 mL) at 0° C. The reaction solution was stirred at 0° C. for one hour. The reaction was washed with sodium thiosulfate and sodium bicarbonate aqueous solution three times. The organic layer was collected and dried over $Na^2SO^4$, followed by evaporation at 100 torr. (room temperature). This afforded the crude aldehyde 11. Trimethyl phosphonoacetate (296 mg, 1.6 mmol) was dissolved in 10 mL dry THF and cooled to 0° C., NaH (60% in mineral oil, 64 mg, 1.6 mmol) was added and stirred at 0° C. for 30 minutes. The crude aldehyde was added to the reaction solution and stirred at 0° C. for one hour. The reaction was quenched with water and extracted with EtOAc (20 mL×3). The organic layers were combined and washed with sat. NaCl solution before drying over $Na_2SO_4$. After filtration, the solution was evaporated and the residue purified by flash silica column (Hexane/EtOAc=10/1) to afford 172 mg compound of 12, in 51% yield.

Compound 11

$^1$H NMR (500 MHz, $CDCl_3$) δ 0.21 (s, 9H), 2.18 (d, J=10 Hz, 1H), 2.27 (s, 3H), 8.69 (d, J=10 Hz, 1H); $^{13}$C (125 MHz, $CDCl_3$) δ −1.6, 13.3, 35.2, 105.7, 123.9, 206.2.

Compound 12

$^1$H NMR (500 MHz, CDCl3) δ 0.15 (s, 9H), 2.05 (d, J=10 Hz, 1H), 2.17 (s, 3H), 3.68 (s, 3H), 5.78 (d, J=15 Hz, 1H), 6.64 (dd, J=15, 10 Hz, 1H); +C (125 MHz, $CDCl_3$) δ −1.3, 12.7, 24.2, 51.2, 110.5, 115.0, 130.3, 160.4, 167.8; HRMS $[M+H]^+$ m/z calcd. for $[C_{11}H_{19}O_2Si]^+$ 211.1149. found 211.1150.

Synthesis of Compound 14

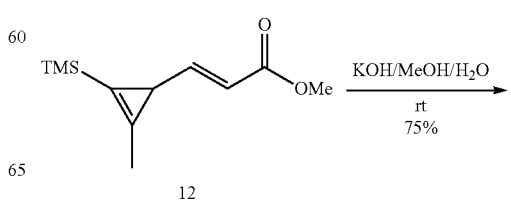

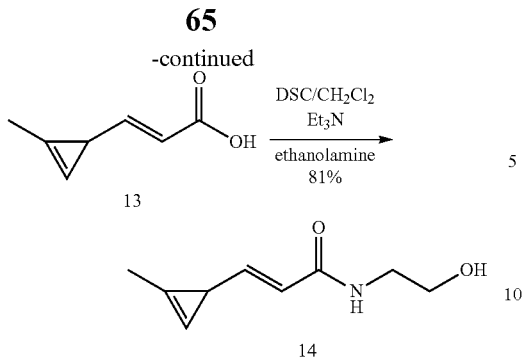

KOH (0.8 mL, 2.0 M KOH/H$_2$O) was added to a stirred solution of compound 12 (100 mg, 0.48 mmol) in MeOH (4.0 mL) at room temperature. The reaction solution was stirred at room temperature overnight. The organic solvent was evaporated and the residue was dissolved in EtOAc and washed with 1M HCl. The organic layer was dried over Na$_2$SO$_4$ and evaporated to afford crude compound 13. The crude product was purified by preparative TLC (CH$_2$Cl$_2$/MeOH=10/1) to afford 44 mg of compound 13 as a colorless oil, in 75% yield. Compound 13 (10 mg, 0.08 mmol) was dissolved in CH$_2$Cl$_2$ and, to this solution, Et$_3$N (10 mg, 0.1 mmol) and DSC (N,N'-Disuccinimidyl carbonate, 26 mg, 0.1 mmol) were added. The resulting solution was stirred for 30 min after which ethanolamine (6 mg, 0.1 mmol) was added. The reaction was stirred at room temperature for an additional 1 hour. The organic solvent was evaporated and the residue was purified by preparative TLC (EtOAc) to afford 11 mg of compound 14 as a colorless oil, in 81% yield.

Compound 13

$^1$H NMR (500 MHz, CDCl$_3$) δ 2.16 (s, 3H), 2.19 (d, J=10 Hz, 1H), 5.86 (d, J=15 Hz, 1H), 6.56 (s, 1H), 6.73 (dd, J=15, 10 Hz, 1H); $^{13}$C (125 MHz, CDCl$_3$) δ 11.3, 22.5, 100.7, 116.3, 118.5, 161.7, 172.1; HRMS [M+H]$^-$ m/z calcd. for [C7H7O2]$^-$ 123.0452. found 123.0453.

Compound 14

$^1$H NMR (400 MHz, CDCl$_3$) δ 2.13 (s, 3H), 2.15 (d, J=8 Hz, 1H), 2.21 (bs, 1H), 3.48 (t, J=6 Hz, 2H), 3.73 (t, J=6 Hz, 2H), 5.85 (d, J=20 Hz, 1H), 5.97 (bs, 1H), 6.53 (dd, J=20, 12 Hz, 1H), 6.56 (s, 1H); $^{13}$C (125 MHz, CDCl$_3$) δ 11.3, 22.0, 42.7, 62.9, 102.3, 118.9, 119.1, 154.7, 167.8; HRMS [M+H]$^+$ m/z calcd. for [C$_9$H$_{13}$NO$_2$Na]$^+$ 190.0838. found 190.0839.

Synthesis of Compound 16

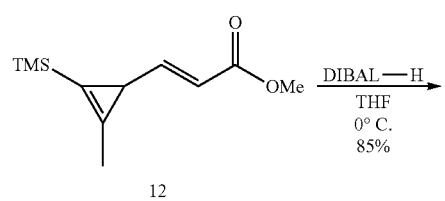

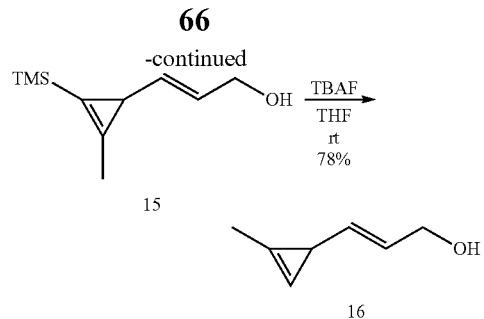

DIBAL-H (1.0M, 0.44 mL) was added to a stirred solution of compound 12 (50 mg, 0.24 mmol) in dry THF (2.0 mL) at 0° C. The reaction was stirred at 0° C. for 1 hour and then quenched by added 0.1 mL water. The solution was filtered and the organic solvent evaporated to afford the crude product. The residue was purified by prepared TLC (hexane/EtOAc=5:1) to give 36 mg of compound 15 as a yellow oil, in 85% yield. Compound 15 (20 mg, 0.11 mmol) was dissolved in 0.3 mL THF and TBAF (1.0 M in THF, 0.12 mL) was added. The solution was stirred at room temperature overnight. The solvent was evaporated and the residue was purified by preparative TLC (Hexane/EtOAc=3:1) to afford 9.0 mg of compound 16 as a yellow oil, in 78% yield.

Compound 15

$^1$H NMR (500 MHz, CDCl$_3$) δ 0.15 (s, 9H), 1.93 (d, J=10 Hz, 1H), 2.16 (s, 3H), 4.04 (d, J=10 Hz, 2H), 5.26 (dd, J=20, 10 Hz, 1H), 5.64 (dd, J=20, 10 Hz, 1H); $^{13}$C (125 MHz, CDCl$_3$) δ −0.91, 12.8, 23.0, 64.3, 111.7, 124.2, 133.1, 143.0.

Compound 16

$^1$H NMR (500 MHz, CDCl3) δ 2.03 (d, J=5 Hz, 1H), 2.12 (s, 3H), 4.07 (d, J=10 Hz, 2H), 5.30 (dd, J=15, 5 Hz, 1H), 5.70 (dd, J=15, 5 Hz, 1H), 6.58 (s, 1H); $^{13}$C (125 MHz, CDCl$_3$) δ 11.3, 21.2, 63.9, 102.3, 120.4, 125.5, 141.7.

In our initial studies exploring the reaction of methyl-cyclopropenes with tetrazines, we noted that the substituents on the C3 position of cyclopropene greatly affect reactivity in inverse Diels-Alder cycloaddition. For instance, the rate of cycloaddition of cyclopropene carbamate 2 is approximately one-hundred times faster than cyclopropene amide 1 when reacting with tetrazine 3 in aqueous solution. We hypothesized that this was due to the C3 methylene group in 2 providing a more electron rich substituent compared to the electron withdrawing C3 carbonyl of amide 1. This would be consistent with prior work which demonstrated that electron rich dienophiles react more rapidly in inverse electron-demand Diels-Alder reactions.[22]

That the reaction rate could be modified so dramatically motivated us to explore how modifying the C3 position of methyl-cyclopropenes affected the kinetics and aqueous stability. Simultaneously, in order to be able to easily introduce these groups to molecules of interest, we explored substituents possessing reactive handles that could be used for further modification. Herein, we report the synthesis of these new methyl-cyclopropene mini-tags.

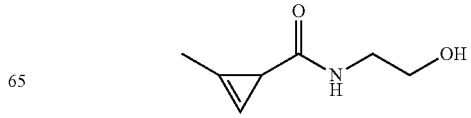

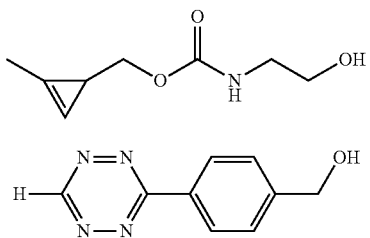

We attempted to form the amine by first converting the alcohol directly to an azide followed by reduction. Treatment with diphenylphosphoryl azide (DPPA) and 1,8-Diazabicyclo[5.4.0]undec-7-ene (DBU) could convert cyclopropene hydroxyl 1 into cyclopropene azide 2 in high yield. After simple purification, the azide could be reduced with triphenylphosphine yielding cyclopropene amine 3. Both cyclopropene azide 2 and amine 3 are volatile and, although useful as synthetic intermediates, were not amenable long-term storage. [0266] However, cyclopropene amine 3 could readily react to form stable amides or secondary amines. For instance, reaction with glutaric anhydride or methylbromoacetate formed the corresponding cyclopropene amide 4 and secondary amine 10. These compounds were amenable to long term storage. The introduced carboxyl handle at could also be further coupled with primary amines such as ethanolamine to afford compounds 5 and 10.

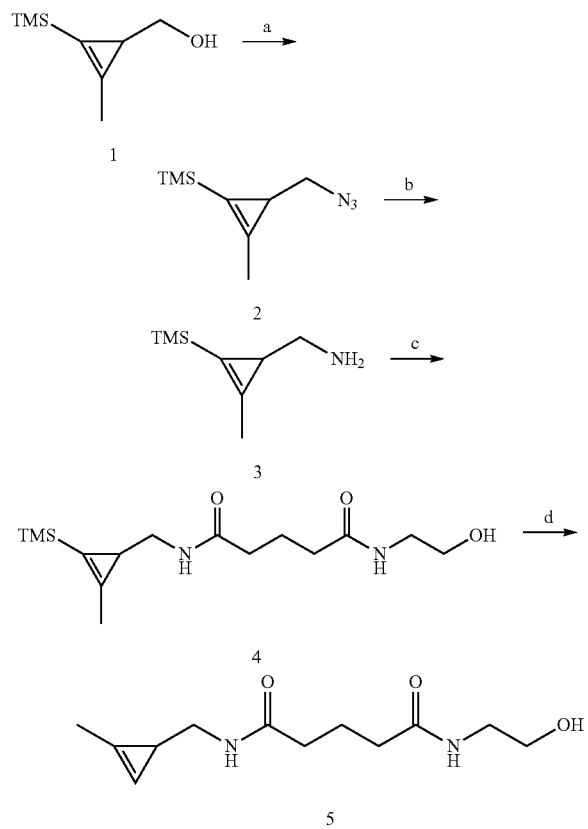

a) DPPA/DBU, THF, 0° C. to rt; b) PPh₃, THF:H₂O = 5:1, rt, 71% from 1; c) Glutaric anhydride, CH₂Cl₂/Et₃N/rt, 30 min; then N,N'-succinimidyl carbonate, 30 min; then ethanol amine, 82%; d) TBAF, THF, rt, 78%.

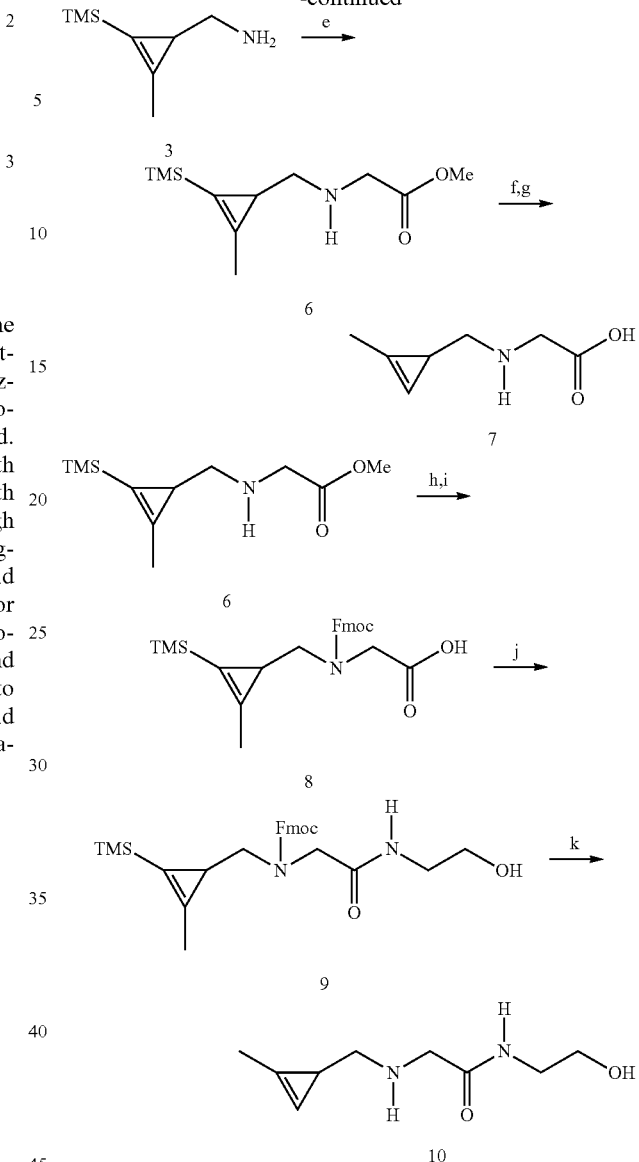

a) Ethylbromoacetate, THF, Et₃N, rt, 50%; b) TBAF, THF, rt; c) KOH, MeOH/H₂O, rt, 51% for two steps; d) KOH, MeOH/H₂O, rt; e) NaHCO₃, H₂O/THF, FmocOSu, rt, 79% for two steps; f) OH—Su,DIC, EtOAc, rt, 1.0 hour then ethanol amine, 65%; g) TBAF, THF, 68%.

We also explored whether cyclopropene alcohol 1 could be converted to an aldehyde via Dess-Martin oxidation. This reaction proved successful, though cyclopropen aldehyde 11 is volatile and unstable, slowly degrading over 48 hours when stored at −20° C. However, aldehyde 11 could be converted to α,β-unsaturated ester 12 through Horner-Wadsworth-Emmons reaction. Selective hydrogenation of the α,β-unsaturated bond proved to be challenging and was not pursued. Simultaneous hydrolysis of the ester and deprotection of the trimethylsilyl group with potassium hydroxide afforded cyclopropene carboxylic acid 13. This agent could react with amines forming stable cyclopropene amides. For instance 13 could coupled to with ethanolamine to form cyclopropene amide 14. Previously, we have shown that eliminating an electron withdrawing carbonyl group can improve the rate of cyclopropene cycloaddition with tetrazine coupling partners. To test the effect of the carbonyl group, we synthesized cyclopropene alcohol 16 through first reducing cyclopropene ester 12 followed by trimethylsilyl deprotection. However, it should be noted that compound 16 was not stable to long-term storage at −20° C., and was used immediately following purification.

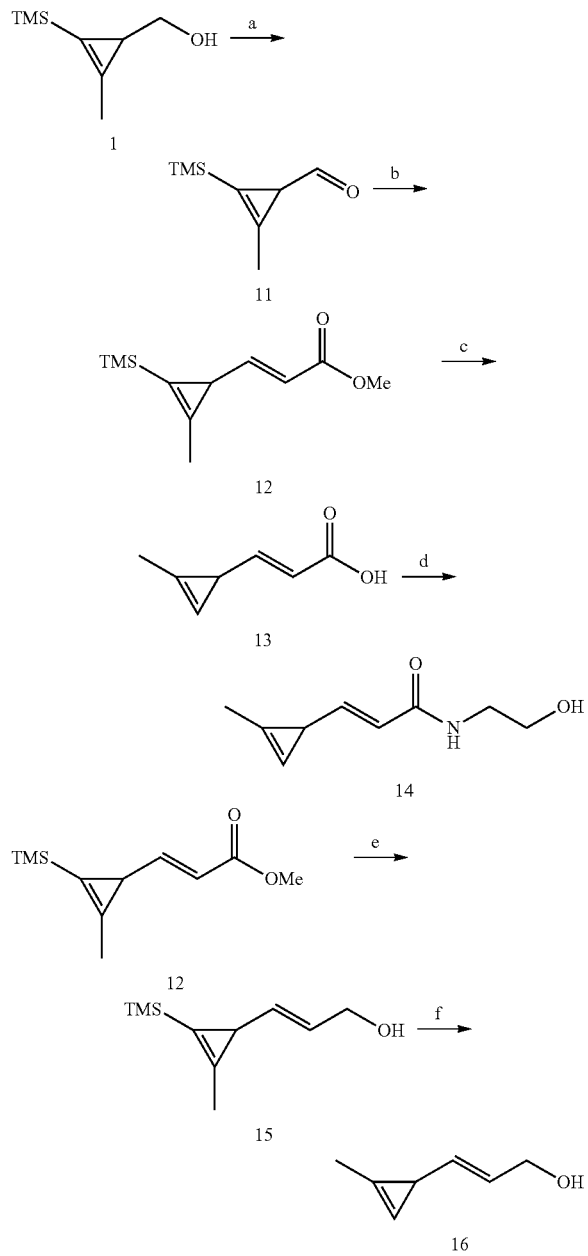

a) Dess-Martin CH2Cl2, 0° C.; b) NaH, trimethyl phosphonoacetate, THF, 0° C., 51% for two steps; c) KOH, MeOH/H2O, rt, 75%; d) N,N′-succinimidyl carbonate, 30 min; then ethanolamine, 81%; e) DIBAL-H, THF, 0° C., 85%; f) TBAF, THF, 0° C., 78%.

After synthesizing the new cyclopropene mini-tags, we next sought to compare their reactivity with tetrazines through inverse Diels-Alder cycloaddition. Additionally, we also assayed their aqueous stability, since methyl-cyclopropene tags are envisioned to find application in bioorthogonal coupling reactions. In order to monitor kinetics, we reacted eight representative methyl-cyclopropenes with 1-methyl-4-aryl tetrazine under pseudo-first order conditions, and tracked the reaction of tetrazine by monitoring the disappearance of the characteristic absorption at 530 nm, similar to previous reports. For stability experiments, we incubated methyl-cyclopropenes in aqueous deuterated solutions (D$_2$O/DMSO-d$_6$=4:1) as indicated.

Of the stable methyl-cyclopropenes, cyclopropene amide (entry 2) is the fastest, with a second order rate constant of 0.74 M$^{-1}$sec$^{-1}$. This rate with methyl tetrazine (19) is approximately twice as fast as the reaction between the previously fastest reported methyl cyclopropene carbamate (entry 3). The methyl-cyclopropene handles derived from aldehyde precursors were slower, and the carboxylic acid (entry 4) proved to be unstable to incubation in aqueous solvent at 37° C. However, conjugation with primary amines to form an amide (entry 5) greatly improved stability, but significantly lowered the rate of reaction with tetrazines. As expected from prior studies, reduction of the precursor ester to the alcohol greatly increased the reaction rate (entry 1), however, the resulting compound is unstable in aqueous solution, completely decomposing in 10.5 hours when dissolved in D$_2$O/DMSO-d$_6$=4:1 at room temperature. The methyl-cyclopropenes resulting from formation of secondary amines showed a reduced rate of reaction with tetrazines in aqueous solvent, though they proved to be stable to decomposition. Finally, cyclopropene amide, was relatively sluggish with respect to tetrazine reactivity, but also proved to be highly stable. For comparison, the rate of reaction of cyclopropene amide is approximately 138 times slower than the fastest stable handle. It should also be noted that the reported reaction rate constants are expected to dramatically change based on the tetrazine handle used. For instance, our previous studies reported the rates of cycloaddition for cyclopropene carbamate and amide with a faster reacting, though less stable, unsubstituted tetrazine and these rates were 36 and 29 fold faster, respectively, than the rates reported with methyl-tetrazine.

Example 4

General Methods

All chemicals were received from commercial sources and used without further purification. Thin layer chromatography (TLC) was performed on silica gel. Chromatographic purifications were conducted using 40-63 μm silica gel. All mixtures of solvents are given in v/v ratio. 1H and 13C NMR spectroscopy was performed on a Varian NMR at 500 (1H) or 125 (13C) MHz and a Jeol NMR at 500 (1H) or 125 (13C) MHz. All 13C NMR spectra were proton decoupled.

General Procedure for Synthesis of 3,6-Dialkyl 1,2,4,5-Tetrazine

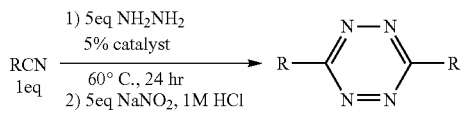

To a 10 mL microwave reaction tube equipped with a stir bar, 0.05 mmol of catalyst, 1.0 mmol of alkyl nitrile, and 0.16 mL (5 mmol) of anhydrous hydrazine was added. The vessel was sealed and the mixture was stirred in an oil bath at 60° C. for 24 hours. After reaction, the seal was removed and the reaction solution was cooled to room temperature (using benzyl cyanide as substrate, 2 mL DMF was added to dissolve the formed solid intermediate). Sodium nitrite (5 mmol, 345 mg) in 5 mL of water was slowly added to the solution and followed by slow addition of 1M HCl during which the solution turned bright red in color and gas evolved. Addition of 1M HCl continued until gas evolution ceased and the pH value is 3. (Caution: this step generates a large amount of toxic nitrogen oxide gasses and should be performed in a well ventilated fume hood). The mixture was extracted with CH2Cl2 and the organic phase dried over sodium sulfate. The solvent was removed using rotary evaporation and the residue purified using silica column chromatography.

3,6-dibenzyl-1,2,4,5-tetrazine: The title product was purified as a purple solid after silica column chromatography (Hexane:EtOAc=20:1). Yield: 70% (Zn(OTf)2); 95% (Ni(OTf)2). 1H NMR (500 MHz, CDCl3) δ 7.39-7.43 (4H, m), 7.29-7.34 (4H, m), 7.22-7.28 (2H, m), 4.60 (4H, s); 13C NMR (125 MHz, CDCl3) δ 169.31, 135.91, 129.34, 129.01, 127.49, 41.35; HRMS [M+H]+m/z calcd. For [C16H15N4]+263.1289. found 263.1291.

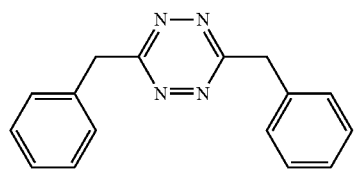 [SMILES: c1ccc(Cc2nnc(Cc3ccccc3)nn2)cc1]

3,6-dipentyl-1,2,4,5-tetrazine: The title product was purified as a red oil after silica column chromatography (Hexane). Yield: 59% (Zn(OTf)2); trace (Ni(OTf)2). 1H NMR (500 MHz, CDCl3) δ 3.29 (4H, t, J=7.5 Hz), 1.89-1.98 (4H, m), 1.32-1.46 (8H, m), 0.91 (6H, t, J=7 Hz); 13C NMR (125 MHz, CDCl3) δ 170.36, 34.82, 31.43, 28.14, 22.45, 14.00; HRMS [M+H]+ m/z calcd. for [C12H23N4]+ 223.1916. found 223.1917.

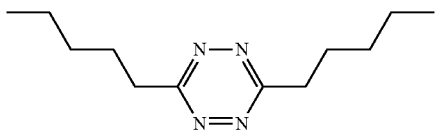 [SMILES: CCCCCc1nnc(CCCCC)nn1]

3,6-di-tert-butyl-1,2,4,5-tetrazine: The title product was purified as a purple solid after silica column chromatography (Hexane). Yield: 25% (Zn(OTf)2); trace (Ni(OTf)2). 1H NMR (500 MHz, CDCl3) δ 1.58 (18H, s); 13C NMR (125 MHz, CDCl3) δ 175.12, 37.88, 29.30; HRMS [M+H]+ m/z calcd. for [C10H19N4]+ 195.1603. found 195.1604.

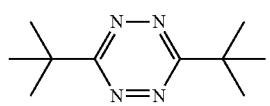

di-tert-butyl((1,2,4,5-tetrazine-3,6-diyl)bis(methylene))dicarbamate: The title product was purified as a red solid after silica column chromatography (hexane:EtOAc=2:1). Yield: 32% (Zn(OTf)2). 1H NMR (500 MHz, CDCl3) δ 1.45 (18H, s), 4.98 (4H, d, J=10 Hz), 5.62 (2H, broad s); 13C NMR (125 MHz, CDCl3) δ 39.01, 51.15, 80.71, 141.01, 150.45; HRMS [M+H]+ m/z calcd. for [C10H19N4]+ 363.1749. found 363.1751.

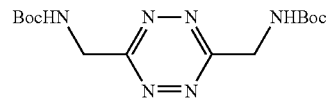

General procedure for synthesis of 3-alkyl-6-aryl or alkyl-1,2,4,5-tetrazine:

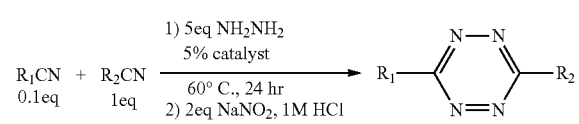

when R1 is N-Boc-pyrrole, the Boc will be deprotected to give pyrrole

To a 10 mL microwave reaction tube equipped with a stir bar, 0.25 mmol of catalyst, 0.26 mL (5.0 mmol) of acetonitrile, and 0.5 mmol of a second nitrile, and 0.8 mL (25.0 mmol) of anhydrous hydrazine was added. The vessel was sealed and the mixture was stirred in an oil bath at 60° C. for 24 or 36 hours. The reaction solution was cooled to room temperature and the seal was removed. Sodium nitrite (10 mmol, 690 mg) in 5 mL of water was slowly added to the solution followed by slow addition of 1M HCl during which the solution turned bright red in color and gas evolved. Addition of 1M HCl continued until gas evolution ceased and the pH value is 3. (Caution: this step generates a large amount of toxic nitrogen oxide gasses and should be performed in a well ventilated fume hood). The mixture was extracted with EtOAc and the organic phase dried over sodium sulfate. The EtOAc was removed using rotary evaporation and the residue purified using silica column chromatography.

tert-butyl((6-methyl-1,2,4,5-tetrazin-3-yl)methyl)carbamate: The title product was purified as a red solid after silica column chromatography (Hexane:EtOAc=5:1). Yield: 36% (Zn(OTf)2); 36% (Ni(OTf)2). 1H NMR (500 MHz, CDCl3) δ 5.57 (1H, N—H, bs), 4.95 (2H, s), 3.08 (3H, s), 1.46 (9H, s). 13C NMR (125 MHz, CDCl3) δ 33.27, 38.99, 51.06, 80.61, 141.01, 149.52, 151.03; HRMS [M+Na]+ m/z calcd. for [C9H16N5O2]+248.1119. found 248.1118.

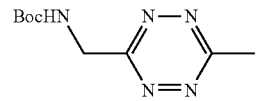

2-(6-methyl-1,2,4,5-tetrazin-3-yl)ethanol: Following the general procedure but the reaction time is 36 hr. The title product was purified as a red liquid after silica column chromatography (Hexane:EtOAc=1:1). Yield: 36% (Zn(OTf)2); 36% (Ni(OTf)2). 1H NMR (500 MHz, CDCl3) δ 1.62 (1H, bs), 3.07 (3H, s), 3.57 (2H, t, J=10 Hz), 4.26 (2H, t, J=10 Hz). 13C NMR (125 MHz, CDCl3) δ 35.07, 48.25, 66.20, 112.98, 152.35, 152.69; HRMS [M+H]+ m/z calcd. for [C9H16N5O2]+ 141.0770, 141.0771.

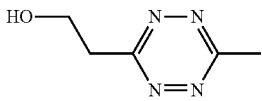

3-methyl-6-pentyl-1,2,4,5-tetrazine: The title product was purified as a red liquid after silica column chromatography (Hexane:EtOAc=10:1). Yield: 40% (Zn(OTf)2); 17% (Ni(OTf)2). 1H NMR (500 MHz, CDCl3) δ 0.92 (3H, t, J=10 Hz), 1.39 (4H, m), 1.93 (2H, m), 3.03 (3H, s) 3.28 (2H, t, J=10 Hz). 13C NMR (125 MHz, CDCl3) δ 27.48, 33.24, 34.22, 38.79, 41.39, 44.12, 150.20, 152.50; HRMS [M+H]+ m/z calcd. for [C9H16N5O2]+ 167.1289. found 167.1291.

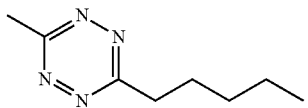

3-benzyl-6-methyl-1,2,4,5-tetrazine: The title product was purified as a red liquid after silica column chromatography (Hexane:EtOAc=10:1). Yield: 40% (Zn(OTf)2); 20% (Ni(OTf)2). 1H NMR (400 MHz, CDCl3) δ 3.01 (3H, s), 4.61 (2H, s), 7.23-7.26 (1H, m), 7.29-7.33 (2H, m) 7.39-7.42 (2H, m); 13C NMR (100 MHz, CDCl3) δ 22.05, 42.13, 128.28, 128.83, 130.13, 168.46, 169.90; HRMS [M+H]+ m/z calcd. for [C9H16N5O2]+ 187.0977, 187.0978.

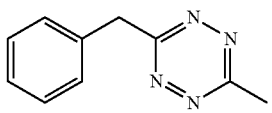

(4-(6-methyl-1,2,4,5-tetrazin-3-yl)phenyl)methanol: The title product was purified as a purple solid after silica column chromatography (Hexane:EtOAc=2:1). Yield: 27% (Zn(OTf)2); 66% (Ni(OTf)2). 1H NMR (500 MHz, CDCl3) δ 3.10 (3H, m), 4.84 (2H, s), 7.58 (2H, m), 8.59 (2H, d, J=10 Hz); 13C NMR (125 MHz, CDCl3) δ 33.38, 68.12, 118.38, 118.94, 121.08, 132.91, 147.50, 150.14; HRMS [M+H]+ m/z calcd. for [C9H16N5O2]+203.0924. found 203.0927.

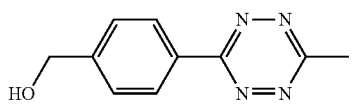

tert-butyl 4-(6-methyl-1,2,4,5-tetrazin-3-yl)benzylcarbamate: The title product was purified as a red solid after silica column chromatography (Hexane:EtOAc=4:1). Yield: 30% (Zn(OTf)2); 68% (Ni(OTf)2). 1H NMR (500 MHz, CDCl3) δ 1.48 (9H, s), 3.09 (3H, s), 4.43 (2H, d, J=5 Hz), 4.97 (1H, bs), 7.50 (2H, d, J=10 Hz), 8.56 (2H, d, J=5 Hz); 13C NMR (125 MHz, CDCl3) δ 32.25, 38.06, 50.80, 79.14, 117.74, 117.84, 119.89, 130.54, 140.12, 146.42, 149.08; HRMS [M+H]+ m/z calcd. for [C9H16N5O2]+ 324.1429, 324.1431.

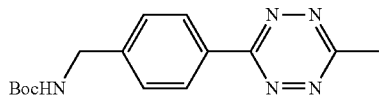

2-(4-(6-methyl-1,2,4,5-tetrazin-3-yl)phenyl)acetic acid: The title product was purified as a purple solid after silica column chromatography (CH2Cl2:MeOH=15:1). Yield: 70% (Zn(OTf)2); 70% (Ni(OTf)2). 1H NMR (500 MHz, CDCl3) δ 3.93 (3H, s), 4.48 (2H, s), 7.47 (2H, d, J=5 Hz), 8.31 (2H, d, J=5 Hz); 13C NMR (125 MHz, CD3OD) δ 35.73, 53.18, 121.99, 124.01, 124.41, 132.35, 151.10, 153.85, 159.56; HRMS [M+H]+ m/z calcd. for [C9H16N5O2]+231.0879, 231.0877.

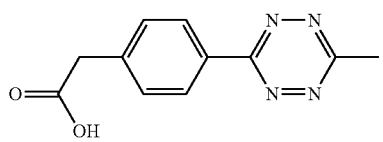 [SMILES: Cc1nnc(-c2ccc(CC(=O)O)cc2)nn1]

3-(4-(iodomethyl)phenyl)-6-methyl-1,2,4,5-tetrazine: The title product was purified as a purple solid after silica column chromatography (Hexane:EtOAc=60:1). Yield: 40% (Ni(OTf)2). 1H NMR (500 MHz, CDCl3) δ 3.10 (3H, s), 7.95 (2H, d, J=10 Hz), 8.32 (2H, d, J=10 Hz); 13C NMR (125 MHz, CDCl3) δ 33.37, 96.57, 119.81, 121.41, 127.25, 147.41, 150.40; HRMS [M+H]+ m/z calcd. for [C9H16N5O2]+298.9788. found 298.9783.

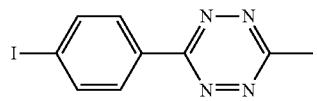

3-methyl-6-(1H-pyrrol-2-yl)-1,2,4,5-tetrazine: The title product was purified as a orange solid after silica column chromatography (Hexane:EtOAc=8:1). Yield: 58% (Ni(OTf)2). 1H NMR (500 MHz, CDCl3) δ 3.00 (3H, s), 6.44 (1H, m), 7.14 (1H, s), 7.41 (1H, m), 9.72 (1H, bs); 13C NMR (125 MHz, CDCl3) δ 22.10, 112.96, 115.57, 125.20, 160.05, 166.66; HRMS [M+H]+ m/z calcd. for [C9H16N5O2]+ 162.0772. found 162.0774.

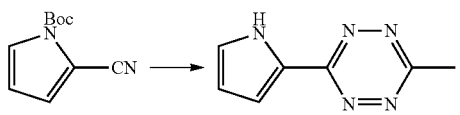

4-(6-methyl-1,2,4,5-tetrazin-3-yl)phenol: The title product was purified as a orange solid after silica column chromatography (Hexane:EtOAc=8:1). Yield: 30% (Ni(OTf)2); 43% (Zn(OTf)2). 1H NMR (500 MHz, CDCl3) δ 3.07 (3H, s), 5.23 (1H, S), 7.03 (2H, d, J=10 Hz), 8.52 (2H, d, J=10 Hz); 13C NMR (125 MHz, CD3OD) δ 20.88, 117.14, 124.30, 130.74, 163.12, 165.18, 167.84; HRMS [M+H]+ m/z calcd. for [C9H16N5O2]+ 189.0771. found 189.0766.

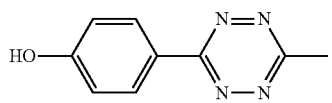

General procedure for synthesis of
3-H-6-aryl-1,2,4,5-tetrazine

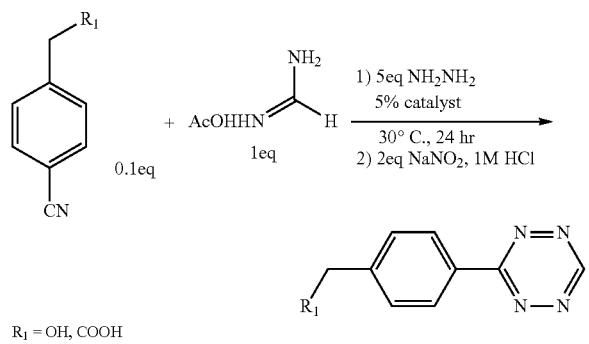

R₁ = OH, COOH

To a 10 mL microwave reaction tube equipped with a stir bar, 0.125 mmol of Ni(OTf)2, 0.27 g (2.5 mmol) of formamidine acetate, benzonitrile (0.25 mmol), and 0.40 mL (12.5 mmol) of anhydrous hydrazine was added. The vessel was sealed and the mixture was stirred at 30° C. for 24 hours. Sodium nitrite (5 mmol, 345 mg) in 5 mL of water was slowly added to the solution and followed by slow addition of 1M HCl during which the solution turned bright red in color and gas evolved. Addition of 1M HCl continued until gas evolution ceased and the pH value is 3. (Caution: this step generates a large amount of toxic nitrogen oxide gasses and should be performed in a well ventilated fume hood). The mixture was extracted with EtOAc and the organic phase dried over sodium sulfate. The EtOAc was removed using rotary evaporation and the residue purified using silica column chromatography.

(4-(1,2,4,5-tetrazin-3-yl)phenyl)methanol: The title product was purified as a red solid after silica column chromatography (Hexane:EtOAc=2:1). Yield: 64% (Ni(OTf)2). 1H NMR (500 MHz, CDCl3) δ 4.87 (3H, s), 7.63 (2H, dd, J=10 Hz, 5 Hz), 8.64 (2H, d, J=10 Hz); 13C NMR (125 MHz, CDCl3) δ 68.00, 118.29, 119.12, 120.85, 133.44, 142.54, 149.37; HRMS [M+H]+ m/z calcd. For [C9H16N5O2]+ 187.0626. found 187.0625.

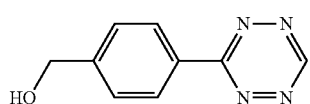

2-(4-(1,2,4,5-tetrazin-3-yl)phenyl)acetic acid: The title product was purified as a red solid after silica column chromatography (CH2Cl2:MeOH=15:1). Yield: 74% (Ni(OTf)2). 1H NMR (500 MHz, CDCl3) δ 3.81 (2H, s), 7.56 (2H, d, J=10 Hz), 8.62 (2H, d, J=10 Hz), 10.23 (1H, s); 13C NMR (125 MHz, CD3OD) δ 52.42, 122.10, 124.02, 124.38, 132.18, 146.12, 152.88, 158.77; HRMS [M+H]+ m/z calcd. for [C9H16N5O2]+217.0717. found 217.0720.

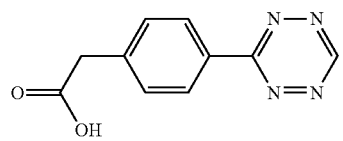

Synthesis of tert-butyl
4-(1,2,4,5-tetrazin-3-yl)benzylcarbamate

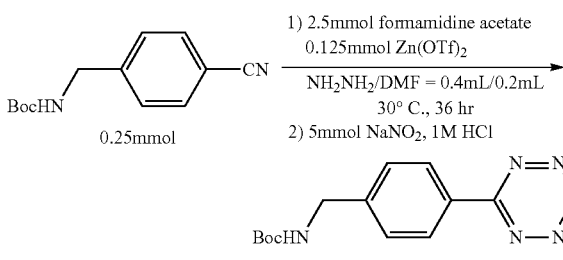

This substrate can't be dissolved in NH2NH2 at room temperature, which resulted in very low yields when using the above reaction conditions. We modified the reaction conditions, using Zn(OTf)2 as catalyst and added a minimal amount of DMF to dissolve the substrate followed by gentle heating at 30° C. for 36 hr, and subsequent work up following the above procedure to recover our desired product in 70% yield.

To a 10 mL microwave reaction tube equipped with a stir bar, 0.125 mmol of Zn(OTf)2, 0.27 g (2.5 mmol) of formamidine acetate, 58 mg (0.25 mmol) nitrile, 0.20 mL DMF, and 0.40 mL (12.5 mmol) of anhydrous hydrazine was added. The vessel was sealed and the mixture was stirred in an oil bath at 30° C. for 36 hours. The reaction solution was cooled to room temperature and the seal was removed. Sodium nitrite (5.0 mmol, 345 mg) in 5 mL of water was slowly added to the solution and followed by slow addition of 1M HCl during which the solution turned bright red in color and gas evolved. Addition of 1M HCl continued until gas evolution ceased and the pH value is 3. (Caution: this step generates a large amount of toxic nitrogen oxide gasses and should be performed in a well ventilated fume hood). The mixture was extracted with EtOAc and the organic phase dried over sodium sulfate. The EtOAc was removed using rotary evaporation and the residue purified using silica column chromatography (Hexane:EtOAc=7:1) to give 50 mg product as red solid, the yield is 70%. 1H NMR (500 MHz, CDCl3) δ 1.49 (9H, s), 4.45 (2H, d, J=5 Hz), 4.97 (1H, bs), 7.53 (2H, d, J=10 Hz), 8.60 (2H, d, J=10 Hz), 10.21 (1H, s); 13C NMR (125 MHz, CDCl3) δ 39.07, 51.82, 118.84, 119.19, 120.76, 132.11, 141.12, 142.56, 149.36; HRMS [M+Na]+ m/z calcd. for [C9H16N5O2]+ 310.1276. found 310.1274.

General procedure for synthesis of 3-H-6-aryl-1,2,4,5-tetrazine using trimethylsilyl cyanide as a nitrile source.

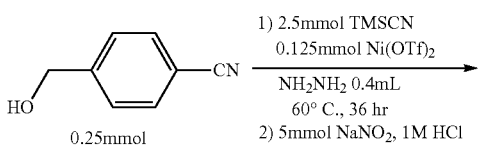

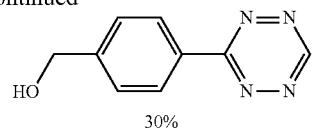

30%

To a 10 mL microwave reaction tube equipped with a stir bar, 0.125 mmol of Ni(OTf)2, 33 mg 4-(hydroxymethyl)benzonitrile (0.25 mmol), 0.40 mL (12.5 mmol) of anhydrous hydrazine, and 0.25 g (2.5 mmol) of trimethylsilyl cyanide was added. The vessel was sealed and the mixture was stirred in an oil bath at 60° C. for 36 hours. The reaction solution was cooled to room temperature and the seal was removed. Sodium nitrite (5 mmol, 345 mg) in 5 mL of water was slowly added to the solution and followed by slow addition of 1M HCl during which the solution turned bright red in color and gas evolved. Addition of 1M HCl continued until gas evolution ceased and the pH value is 3. (Caution: this step generates a large amount of toxic nitrogen oxide gasses and should be performed in a well ventilated fume hood). The mixture was extracted with EtOAc and the organic phase dried over sodium sulfate. The EtOAc was removed using rotary evaporation and the residue purified using silica column chromatography (Hexane:EtOAc=2:1) to give 14 mg product, yield is 30%.

Given the high yields obtained with nickel and zinc triflates, we tested their effect on the yields of several other tetrazine syntheses where at least one component was an alkyl nitrile. In each instance we tested either Ni(OTf)$_2$ or Zn(OTf)$_2$ for catalytic effect. In general we observed that zinc salts gave higher yields for less active nitriles such as those that were sterically hindered or affected by electron-donating groups. On the other hand, more reactive nitriles benefited from the use of nickel salts. However, there were exceptions and it is suggested that both catalysts be tried when attempting synthesis of new tetrazines. For the synthesis of symmetric 3,6-dialkyl 1,2,4,5-tetrazines, yields ranged from 95% for 3,6-dibenzyl-1,2,4,5-tetrazine (entry 1) to 24% for the sterically hindered 3,6-di-tert-butyl-1,2,4,5-tetrazine (entry 3). The moderate yield for the latter tetrazine is impressive given that all previous attempts to synthesize the molecule have only led to trace isolated yield.

The scope of this method extends to asymmetric 3,6-disubstituted 1,2,4,5-tetrazines, which are among the most challenging tetrazines to synthesize. Metal ions could readily promote the formation of 6-methyl-terminated tetrazines from acetonitrile and aromatic nitriles in 40-70% yield. Alkyl nitriles and acetonitrile could also combine with hydrazine to yield 6-methyl-terminated alkyl tetrazines in 36-40% yield. Several of these tetrazines possess functional group handles to facilitate their use in biological applications. For instance, it has recently been demonstrated that methyl-terminated tetrazines are highly stable partners in bioorthogonal cycloadditions and can be used in a mutually orthogonal fashion with azide-alkyne cycloadditions. 6-Methyl-terminated tetrazines were previously only accessible from reactive precursors such as imidates and amidine salts and in lower yield. Dialkyl asymmetric tetrazines with bulkier substituents are extremely difficult to isolate, even from imidates and amidines. In contrast, we were able to isolate 3-benzyl-6-pentyl-1,2,4,5-tetrazine from benzyl cyanide and excess hexanenitrile, albeit in lower yield (12%).

Several groups have measured the rate of cycloaddition between various tetrazines and strained dienophiles such as norbornene and trans-cyclooctene. The substituents on the 3 and 6 positions of 1,2,4,5-tetrazines have a significant affect on the kinetics of the reaction. While 6-methyl-terminated tetrazines benefit from stability, tetrazines terminated with hydrogen at the 6 position react much faster and have proven utility in live cell and live animal applications where lowered concentrations of labeling agent are typically used. With this in mind, we examined if metal catalysis could improve synthetic routes to hydrogen-terminated monoaryl tetrazines. We found that an excess of trimethylsilyl cyanide can be used along with an aromatic nitrile to yield a hydrogen-terminated asymmetric tetrazine. This is the first example of using trimethylsilyl cyanide to synthesize tetrazines and is possible due to the addition of nitrile-activating metal catalysts. Additionally, we explored the effect of Ni(OTf)$_2$ and Zn(OTf)$_2$ on the synthesis of tetrazine from aromatic nitriles and formamidine salts. Although these reactions do not require catalysis, yields are typically low, between 10-20%.[35] Interestingly, we found that metal ions could promote the reaction and significantly increase the yield of tetrazine, which was 60-74% depending on the precursors and catalyst used. This improved methodology will be highly useful to researchers interested in performing rapid bioorthogonal couplings.

Example 5

Starting Materials

All chemicals were received from commercial sources and used without further purification. Thin layer chromatography (TLC) was performed on silica gel. Chromatographic purifications were conducted using 40-63 µm silica gel. All mixtures of solvents are given in v/v ratio. $_1$H and $_{13}$C NMR spectroscopy was performed on a Varian NMR at 400 ($_1$H) or 100 ($_{13}$C) MHz and a Jeol NMR at 500 (1H) or 125 (13C) MHz. All 13C NMR spectra were proton decoupled.

Synthesis of Cyclopropene 2

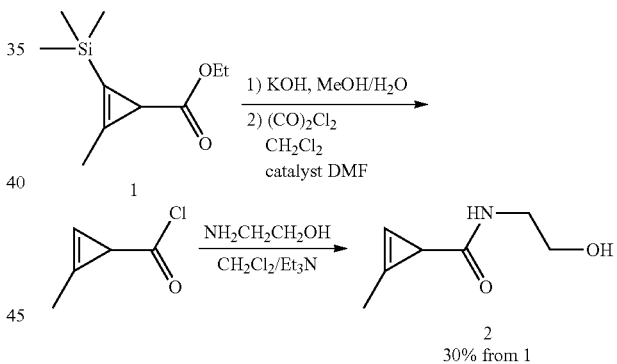

30% from 1

Compound 1 was synthesized according to a previously reported method (Cho, Suk H. and Liebeskind, Lanny S., *J. Org. Chem*, 52, 2631-4, 1987) and was obtained in 70% yield. To a stirred solution of compound 1 (213.0 mg, 1.0 mmol) in MeOH (4.0 mL) at 0° C. was slowly added a solution of KOH (140.0 mg, 2.5 mmol) in H$_2$O (1.0 mL) dropwise. After all the KOH was added, the reaction mixture was stirred overnight at room temperature before it was diluted with 10 mL H$_2$O and extracted with EtOAc (10 mL×2). The pH value of the aqueous layer was adjusted to 3 by addition of 1M HCl, then extracted with EtOAc (10.0 mL×3), the combined organic layer was dried over Na$_2$SO$_4$ and evaporated to afford the crude methyl cyclopropene acid 72 mg as a colorless oil.

The crude acid was dissolved in 5 mL CH$_2$Cl$_2$ and one drop of DMF was added, followed by (CO)$_2$Cl$_2$ (126 mg, 1.0 mmol). The resulting solution was stirred for 2 hours at room temperature and then evaporated to afford the crude methyl cyclopropene acid choride.

To a stirred solution of ethanolamine (61 mg, 1.0 mmol) and Et$_3$N (101 mg, 1.0 mmol) in CH$_2$Cl$_2$ (2 mL) was added a solution of the above methyl cyclopropene acid chloride in CH$_2$Cl$_2$ (2 mL). The resulting reaction solution was stirred for 1 hour at room temperature and then evaporated to afford the crude product. The residue was purified using preparative TLC (EtOAc/Hexane=1.5:1) to afford 42 mg of compound 2. The overall yield is 30% from compound 1.

$_1$H NMR (500 MHz, CDCl3) δ 2.03 (1H, d, J=5 Hz), 2.18 (3H, d, J=5 Hz), 2.98 (1H, bs), 3.43 (2H, t, J=5 Hz), 3.71 (2H, t, J=5 Hz), 5.90 (1H, bs), 6.44 (1H, s); $_{13}$C NMR (125 MHz, CDCl3) 10.70, 22.35, 42.63, 62.41, 95.91, 113.57, 177.71; HRMS [M+Na]$_+$ m/z calcd. for [C$_7$H$_{11}$NO$_2$Na]$_+$ 164.0682. found 164.0684.

Synthesis of (2-methyl-3-(trimethylsilyl)cycloprop-2-en-1-yl)methanol 4

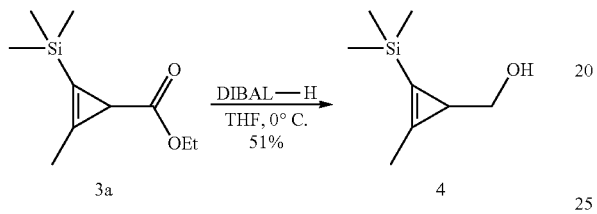

To a stirred solution of compound 1 (2.0 g, 10.0 mmol) in dry THF (25.0 mL) at 0° C. was slowly added a solution of 1.0 M LiAlH$_4$ in THF (25.0 mL, 25.0 mmol) dropwise. After addition of LiAlH$_4$, the reaction mixture was stirred 3 hours at 0° C. before it was quenched with H$_2$O carefully. The precipitate was filtered and the filtrate was concentrated to give the crude product. The residue was purified by flash silica column chromatography (Hexane/EtOAc=5:1) to afford 0.8 g compound 4 as a colorless oil in 51% yield. $_1$H NMR (500 MHz, CDCl$_3$) δ 0.17 (9H, s), 1.57 (1H, t, J=5 Hz), 2.22 (3H, s), 3.48 (2H, d, J=5 Hz); $_{13}$C NMR (100 MHz, CDCl$_3$) 0.99, 13.56, 22.25, 69.60, 111.48, 135.86.

Synthesis of Cyclopropene 5

Carbonyldiimidazole (CDI; 88 mg, 0.55 mmol) was added to a stirred solution of compound 4 (70 mg, 0.45 mmol) in dry THF (3.0 mL) at room temperature. The resulting solution was stirred for 3 hours and then ethanolamine (34 mg, 0.55 mmol) was added. The reaction solution was stirred overnight at room temperature and then evaporated to afford the crude product. The residue was purified by preparative TLC (Hexane/EtOAc=2:1) to afford 0.08 g compound 4a as colorless oil. The above compound 4a was dissolved in dry THF (3.0 mL), followed by addition of 1.0 M TBAF in THF (0.5 mL, 0.5 mmol). The reaction solution was stirred at room temperature overnight until no starting material could be observed by TLC. The reaction solution was evaporated and purified by preparative TLC (Hexane/EtOAc=1/1) to afford 71 mg of compound 5 as a colorless oil. Overall yield is 93% starting from compound 4.

Compound 4a

1H NMR (500 MHz, CDCl$_3$) δ 0.11 (9H s), 1.50 (1H, t, J=5 Hz), 2.15 (3H, d, J=5 Hz), 3.21 (1H, bs), 3.30 (2H, dd, J=10 Hz, 5 Hz), 3.66 (2H, bs), 3.81 (1H, bs), 3.90 (1H, dd, J=10 Hz, 5 Hz), 5.29 (1H, bs); $_{13}$C NMR (125 Hz, CDCl$_3$) 14.29, 25.87, 30.10, 50.03, 64.99, 74.28, 104.07, 122.91, 141.60.

Cyclopropene 5

$_1$H NMR (500 MHz, CDCl$_3$) 1.61 (1H, t, J=5 Hz), 2.10 (3H, d, J=5 Hz), 3.16 (1H, bs), 3.30 (2H, dd, J=10 Hz, 5 Hz), 3.67 (2H, d, J=5 Hz), 3.90 (2H, d, J=5 Hz), 5.35 (1H, bs), 6.54 (1H, s); $_{13}$C NMR (125 Hz, CDCl$_3$) 24.65, 29.05, 50.09, 65.13, 73.43, 97.04, 111.85, 141.58; HRMS [M+Na]+m/z calcd. for [C$_8$H$_{13}$NO$_3$Na]$_+$ 194.0788. found 194.0789.

Synthesis of Lipid Cyclopropene 7

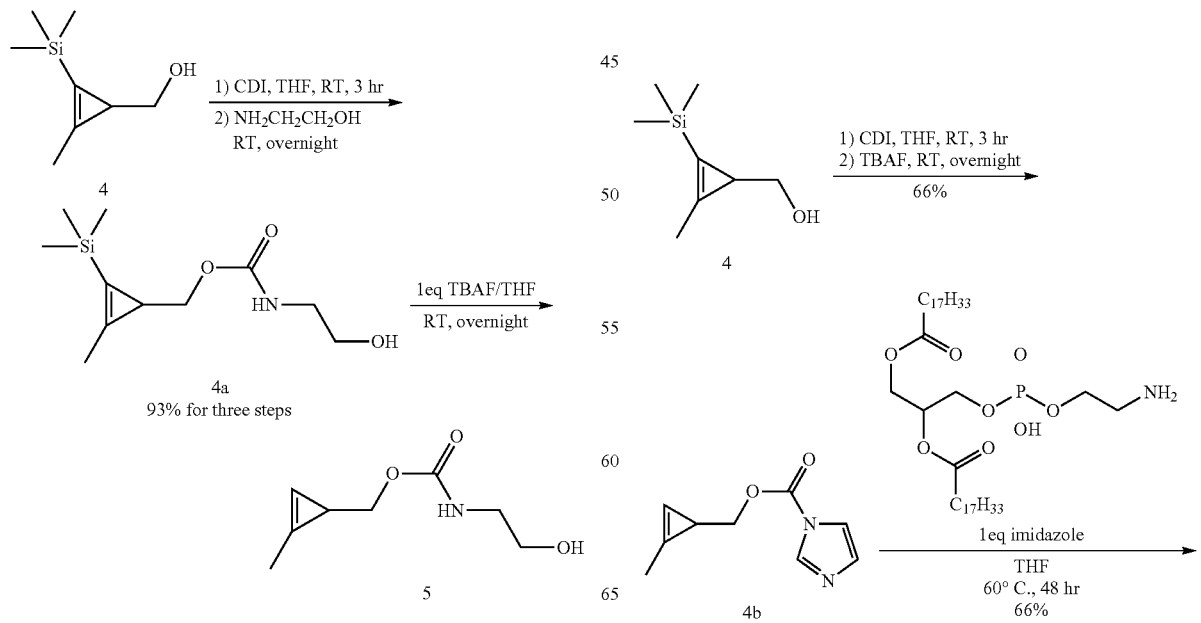

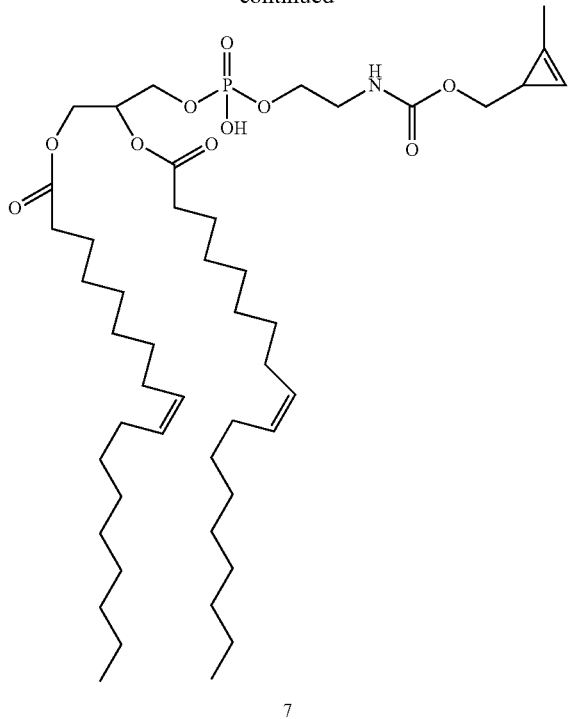

7

To a stirred solution of compound 4 (200 mg, 1.03 mmol) in dry THF (10.0 mL) at room temperature was added CDI (176 mg, 1.10 mmol). The resulting solution was stirred for 3 hours and then 1M TBAF in THF (1.1 mL, 1.10 mmol) was added. The reaction solution was stirred overnight at room temperature and then evaporated to afford the crude product. The residue was purified by flash silica column chromatography (Hexane/EtOAc=1:1) to afford 110 mg compound 4b as a colorless oil in 66% yield. The above compound 4b was dissolved in dry THF (5.0 mL) and followed by addition of 1,2-dioleoyl-sn-glycero-3-phospho-ethanolamine (DOPE) lipid (200 mg, 0.27 mmol) and imidazole (45 mg, 0.66 mmol). The reaction solution was stirred at 60° C. for 48 hours. The reaction solution was evaporated and the residue dissolved with 20 mL EtOAc and washed with 1 M HCl (20 mL×2), dried over the organic layer with $Na_2SO_4$ and evaporated to afford the crude product. The residue was purified by flash silica column chromatography ($CH_2Cl_2$/MeOH=10/1) to afford 150 mg compound 7 as colorless oil in 66% yield.

Compound 4b $_1$H NMR (500 MHz, $CDCl_3$) δ 1.78 (1H, t, J=5 Hz), 2.16 (3H, d, J=5 Hz), 4.25 (1H, dd, J=10 Hz, 5 Hz), 4.33 (1H, dd, J=10 Hz, 5 Hz), 6.60 (1H, s), 7.07 (1H, s), 7.44 (1H, s), 8.55 (1H, s); $_{13}$C NMR (125 Hz, $CDCl_3$) 11.68, 16.72, 76.22, 101.67, 117.22, 120.11, 130.56, 137.79.

Lipid cyclopropene 7

$_1$H NMR (500 MHz, $CDCl_3$) δ 0.87 (6H, t, J=10 Hz), 1.25-1.31 (40H, m), 1.57-1.59 (5H, m), 2.00 (8H, m), 2.11 (3H, s), 2.88 (4H, dd, J=20 Hz, 10 Hz), 3.38 (2H, bs), 3.88 (2H, bs), 3.93 (2H, bs), 3.97 (2H, bs), 4.13 (1H, m), 4.37 (1H, m), 5.22 (1H, bs), 5.33 (4H, m), 5.96 (1H, bs), 7.44 (1H, s), 6.55 (1H, s); $_{13}$C NMR (125 Hz, $CDCl_3$) 29.40, 31.34, 33.73, 38.21, 39.98, 41.84, 43.52, 43.88, 47.25, 53.12, 70.20, 71.50, 72.40, 76.20, 77.93, 101.90, 116.52, 123.58, 123.73, 123.82, 123.99, 145.96, 158.59, 158.75; HRMS [M−H]− m/z calcd. for $[C_{47}H_{83}NO_{10}P]_-$ 852.5760. found 852.5757.

Stability of Cyclopropene 5

Cyclopropene 5 was kept at 37° C. in $D_2O$: DMSO-$d_6$=10:1 and $_1$H NMR was taken over a period of 24 h at the following time points: 0.0, 0.5, 1.0, 1.5, 3.0, 6.0 and 24.0 h. By comparing the peak abundance of the cyclopropene alkene proton (6.21 ppm) at different time points, we determined the stability of cyclopropene 5 (Figure S2).

HPLC Characterization of the Reaction Between Tetrazine-BODIPY FL 6 with Cyclopropene 5

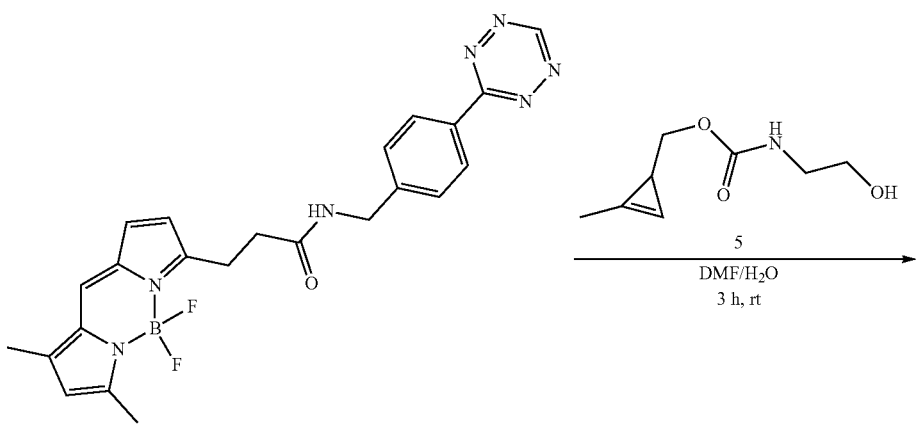

6

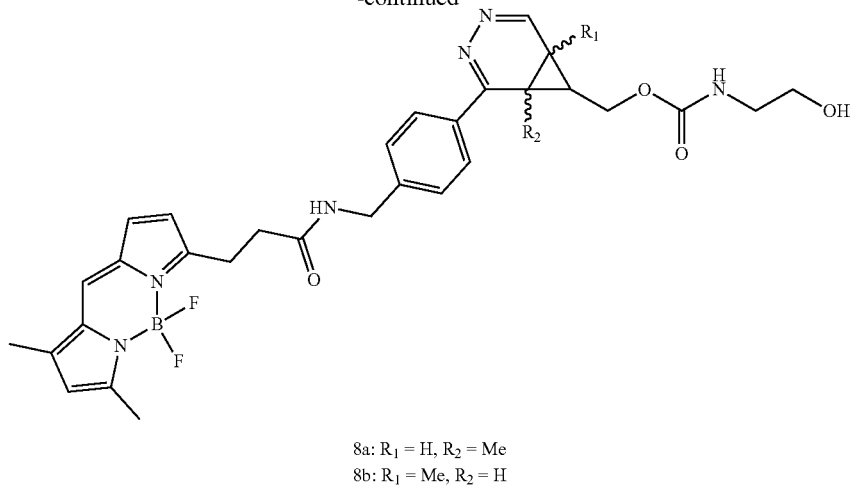

8a: R$_1$ = H, R$_2$ = Me
8b: R$_1$ = Me, R$_2$ = H

Tetrazine-BODIPY FL 6 (1.0 mM in dry DMF, 20 μL) and Cyclopropene 5 (1.0 mM in H$_2$O, 20 μL) were combined in 210 μL of H$_2$O at a final concentration of 0.08 mM for tetrazine-BODIPY FL 6. The reaction solution was agitated for 3 hours at room temperature and then analyzed by LC-MS. Multiple peaks were identified with molecular mass corresponding to diazonorcaradiene adducts (m/z 605 [M+H]$_+$). The multiple peaks are expected given the previously demonstrated potential to form several isomeric products. The reaction, based on the remaining signal from the tetrazine-BODIPY FL 6, went to completion.

Fluorescence Unquenching Measurements

Freshly-purified tetrazine-BODIPY FL 6 was dissolved in DMF and reacted with 10-fold excess cyclopropene 5 at the final concentrations of 10 μM tetrazine and 100 μM cyclopropene in 1% v/v DMF/ddH$_2$O. The reaction mixture was kept at room temperature (20° C.). Emission scans were recorded using a Perkin Elmer LD-45 spectrometer, with the excitation wavelength of 470 nm (2.5-nm slit width), and emission signal was tracked over the 485-640 nm range (5.0-nm slit width). Emission was measured over time and compared against a control sample lacking cyclopropylene. There was no emission change observed over the initial 2 h timeframe for the control sample. The resulting unquenching of the BODIPY FL fluorescence increased as measured at 30, 90, and 120 min intervals. The measurements were stopped after 2 h, as the rate of change in fluorescence peak intensity was decreasing.

Reaction Rate Determination

A tetrazine 3 stock solution was prepared in DMSO and used to prepare tetrazine solutions at 0.6 mM final concentration in 12% v/v DMSO in ddH$_2$O. Reactions were initiated with excess cyclopropene at final concentrations of 6.0, 8.0, and 10.0 mM. The disappearance of the tetrazine absorption peak at 520 nm was tracked over the reaction timeframe by measuring the absorption spectra using a NanoDrop 2000c spectrophotometer (Thermo Scientific). Samples were placed in a quartz cuvette with 10-mm pathlength and stirred at the maximum speed setting of the instrument. The temperature was uncontrolled by the instrument for room temperature (20° C.) measurements, and set and equilibrated at 37° C. for the higher temperature experiments.

Figure 20:
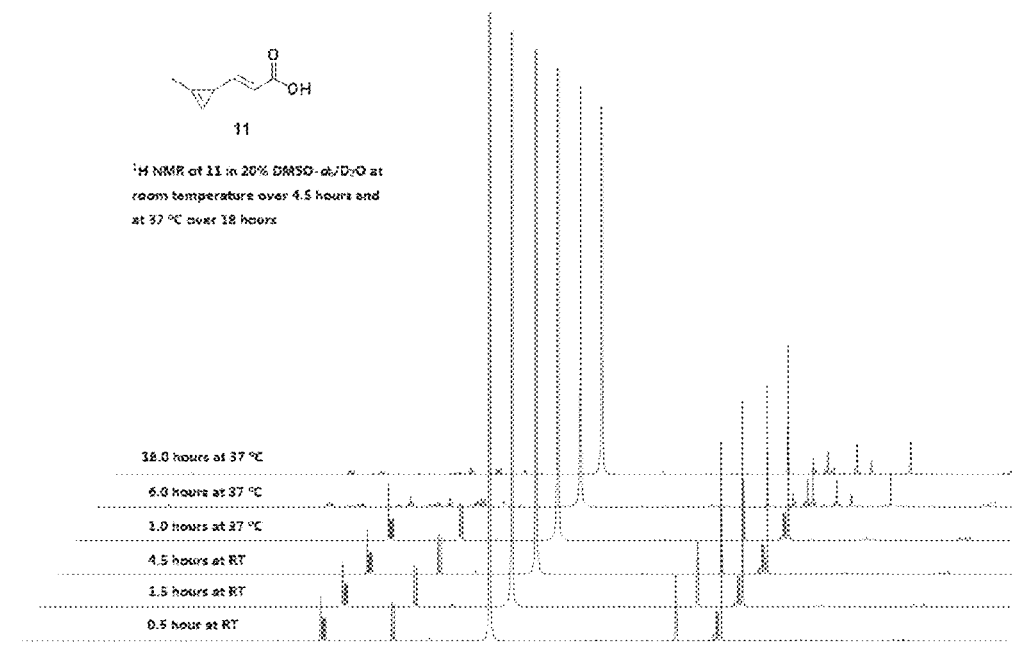
FIG. 20: Stability determination of cyclopropene derivative 11 using 1H NMR.
Figure 21:
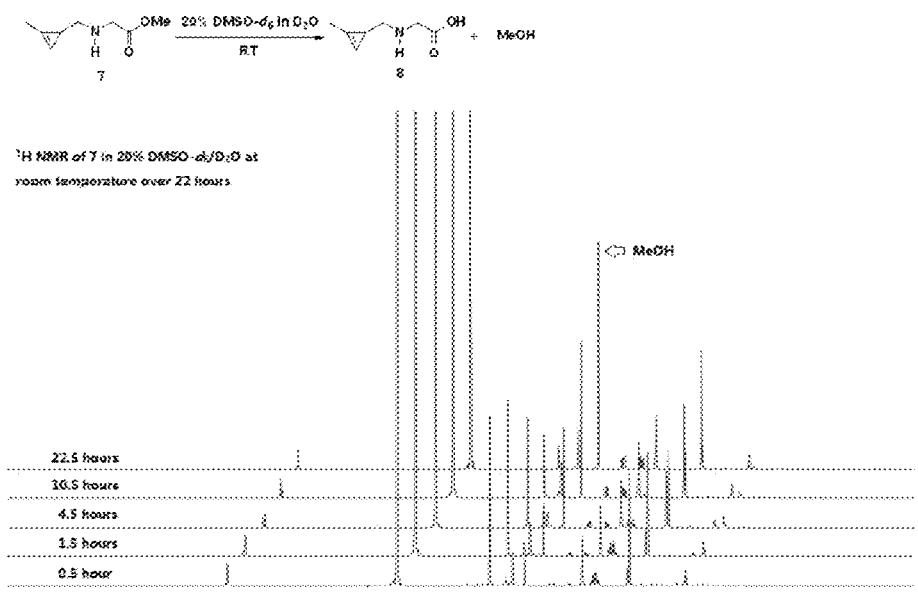
FIG. 21: Stability determination of cyclopropene derivative 7 using 1H NMR.
Figure 22:
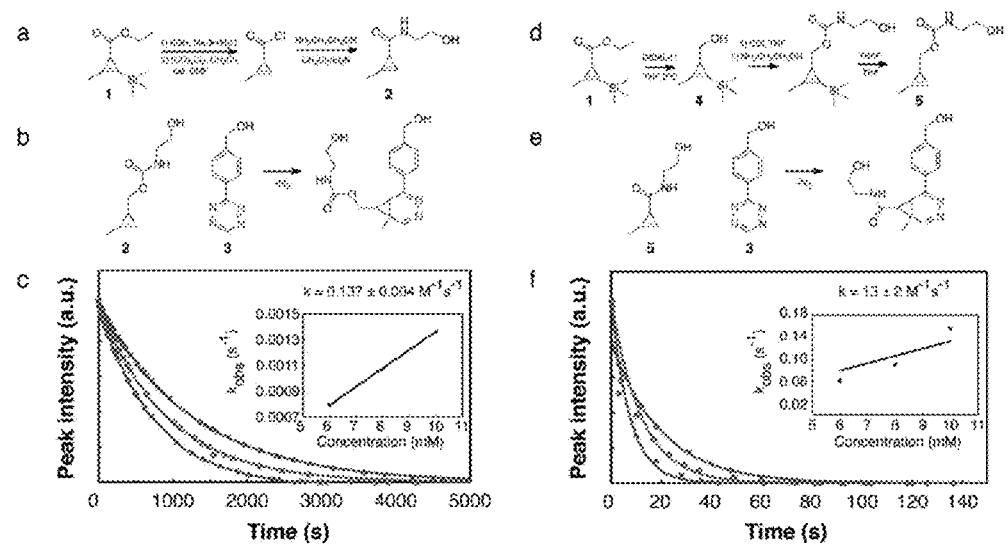
FIG. 22: a) Synthesis of 2-methylcycloprop-2-enecarboxamide 2; b) Reaction of 2 with monoaryl tetrazine 3 leads to formation of diazonorcaradiene isomers (only a single regioisomer depicted); c) Plots of tetrazine absorbance versus time during reaction between 0.6 mM tetrazine 3 and 6, 8, or 10 mM of cyclopropene 2 (data was fit to a first order exponential decay and $k_{obs}$ plotted against concentration (inset) with the slope taken as the second order rate constant); d) Synthesis of 2-methyl-cyclopropene carbamate 5; e) Reaction of 5 with monoaryl tetrazine 3 leads to formation of diazonorcaradiene isomers (only a single regioisomer depicted); f) Plots of tetrazine absorbance versus time during reaction between 0.6 mM tetrazine 3 and 6, 8, or 10 mM of cyclopropene 5 (data was fit to a first order exponential decay and $k_{obs}$ plotted against concentration with the slope taken as the second order rate constant).
Figure 23:
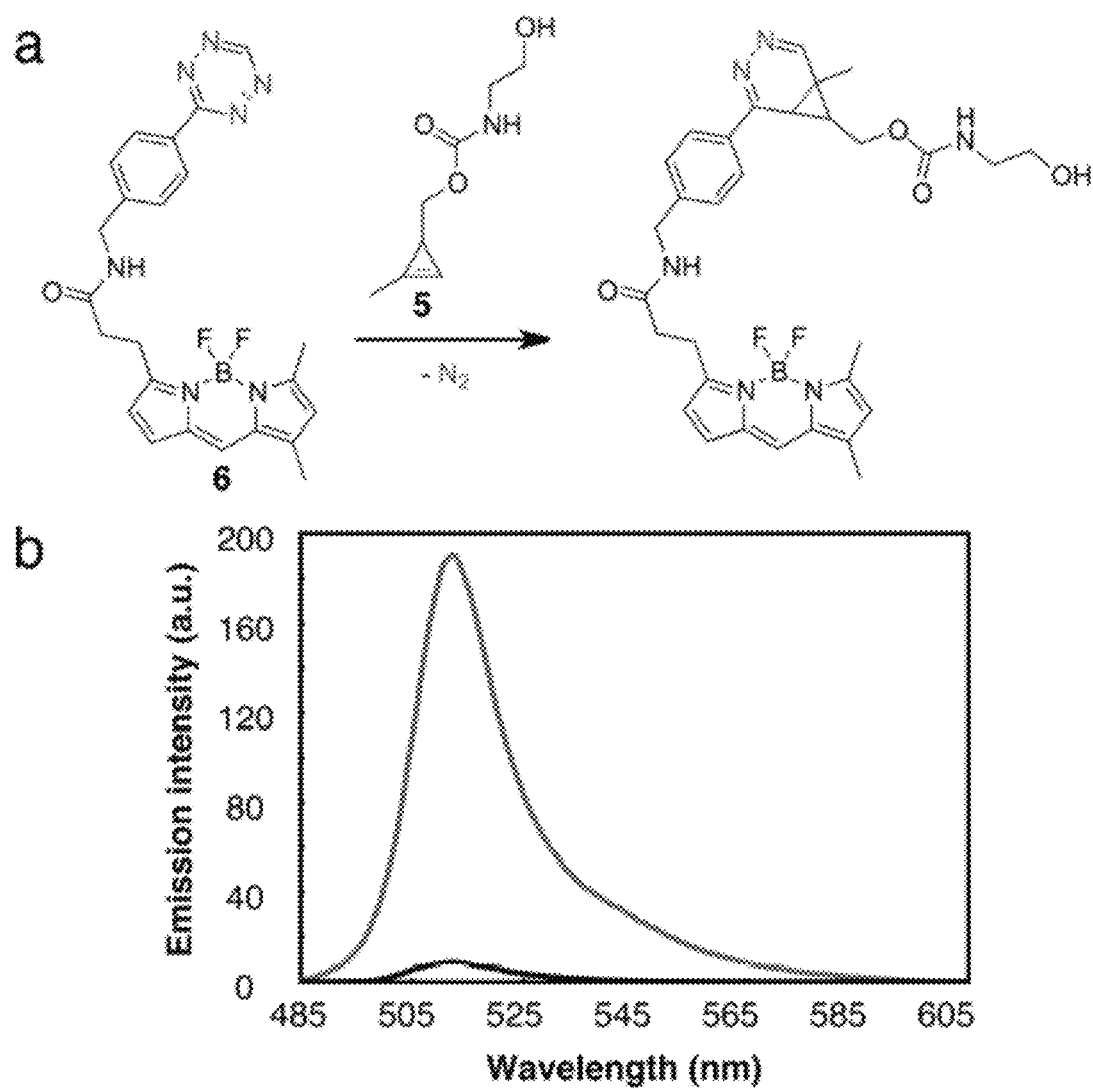
FIG. 23. Reaction of fluorogenic tetrazine-BODIPY FL 6 with methylcyclopropene 5: a) shows the reaction scheme; b) shows the emission spectrum of tetrazine-BODIPY FL before reaction with cyclopropene 5 and after reaction (the intensity at 512 nm increases approximately 22 times). Data was collected in phosphate buffered saline at 20° C.
Figure 24:
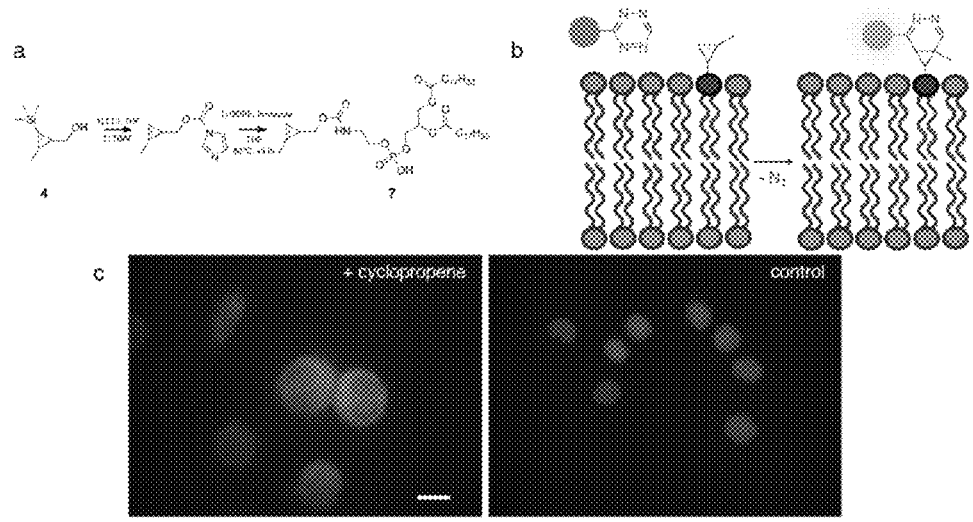
FIG. 24. a) Synthesis of cyclopropene phospholipid 7; b) reaction of fluorogenic tetrazine-BODIPY FL with membrane bound cyclopropene phospholipid 7 showing the BODIPY chromophore is initially quenched by tetrazine with fluorescence recovered after cycloaddition and formation of the coupling adduct; c) shows live-cell imaging of cyclopropene phospholipid 7 distribution in SKBR3 cells with the fluorogenic probe tetrazine-BODIPY FL with the left image depicting cells incubated (t=1 h) with methyl-cyclopropene carbamate followed by 10 µM tetrazine-BODIPY FL probe (t=1 h) and the right image depicting control in which SKBR3 cells were treated with 10 µM tetrazine-BODIPY FL (t=1 h) (cells were treated with 300 nM DAPI in order visualize the nuclei).
Figure 25:
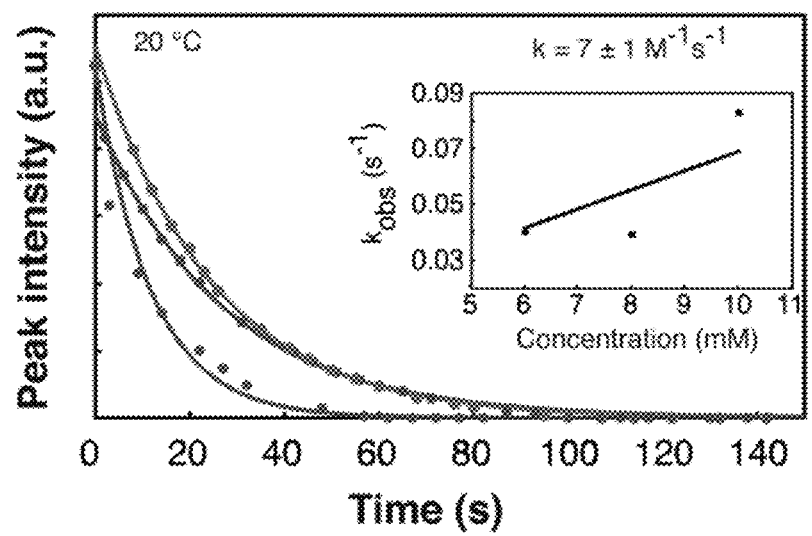
FIG. 25. Kinetics of the tetrazine 3 reaction with cyclopropene 5 at 20° C.: experiment was done with 0.6 mM tetrazine 3 and increasing excess of cyclopropene 5: 6.0 mM, 8.0 mM, 10.0 mM; the insert shows the corresponding observed reaction rates (kobs) from the fitted data (individual fits shown as lines in the main graph) plotted against cyclopropene 5 concentrations and the slope of the resulting line was used to determine the second-order rate constant, indicated in the upper right corner.
Figure 26:
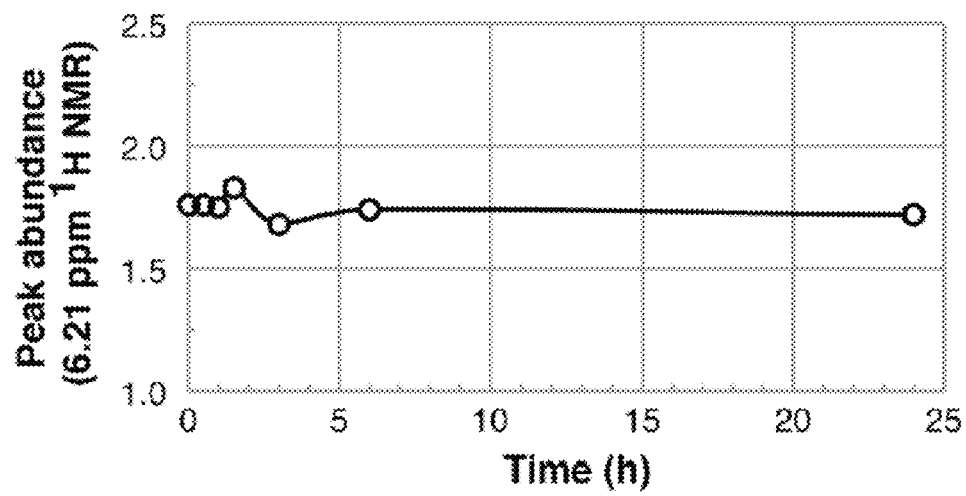
FIG. 26. Time course of stability of cyclopropene carbamate 5 by $^1$H NMR peak abundance at 6.21 ppm over 24 h.
Figure 27:
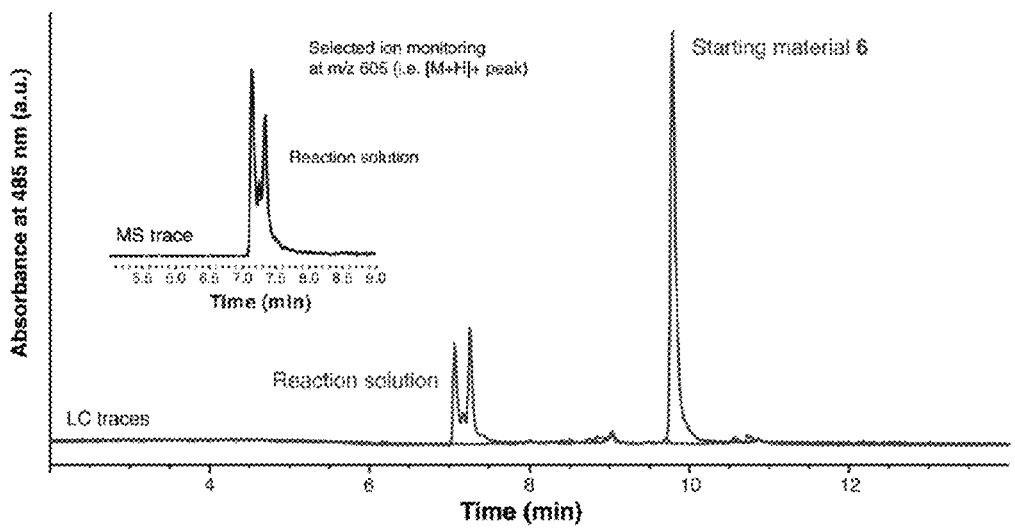
FIG. 27. Reaction between tetrazine-BODIPY FL 6 with cyclopropene 5: HPLC trace of purified tetrazine-BODIPY FL 6 (0.08 mM in 8% DMF/H2O) overlaid with HPLC trace of the reaction products from addition of cyclopropene 5 to tetrazine-BODIPY FL 6: the insert shows the MS trace of the reaction solution, selected ion monitoring at m/z 605 (i.e. [M+H]+ peak).
Figure 28:
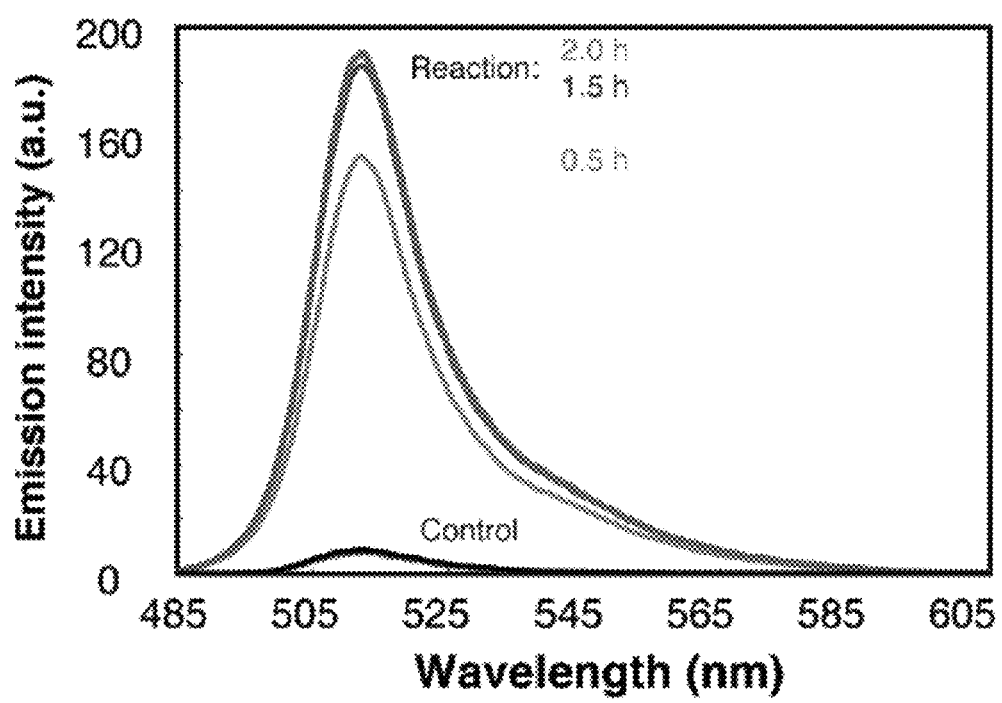
FIG. 28. Emission intensity measurements of the tetrazine-BODIPY FL 6 reaction with cyclopropene 5: emission of the reaction mixture is shown at 30 min, 90 min, and 120 min. and the corresponding control sample lacking cyclopropene 5 was measured initially at 0 min and 120 min.
Figure 29:
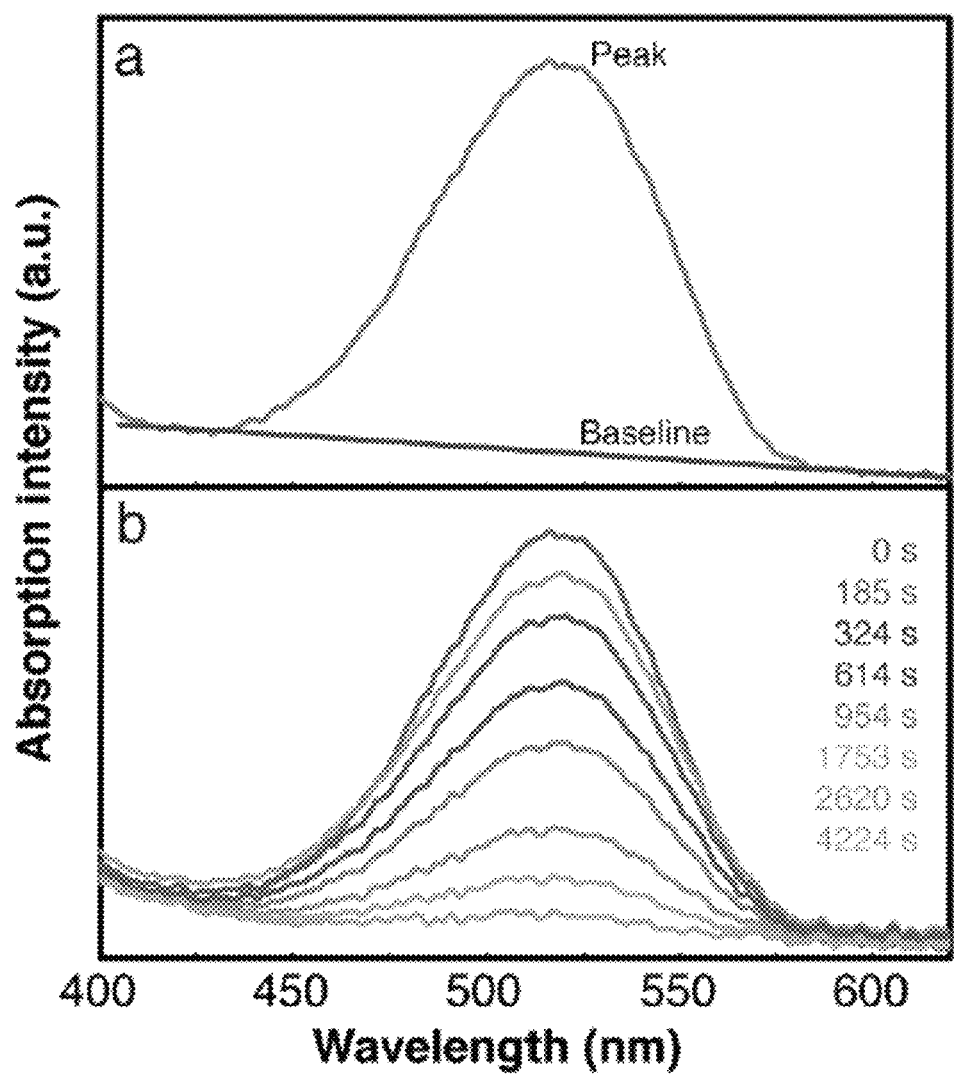
FIG. 29. Tetrazine peak absorption measurements for the reaction rate determination. A representative reaction of 0.6 mM tetrazine 3 with 6.0 mM cyclopropene 2 at 37° C. is shown; (a) shows initial time 0 s tetrazine 3 absorption peak was defined by the difference in the absorption trace and the baseline slope (the baseline was determined from the absorption values preceding and following the peak); (b) shows the measured absorption traces over time for the above reaction, shown at a few reaction timepoints (in seconds: 0; 185; 324, 614, 954, 1753, 2620, 4224).
Figure 30:
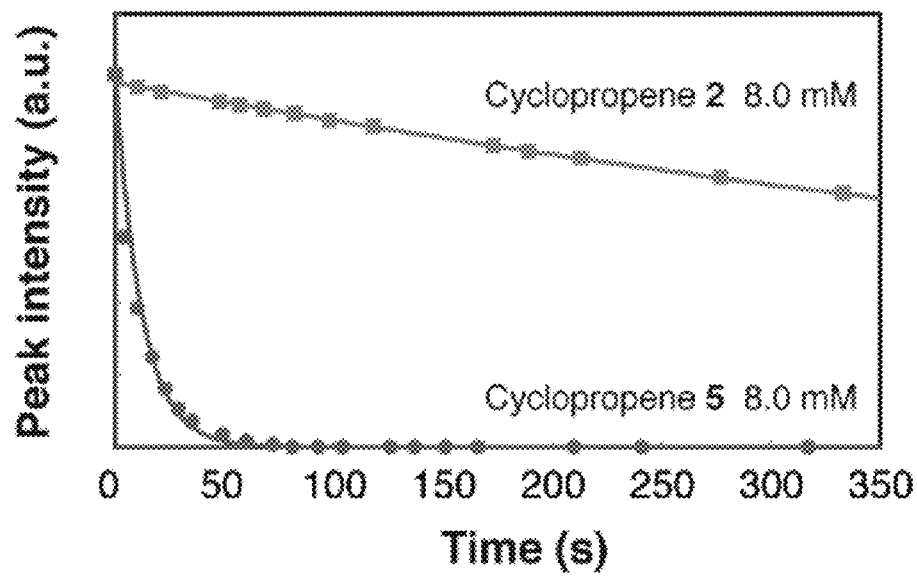
FIG. 30. Tetrazine-cyclopropene reaction kinetics comparison: tetrazine 3 (concentration of 0.6 mM in both cases) absorption peak intensity was measured as a function of time while reacting with cyclopropenes: cyclopropene 5 at 37° C. and cyclopropene 2 at 37° C., at 8.0 mM (the corresponding data fits are shown as lines).
Figure 31:
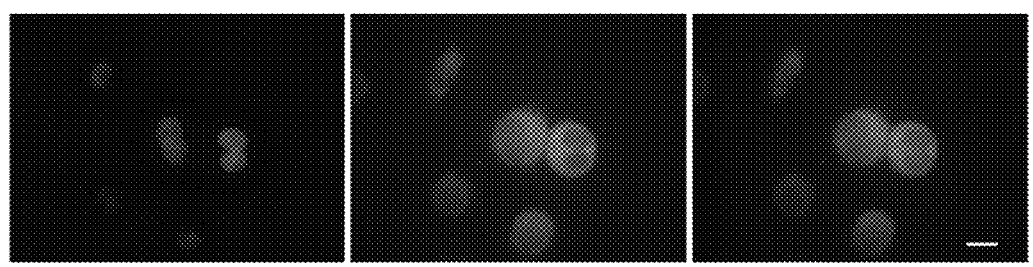
FIG. 31. Staining of SKBR3 cells with cyclopropene 5 and tetrazine-BODIPY FL: DAPI fluorescence (left panel) indicates the stained nuclei and the fluorescence (middle panel) is the result of the cycloaddition of the quenched tetrazine-BODIPY FL probe with the methyl-cyclopropene carbamate; the right panel shows the overlay of the two signals.
Figure 32:
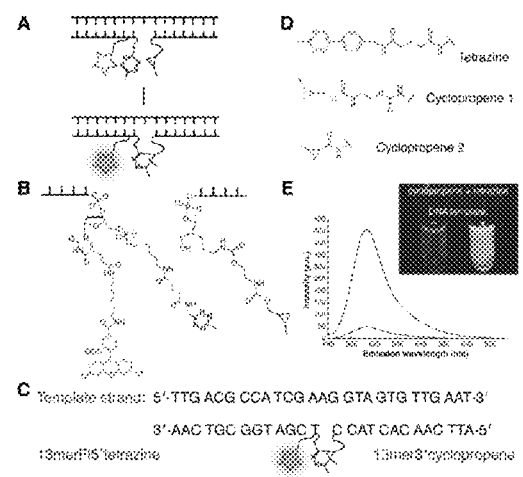
FIG. 32. Antisense oligonucleotide probe design: (A) DNA probe ligation scheme, catalyzed by hybridization against a template; (B) Actual reactant structures; (C) Sequences of the template 27mer and the corresponding 13mer DNA probes and the probe truncations (to 7- and 5mers) and template extensions (in the gap region) are indicated in the main text; (D) Structures of tetrazine and cyclopropene reactants used in this study; (E) Fluorescence emission scans upon 480/5 nm excitation shown before and after the reaction of 27mer DNA template with 13merF15'tet+13mer3'cycp1 in hybridization buffer and the insert shows UV irradiated 1 µM solutions of tetrazine and cyclopropene probes in the absence (−) and presence (+) of oligonucleotide template after 5 min incubation. Sequence legend: TTG ACG CCA TCG AAG GTA GTG TTG AAT (SEQ ID NO:1); ATT CAA CAC TAC C T CGA TGG CGT CAA (SEQ ID NO:2).
Figure 33:
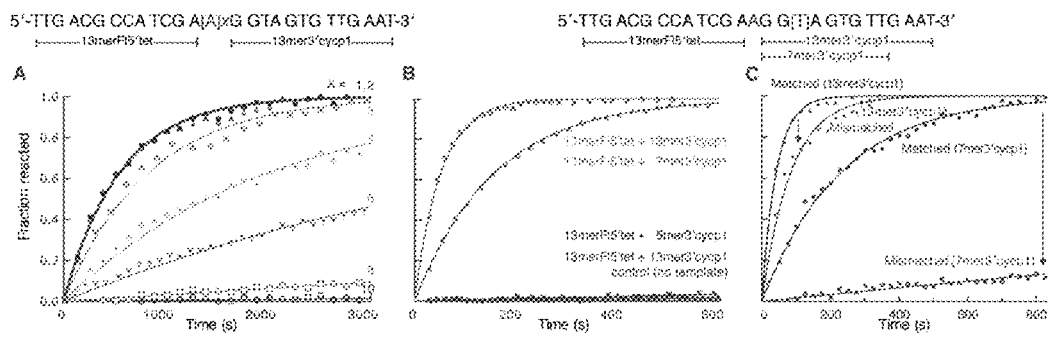
FIG. 33. Effect of the probe and template constructs on the ligation reaction: (A) Probe binding site separation affects the apparent reaction rate with the DNA templates (shown above the data graph) with increasing central polyA spacer were compared by reacting 13merF15'tet+13mer3'cycp1 in the hybridization buffer at 25° C.; (B) DNA probe length optimization via fluorescence emission of 13merF15'tet+ 13mer3'cycp1 reaction with 27mer DNA template (1 µM each in 150 mM MOPS pH 7.5, 25° C.) is shown as measured data points and fitted curves, DNA-templated reaction of 13merF15'tet with shorter 7mer3'cycp1, and with 5mer3'cycp1, and a control reaction of 13merF15'tet and 13mer3'cycp1 with no template; (C) Effect of a nucleotide mismatch on the reaction kinetics depends on the length of the hybridization probe by varying reactant cyclopropene oligomer length wherein Hybridization against the fully-matched 27mer template (labelled "Matched") and against the singly-mismatched 27mer template ("Mismatched" [T] at pos. 17) were done with 13merF15'tet reacting with 13mer3'cycp1 or with 7mer3'cycp1 (Solution conditions were Tris-borate buffer pH 8.4, 5 mM MgCl$_2$ at 37° C.). Sequence legend: TTG ACG CCA TCG A[A]xG GTA GTG TTG AAT (SEQ ID NO:3); TTG ACG CCA TCG AAG GTA GTG TTG AAT (SEQ ID NO:1).
Figure 34:
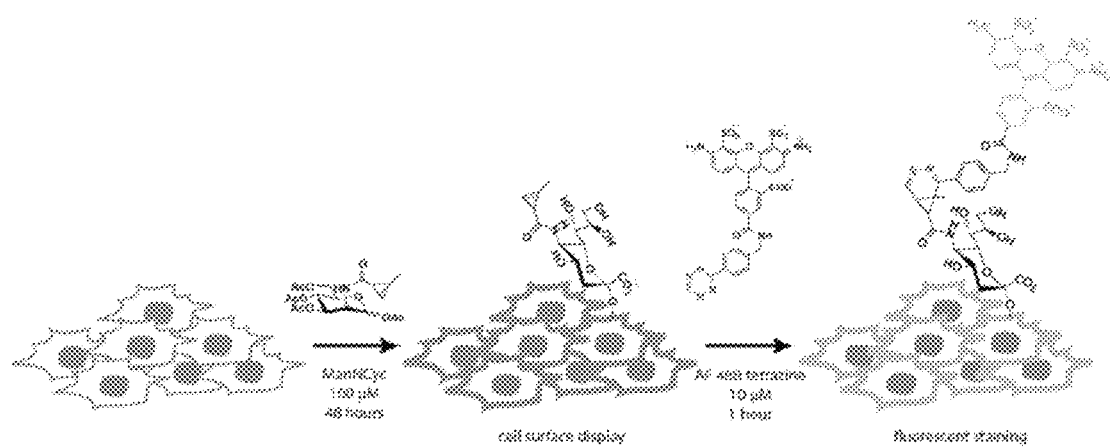
FIG. 34 depicts cartoon outlining proposed fluorescent staining of glycans using tetrazine-cyclopropene chemistry. Ac$_4$ManNCyc 3 is incubated with live cells for 48 hours. If the unnatural mannosamine derivative is processed by the cell, methyl-cyclopropenes will be displayed on the surface and tagged by fluorogenic tetrazine-Alexa Fluor 488.

Absorption spectra were measured manually over time. Absorption peak signal was taken as the average of measurements at 519-521 nm. Baseline signal was determined as the sloping line connecting the measured background levels preceding and following the tetrazine peak (410-430 nm and 590-610 nm, respectively). Final peak intensity value was taken as the signal above the baseline. Reaction rates were obtained by fitting the exponential decays of tetrazine peak absorption intensity as a pseudo first order reaction. Non-linear data fits were performed with GraphPad Prism. Tetrazine reactions with cyclopropene carbamate 5 were carried out at 20 and 37° C. (data points and corresponding fitted curves at 20° C. in FIG. 51, 37° C. in FIG. 2c). Tetrazine reactions with cyclopropene carboxamide 2 were done at 37° C. (FIG. 20. A representative comparison fit is shown for cyclopropenes 5 and 2 at 8.0 mM concentration reacting at 37° C. with 0.6 mM tetrazine.

Live-Cell Microscopy

Human breast cancer SKBR3 cells were received from Professor Jered Haun (University of California, Irvine). The cells were incubated overnight on a Lab-Tek chamber slide maintained in cDMEM medium (10% fetal bovine serum, 1% L-glutamine, 1% penicillin/streptomycin). Cells were washed with phosphate-buffered saline (PBS) and incubated in cDMEM with 100 μM of cyclopropene 5 for 1 hour at 37° C. The media was aspirated, and cells were washed twice with PBS.

Cells were then incubated in cDMEM and 10 μM tetrazine-BODIPY FL 6 probe for 1-2 hours at 37° C. In the last 30 min of incubation 300 nM. DAN was added to the incubation media. Cells were washed twice with PBS before imaging. All photos were collected with an Olympus BX51 epifluorescent microscope equipped with a CCD camera (Olympus, Inc) using the Magna-Fire 2.0 software package. Image acquisition was set at 31 ms exposure for DAPI (DAPI excitation filter 330-385 nm) and 519 ins for BODIPY-FL (FITC excitation filter 450-480 nm) using a phase contrast 100×/1.3 NA oil-immersion lens. At an exposure of 519 ms the control cells display an observable background fluorescence in the FITC channel.

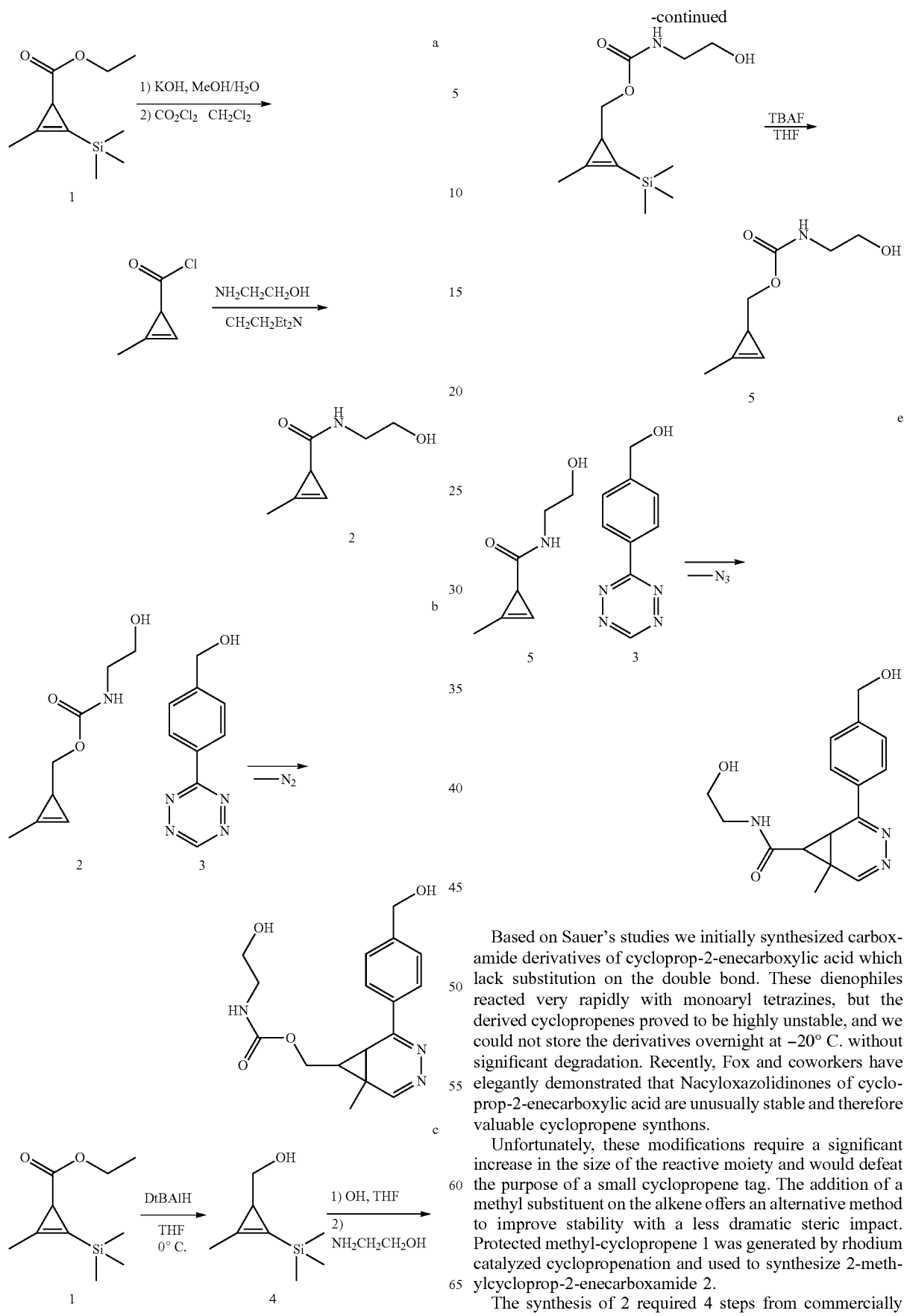

Based on Sauer's studies we initially synthesized carboxamide derivatives of cycloprop-2-enecarboxylic acid which lack substitution on the double bond. These dienophiles reacted very rapidly with monoaryl tetrazines, but the derived cyclopropenes proved to be highly unstable, and we could not store the derivatives overnight at −20° C. without significant degradation. Recently, Fox and coworkers have elegantly demonstrated that Nacyloxazolidinones of cycloprop-2-enecarboxylic acid are unusually stable and therefore valuable cyclopropene synthons.

Unfortunately, these modifications require a significant increase in the size of the reactive moiety and would defeat the purpose of a small cyclopropene tag. The addition of a methyl substituent on the alkene offers an alternative method to improve stability with a less dramatic steric impact. Protected methyl-cyclopropene 1 was generated by rhodium catalyzed cyclopropenation and used to synthesize 2-methylcycloprop-2-enecarboxamide 2.

The synthesis of 2 required 4 steps from commercially available starting materials and was completed in approximately 21% overall yield. As we expected, the addition of a methyl group dramatically improved cyclopropene stability, and 2 could be stored for extended periods of time without degradation. However, these derivatives reacted sluggishly with benzylalcohol tetrazine 3. By observing the disappearance of the characteristic tetrazine absorption band at 520 nm, we measured a second order rate constant of 0.137±0.004 $M_{-1}s_{-1}$ at 37° C. in a solution of water/DMSO (12% DMSO by volume). Although this rate constant compares favorably with previously proven bioorthogonal labeling strategies, [9] it is much slower than the reaction of alternative strained alkenes with tetrazine, such as transcyclooctene and even norbornene.

Faster kinetics would improve coupling yields, particularly for applications where one is unable to flood the target with a large excess of reactant, for example in live-cell intracellular labeling or in vivo. In an attempt to improve the kinetics of cycloaddition, we reduced the ester of precursor 1 to form (2-methyl-3-(trimethylsilyl)cycloprop-2-en-1-yl) methanol 4. 4 is a highly convenient synthon that can be made in gram scale in 2 steps from commercially available starting materials. 4 can be further conjugated to primary amines by carbamate formation followed by deprotection of the trimethylsilyl protecting group to afford 2-methyl-cyclopropene carbamate 5. The synthesis of 5 required 5 steps from commercially available starting materials and was completed in approximately 33% overall yield. We speculated that 5 would possess the stability afforded by the methyl derivatized alkene but display increased inverse Diels-Alder reactivity compared to 2 by elimination of the electron-withdrawing carbonyl. Indeed, Carbamate 5 was highly reactive to tetrazine 3, and cycloaddition proceeded with a second order rate constant of 13±2 $M_{-1}s_{-1}$ at 37° C. in a solution of water/DMSO (12% DMSO by volume). This is an improvement of approximately two orders of magnitude compared to cyclopropene carboxamide 2. At 20° C., we measured a rate constant of 7±1 $M_{-1}s_{-1}$ (12% DMSO by volume). Cyclopropene 5 could be stored at −20° C. for extended periods without degradation and displayed excellent stability in aqueous solutions at 37° C. with no significant degradation observed over 24 hours.

Fluorogenic probes are highly valuable in live-cell imaging applications due to inherent lowering of background fluorescence due to non-specific binding or accumulation. This is particularly relevant for imaging of intracellular molecules as washout can prove problematic. Recent work has demonstrated that tetrazines are capable of significantly quenching several bright fluorescent probes, potentially through a resonant energy transfer mechanism. These probes show significant fluorescent "turn-on" after reaction with dienophiles, are easy to synthesize from commercially available reactive precursors, and use bright, conveniently excited fluorophores which are commonly used in cellular imaging, such as boron dipyrromethane (BODIPY) and Oregon-Green. The combination of recently discovered high quality fluorogenic tetrazine probes, such as tetrazine-BODIPY FL, with small dienophile tags would advance bioorthogonal live-cell imaging. Tetrazine-BODIPY FL probe 6 reacts rapidly with cyclopropene carbamate 5 with concomitant increase in fluorescence. In phosphate buffered saline there is a 22-fold increase in fluorescence intensity after excess cyclopropene addition, similar to previous observations of fluorescence increase after reaction with alternative strained dienophiles. The reaction can also be monitored by liquid-chromatography/mass spectrometry.

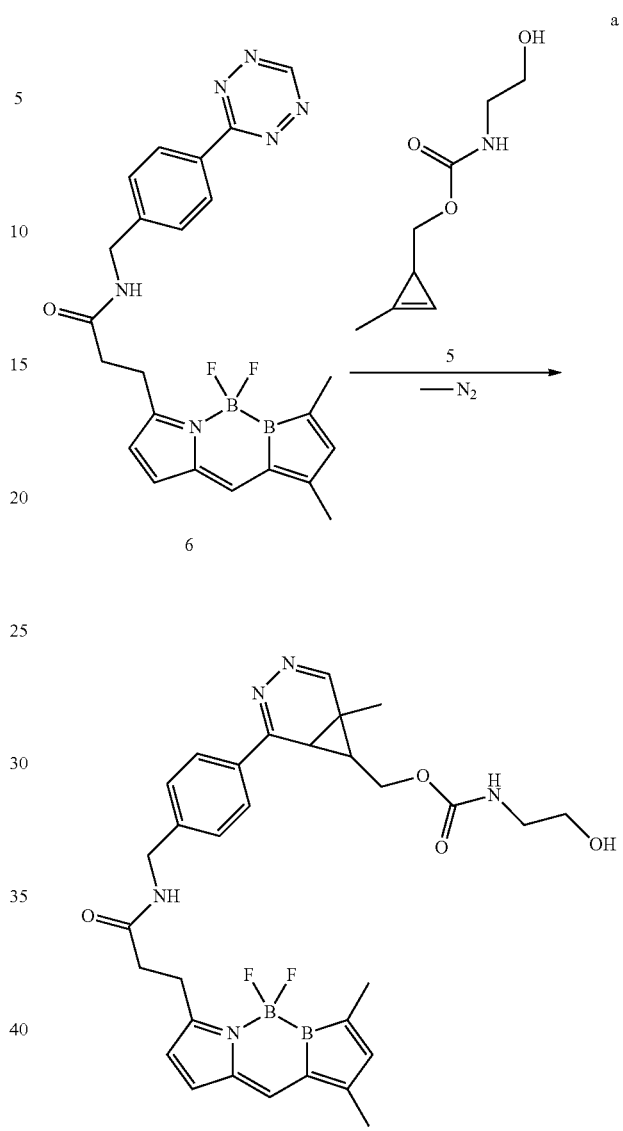

Addition of an equivalent of cyclopropene 5 results in complete reaction of the tetrazine-BODIPY FL and the expected formation of multiple overlapping peaks all with molecular masses indicative of the product diazonorcaradiene isomers. Live-cell labeling of bioorthogonal functional groups has emerged as a powerful tool for analyzing small molecule distributions in cells. In order to demonstrate the applicability of cyclopropene tags for live-cell imaging via fluorogenic tetrazine cycloadditions, we synthesized a cyclopropene tagged phospholipid 7. Bioorthogonal reactions are increasingly used for lipid imaging and labeling, and there have been several exciting applications include metabolic labeling of choline phospholipids, high-throughput analysis of protein lipidation, and monitoring the trafficking of soluble lipids.[22] Cyclopropene-tetrazine cycloadditions would offer the important advantage of intracellular imaging in live cells using lipophilic fluorogenic tetrazines. Additionally, in vitro applications would benefit from improved reaction kinetics and the lack of redox-active copper catalysts which can potentially damage biomolecules while adding an extra layer of complexity.

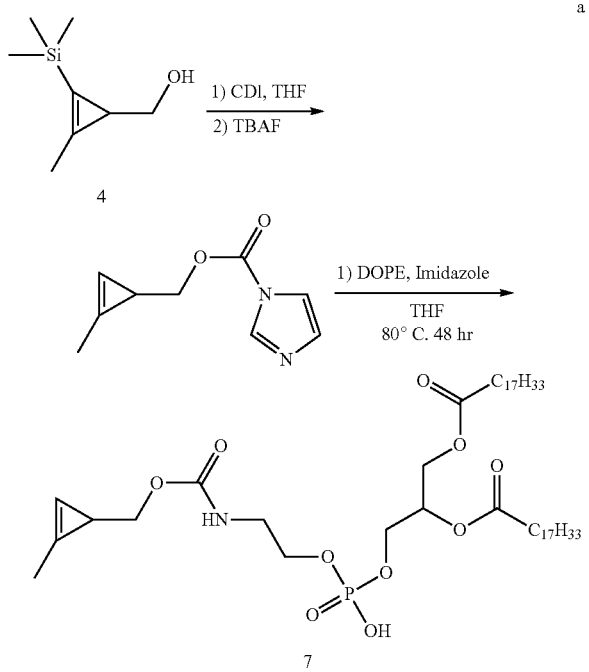

In order to image the distribution of cyclopropene phospholipid 7 in human cells, we incubated SKBR3 breast cancer cells in media (cDMEM) containing 100 μM 7 for one hour. After washing with media, the cells were subsequently incubated with 10 μM of tetrazine-BODIPY FL for one hour. Cells were then washed and imaged using fluorescence microscopy. Staining of membrane structures could be readily observed with a noticeable absence of staining within the nucleus. In contrast, control cells that were not exposed to the cyclopropene lipid but were treated with the tetrazine-BODIPY FL probe showed relatively negligible background staining, demonstrating the benefit of using a fluorogenic cycloaddition which significantly mitigates signal due to non-specific binding. We are currently utilizing cyclopropene 7 to visualize phospholipid uptake in several model systems. Additionally, we are synthesizing additional cyclopropene lipid tags in order to image and detect specific lipid distribution and lipid posttranslational modifications in live cells.

Modulating the substituents of cyclopropenes can have a dramatic effect on stability and the kinetics of tetrazine cycloaddition. Through synthetic modification of the cyclopropene scaffold we have developed a methyl-cyclopropene handle that is stable in aqueous solution but retains high reactivity with tetrazines. Cyclopropene handles are capable of eliciting a strong fluorogenic response from quenched tetrazine fluorescent probes and this feature can be utilized to perform live-cell imaging which we demonstrate by labeling cyclopropene-modified phospholipids. The use of methyl-cyclopropenes will extend the advantages of tetrazine cycloadditions to small molecule tracking applications that require minimal reaction partners. We are currently pursuing applications incorporating cyclopropenes in metabolic and enzyme activity reporters such as lipid, monosaccharide, and amino acid analogs.

X. References a) J. M. Baskin, J. A. Prescher, S. T. Laughlin, N. J. Agard, P. V. Chang, I. A. Miller, A. Lo, J. A. Codelli, C. R. Bertozzi, *Proceedings of the National Academy of Sciences of the United States of America* 2007, 104, 16793-16797; b) K. Lang, L. Davis, J. Torres-Kolbus, C. Chou, A. Deiters, J. Chin, *Nat Chem* 2012, 4, 298-304; c) J. Ngo, D. Tirrell, *Acc Chem Res* 2011, 44, 677-685; d) K. Rangan, Y. Yang, G. Charron, H. Hang, *J Am Chem Soc* 2010, 132, 10628-10629; e) A. Salic, T. Mitchison, *Proceedings of the National Academy of Sciences of the United States of America* 2008, 105, 2415-2420.

N. Devaraj, R. Weissleder, *Acc Chem Res* 2011, 44, 816-827.

a) N. Devaraj, R. Upadhyay, J. Haun, S. Hilderbrand, R. Weissleder, *Angew Chem Int Ed Engl* 2009, 48, 7013-7016; b) N. Devaraj, S. Hilderbrand, R. Upadhyay, R. Mazitschek, R. Weissleder, *Angew Chem Int Ed Engl* 2010, 49, 2869-2872.

a) T. Plass, S. Milles, C. Koehler, J. Szymanski, R. Mueller, M. Wiessler, C. Schultz, E. Lemke, *Angew Chem Int Ed Engl* 2012, 51, 4166-4170; b) G. Budin, K. Yang, T. Reiner, R. Weissleder, *Angew Chem Int Ed Engl* 2011, 50, 9378-9381.

J. Yang, J. Seckute, C. Cole, N. Devaraj, *Angew Chem Int Ed Engl* 2012, 51, 7476-7479.

a) M. Blackman, M. Royzen, J. Fox, *J Am Chem Soc* 2008, 130, 13518-13519; b) N. Devaraj, R. Weissleder, S. Hilderbrand, *Bioconjug Chem* 2008, 19, 2297-2299; c) M. Wiessler, W. Waldeck, C. Kliem, R. Pipkorn, K. Braun, *Int J Med Sci* 2009, 7, 19-28; d) N. Devaraj, G. Thurber, E. Keliher, B. Marinelli, R. Weissleder, *Proceedings of the National Academy of Sciences of the United States of America* 2012, 109, 4762-4767; e) R. Rossin, P. Verkerk, S. van den Bosch, R. Vulders, I. Verel, J. Lub, M. Robillard, *Angew Chem Int Ed Engl* 2010, 49, 3375-3378; f) M. Karver, R. Weissleder, S. Hilderbrand, *Angew Chem Int Ed Engl* 2012, 51, 920-922.

a) Z. Yu, Y. Pan, Z. Wang, J. Wang, Q. Lin, *Angew Chem Int Ed Engl* 2012, ASAP; b) D. Patterson, L. Nazarova, B. Xie, D. Kamber, J. Prescher, *J Am Chem Soc* 2012, 134, 18638-18643.

a) S. Luchansky, S. Goon, C. Bertozzi, *Chembiochem* 2004, 5, 371-374; b) C. Oetke, R. Brossmer, L. Mantey, S. Hinderlich, R. Isecke, W. Reutter, O. Keppler, M. Pawlita, *J Biol Chem* 2002, 277, 6688-6695.

S. Han, B. Collins, P. Bengtson, J. Paulson, *Nat Chem Riot* 2005, 1, 93-97.

a) E. Saxon, C. Bertozzi, *Science* 2000, 287, 2007-2010; b) E. Sletten, C. Bertozzi, *Acc Chem Res* 2011, 44, 666-676.

a) H. Kayser, R. Zeitler, C. Kannicht, D. Grunow, R. Nuck, W. Reutter, *J Biol Chem* 1992, 267, 16934-16938; b) O. Keppler, R. Horstkorte, M. Pawlita, C. Schmidt, W. Reutter, *Glycobiology* 2001, 11, 11R-18R.

C. Jacobs, S. Goon, K. Yarema, S. Hinderlich, H. Hang, D. Chai, C. Bertozzi, *Biochemistry* 2001, 40, 12864-12874.

C. Jacobs, K. Yarema, L. Mahal, D. Nauman, N. Charters, C. Bertozzi, *Methods Enzymol* 2000, 327, 260-275.

E. Saxon, S. Luchansky, H. Hang, C. Yu, S. Lee, C. Bertozzi, *J Am Chem Soc* 2002, 124, 14893-14902.

H. Hang, C. Yu, D. Kato, C. Bertozzi, *Proceedings of the National Academy of Sciences of the United States of America* 2003, 100, 14846-14851.

Y. Liang, J. Mackey, S. Lopez, F. Liu, K. Houk, *J Am Chem Soc* 2012, Accepted

Devaraj, N. K.; Weissleder, R. *Acc Chem Res* 2011, 44, 816.

Lang, K.; Davis, L.; Torres-Kolbus, J.; Chou, C.; Deiters, A.; Chin, J. W. *Nat Chem* 2012, 4, 298.

Hansell, C. F.; Espeel, P.; Stamenovic, M. M.; Barker, I. A.; Dove, A. P.; Du Prez, F. E.; O'Reilly, R. K. *J Am Chem Soc* 2011, 133, 13828.

Zhou, H.; Johnson, J. A. *Angew Chem Int Ed Engl* 2013, 52, 2235.

Devaraj, N. K.; Thurber, G. M.; Keliher, E. J.; Marinelli, B.; Weissleder, R. *Proc Natl Acad Sci USA* 2012, 109, 4762.

Blackman, M. L.; Royzen, M.; Fox, J. M. *J Am Chem Soc* 2008, 130, 13518.

Devaraj, N. K.; Weissleder, R.; Hilderbrand, S. A. *Bioconjug Chem* 2008, 19, 2297.

Rostovtsev, V. V.; Green, L. G.; Fokin, V. V.; Sharpless, K. B. *Angew Chem Int Ed Engl* 2002, 41, 2596.

Kolb, H. C.; Finn, M. G.; Sharpless, K. B. *Angew Chem Int Ed Engl* 2001, 40, 2004.

Yang, J.; Karver, M. R.; Li, W.; Sahu, S.; Devaraj, N. K. *Angew Chem Int Ed Engl* 2012, 51, 5222.

Sletten, E. M.; Bertozzi, C. R. *Angew Chem Int Ed Engl* 2009, 48, 6974.

Saxon, E.; Luchansky, S. J.; Hang, H. C.; Yu, C.; Lee, S. C.; Bertozzi, C. R. *J Am Chem Soc* 2002, 124, 14893.

Taylor, M. T.; Blackman, M. L.; Dmitrenko, O.; Fox, J. M. *J Am Chem Soc* 2011, 133, 9646.

Yang, J.; Seckute, J.; Cole, C. M.; Devaraj, N. K. *Angew Chem Int Ed Engl* 2012, 51, 7476.

Sauer, J.; Heinrichs, G. *Tetrahedron Letters* 1966, 7, 4979.

Dowd, P.; Gold, A. *Tetrahedron Letters* 1969, 10, 85.

Yan, N.; Liu, X.; Pallerla, M. K.; Fox, J. M. *The Journal of organic chemistry* 2008, 73, 4283.

Yu, Z.; Pan, Y.; Wang, Z.; Wang, J.; Lin, Q. *Angew Chem Int Ed Engl* 2012, 51, 10600.

Patterson, D. M.; Nazarova, L. A.; Xie, B.; Kamber, D. N.; Prescher, J. A. *J Am Chem Soc* 2012, 134, 18638.

Liang, Y.; Mackey, J. L.; Lopez, S. A.; Liu, F.; Houk, K. N. *J Am Chem Soc* 2012, 134, 17904.

Cole, C. M.; Yang, J.; Seckute, J.; Devaraj, N. K. *ChemBioChem* 2013, 14, 205.

Sauer, J.; Heldmann, D. K.; Hetzenegger, J.; Krauthan, J.; Sichert, H.; Schuster, J. *Eur J Org Chem* 1998, 2885.

Thalhammer, F.; Wallfahrer, U.; Sauer, J. *Tetrahedron Letters* 1990, 31, 6851

J. Yang, J. Šečlutė, C. M. Cole, N. K. Devaraj, *Angew. Chem. Int. Ed.* 2012, 51, 7476-7479.

Liu, J., Cao, Z. & Lu, Y. Functional Nucleic Acid Sensors. *Chetn Rev* 109, 1948-1998 (2009).

Armitage, B. A. Imaging of RNA in live cells. *Curr Opin Chem Biol* 15, 806-812 (2011).

Silverman, A. P. & Kool, E. T. Detecting RNA and DNA with Templated Chemical Reactions. *Chem Inform* 37, (2006).

Marti, A. A., Jockusch, S., Stevens, N., Ju, J. & Turro, N. J. Fluorescent Hybridization Probes for Sensitive and Selective DNA and RNA Detection. *Ace. Chem. Res.* 40, 402-409 (2007).

Guo, J., Ju, J. & Turro, N. J. Fluorescent hybridization probes for nucleic acid detection. *Analytical and bioanalytical chemistry* 402, 3115-3125 (20 12).

Stojanovic, M. N., de Prada, P. & Landry, D. W. Catalytic molecular beacons. *Chem Bio Chem* 2, 411-415 (2001).

Dave, N. & Liu, J. Fast Molecular Beacon Hybridization in Organic Solvents with Improved Target Specificity. *J Plzys Chern B* 114, 15694-15699 (2010).

Chen, A. K., Davydenko, O., Behlke, M. A. & Tsourkas, A. Ratiometric bimolecular beacons for the sensitive detection of RNA in single living cells. *Nucleic Acids Res* 38, e148 (2010).

Wang, K. et al. Molecular Engineering of DNA: Molecular Beacons. *Angew. Chem. Int. Ed.* 48, 856-870 (2009).

[40] Tsourkas, A., Behlke, M. A., Rose, S. D. & Bao, G. Hybridization kinetics and thermodynamics of molecular beacons. *Nucleic Acids Res* 31, 1319-1330 (2003).

Tyagi, S. Imaging intracellular RNA distribution and dynamics in living cells. *Nature Methods* 6, 331-338 (2009).

Mhlanga, M. M., Vargas, D. Y., Fung, C. W., Kramer, F. R. & Tyagi, S. tRNA-linked molecular beacons for imaging mRNAs in the cytoplasm of living cells. *Nucleic Acids Res* 33, 1902-1912 (2005).

Gryaznov, S. M., Schultz, R., Chaturvedi, S. K. & Letsinger, R. L Enhancement of selectivity in recognition of nucleic acids via chemical autoligation. *Nucleic Acids Res* 22, 2366-2369 (1994).

Kumar, R. et al. Template-directed oligonucleotide strand ligation, covalent intramolecular DNA circularization and catenation using click chemistry. *J Am Chem Soc* 129, 6859-6864 (2007).

Rohatgi, R., Bartel, D. P. & Szostak, J. W. Nonenzymatic, Template-Directed Ligation of Oligoribonucleotides Is Highly Regioselective for the Formation of 3'-5' Phosphodiester Bonds. *J Am Clzem Soc* 118, 3340-3344 (1996).

Sarkar, T., Conwell, C. C., Harvey, L C., Santai, C. T. & Hud, N. V. Condensation of oligonucleotides assembled into nicked and gapped duplexes: potential structures for oligonucleotide delivery. *Nucleic Acids Res* 33, 143-151 (2005).

Bruick, R. K., Dawson, P. E., Kent, S. B., Usman, N. & Joyce, G. F. Template-directed ligation of peptides to oligonucleotides. *Chern. Bioi.* 3, 49-56 (1996).

Peng, X., Li, H. & Seidman, M. A Template-Mediated Click-Click Reaction: PNA-DNA, PNAPNA (or Peptide) Ligation, and Single Nucleotide Discrimination. *Eur. J. Org. Chem.* 2010, 4194-4197 (2010).

Peelen, D. & Smith, L M. Immobilization of Amine-Modified Oligonucleotides on AldehydeTerminated Alkanethiol Monolayers on Gold. *J Am Chem Soc* 21, 266-271 (2005).

Xu, Y., Karalkar, N. B. & Kool, E. T. Nonenzymatic autoligation in direct three-color detection of RNA and DNA point mutations. *Nature Biotechnology* 19, 148-152 (2001).

Silverman, A. P. & Kool, E. T. Quenched probes for highly specific detection of cellular RNAs. *Trends Bioteclzno/*23, 225-230 (2005).

Shibata, A., Abe, H. & Ito, Y. Oligonucleotide-templated reactions for sensing nucleic acids. *Molecules* 17, 2446-2463 (2012).

El-Sagheer, A. H. & Brown, T. Click chemistry with DNA. *Chern. Soc. Rev.* 39, 1388-1405 (2010).

Sando, S., Abe, H. & Kool, E. T. Quenched Auto-Ligating DNAs: Multicolor Identification of Nucleic Acids at Single Nucleotide Resolution. *J Am Chem Soc* 126, 1081-1087 (2004).

Devaraj, N. K., Hilderbrand, S., Upadhyay, R., Mazitschek, R. & Weissleder, R. Bioorthogonal Turn-On Probes for Imaging Small Molecules inside Living Cells. *Angew. Chem. Int. Ed.* 49, 2869-2872 (2010).

Devaraj, N. K. & Weissleder, R. Biomedical Applications of Tetrazine Cycloadditions. *Ace. Chem. Res.* 44, 816-827 (2011).

Liu, D. S. et al. Diels-Alder Cycloaddition for Fluorophore Targeting to Specific Proteins inside Living Cells. *J Am Chem Soc* 134, 792-795 (2012).

Plass, T. et al. Amino Acids for Diels-Alder Reactions in Living Cells. *Angew. Chem. Int. Ed.* 51, 4166-4170 (2012).

Dumas-Verdes, C. et al. BODIPY—Tetrazine Multichromophoric Derivatives. *Angew. Chem. Int. Ed. Engl.* 2010, 2525-2535 (2010).

Budin, G., Yang, K. S., Reiner, T. & Weissleder, R. Bioorthogonal Probes for Polo-like Kinase I Imaging and Quantification. *Angew. Chem. Int. Ed.* 50, 9378-9381 (2011).

Lang, K. et al. Genetically encoded norbornene directs site-specific cellular protein labelling via a rapid bioorthogonal reaction. *Nat Chem* 4, 298-304 (2012).

Yang, J., Seckute, J., Cole, C. M. & Devaraj, N. K. Live-cell imaging of cyclopropene tags with fluorogenic tetrazine cycloadditions. *Angew. Chem. Int. Ed.* 51, 7476-7479 (2012).

Sletten, E. M. & Bertozzi, C. R. From Mechanism to Mouse: A Tale of Two Bioorthogonal Reactions. *Ace. Chem. Res.* 44, 666-676 (2011).

Blackman, M. L., Royzen, M. & Fox, J. M. Tetrazine ligation: fast bioconjugation based on inverse-electron-demand Diels-Alder reactivity. *J Am Chem Soc* 130, 13518-13519 (2008).

Devaraj, N. K., Weissleder, R. & Hilderbrand, S. A. Tetrazine-based cycloadditions: application to pretargeted live cell imaging. *Bioconjugate Chem.* 19, 2297-2299 (2008).

Yang, J., Karver, M. R., Li, W., Sahu, S. & Devaraj, N. K. Metal-Catalyzed One-Pot Synthesis of Tetrazines Directly from Aliphatic Nitriles and Hydrazine. *Angew. Chem. Int. Ed. Engl.* 124, 5312-5315 (2012).

Karver, M. R., Weissleder, R. & Hilderbrand, S. A. Synthesis and Evaluation of a Series of 1,2,4,5-Tetrazines for Bioorthogonal Conjugation. *Bioconjugate Chem.* 22, 2263-2270 (2011).

Li, X. & Liu, D. R. DNA-Templated Organic Synthesis: Nature's Strategy for Controlling Chemical Reactivity Applied to Synthetic Molecules. *Angew. Chem. Int. Ed.* 43, 4848-4870 (2004).

Herschlag, D. Implications of ribozyme kinetics for targeting the cleavage of specific RNA molecules in vivo: more isn't always better. *Proc Nat! Acad Sci USA* 88, 6921-6925 (1991).

40. Elghanian, R., Storhoff, J. J., Mucic, R. C., Letsinger, R. L. & Mirkin, C. A. Selective colorimetric detection of polynucleotides based on the distance-dependent optical properties of gold nanoparticles. *Science* 277, 1078-1081 (1997).

Xu, Y. & Kool, E. T. High sequence fidelity in a non-enzymatic DNA autoligation reaction. *Nucleic Acids Res* 27, 875-881 (1999).

Tang, Z. et al. Real-time monitoring of nucleic acid ligation in homogenous solutions using molecular beacons. *Nucleic Acids Res* 31, e148-e148 (2003).

Tong, J., Cao, W. & Barany, F. Biochemical properties of a high fidelity DNA ligase from *Thermus* species AK16D. *Nucleic Acids Res* 27, 788-794 (1999).

Darzacq, X. et al. In vivo dynamics of RNA polymerase II transcription. *Nat Struct Mol Bio/*14, 796-806 (2007).

---

What is claimed is:

1. A method for synthesizing a 3,6-disubstituted 1,2,4,5-tetrazine compound of formula

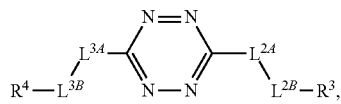

(III)

said method comprising:

combining in a reaction vessel a first substituted nitrile having the formula

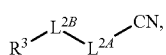

a second nitrile having the formula

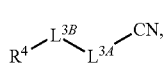

hydrazine, and a Lewis Acid catalyst;

thereby forming a tetrazine of formula

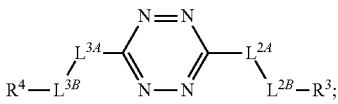

(III)

wherein $R^3$ and $R^4$ are independently hydrogen, halogen, $-N_3$, $-CF_3$, $-CCl_3$, $-CBr_3$, $-CI_3$, $-CN$, $-CHO$, $-OH$, $-NH$, $-NH_2$, $-COOH$, $-CONH_2$, $-NO_2$, $-SH$, $-SO_2$, $-SO_2Cl$, $-SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a detectable moiety, a water soluble moiety or a biomolecule; and $L^{2A}$, $L^{2B}$, $L^{3A}$, and $L^{3B}$ are independently a bond, $-C(O)-$, $-O-$, $-S-$, $-NH-$, $-NR^5-$, $-C(O)NR^6-$, $-S(O)_n-$, $-S(O)NR^7-$, $-OP(O)(OR^8)O-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, wherein -$L^{2A}$-$L^{2B}$-$R^3$ and -$L^{3A}$-$L^{3B}$-$R^4$ are not hydrogen;

$R^5$, $R^6$, $R^7$, $R^8$ are independently hydrogen, halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-OCH_3$, $-NHCNHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n is 1 or 2; and said Lewis Acid catalyst is a metal salt consisting of an anion in combination with a single metal atom selected from the group consisting of Zn, Mg, Cu, Mn, Co, Yb, Sc and Ni.

2. The method of claim 1, wherein said first substituted nitrile or second substituted nitrile is acetonitrile.

3. The method of claim 1, wherein said metal is Zn.

4. The method of claim 1, wherein said metal is Ni.

5. The method of claim 1, wherein said metal salt is a metal triflate.

6. The method of claim 1, wherein said anion is Cl, Br or I.

* * * * *